United States Patent
Ambrosio et al.

(10) Patent No.: US 6,240,918 B1
(45) Date of Patent: Jun. 5, 2001

(54) POWDERED MEDICATION INHALER

(75) Inventors: Thomas J. Ambrosio, Somerville, NJ (US); Warren A. Benson, Jr., Woodville, WI (US); Kim C. Dao, Wayne; David J. Kenyon, Morristown, both of NJ (US); Walter J. Kreiseder, Barrington, IL (US); Theodore J. Schonebaum, Menomonie, WI (US); Allen J. Vogel, Long Grove, IL (US); Louis B. Walker, Menomonie, WI (US); Tsong-Toh Yang, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 08/803,363

(22) Filed: Feb. 20, 1997

Related U.S. Application Data

(60) Provisional application No. 60/012,029, filed on Feb. 21, 1996.

(51) Int. Cl.⁷ .................. A61M 15/00; A61M 16/00; B05D 7/14; B65D 83/06
(52) U.S. Cl. .................. 128/203.15; 128/203.12
(58) Field of Search ............ 128/203.12, 203.15, 128/203.23, 200.14, 200.17, 200.18; 25/FOR 99

(56) References Cited

U.S. PATENT DOCUMENTS

| | | | |
|---|---|---|---|
| 2,432,641 | * 12/1947 | Wilson | 222/567 |
| 2,456,451 | * 12/1948 | Seaver | 128/203.15 |
| 2,604,094 | 7/1952 | Miller et al. | 128/206 |
| 3,024,787 | * 3/1962 | Birch et al. | 128/203.12 |
| 3,587,573 | * 6/1971 | Flack | 128/202.21 |
| 3,687,375 | * 8/1972 | Griffiths | 239/557 |
| 4,668,218 | 5/1987 | Virtanen | 604/58 |
| 4,907,583 | 3/1990 | Wetterlin et al. | 128/203.15 |
| 5,033,463 | 7/1991 | Cocozza | 128/203.21 |
| 5,113,855 | * 5/1992 | Newhouse | 128/203.12 |

(List continued on next page.)

FOREIGN PATENT DOCUMENTS

| | | | |
|---|---|---|---|
| 0 652 022 | 5/1995 | (EP) | A61M/15/00 |
| WO 90/07351 | 7/1990 | (WO) | A61M/13/00 |
| WO 90/10470 | * 9/1990 | (WO) | 128/203.15 |
| WO 91/12040 | * 8/1991 | (WO) | 128/203.15 |
| WO 94/12230 | 6/1994 | (WO) | A61M/15/00 |

*Primary Examiner*—Aaron J. Lewis
*Assistant Examiner*—Joseph F. Weiss, Jr.
(74) *Attorney, Agent, or Firm*—Robert A. Franks

(57) ABSTRACT

A powder dispenser includes a reservoir body including a supply of powder and an inhalation conduit; a driving body for rotating the reservoir body and including upper recesses and two spring fingers in lower driving recesses thereof; a rotatable metering plate for carrying a metered amount of powder from the supply to the inhalation conduit, and having an underside with ribs; a gas permeable retainer welded to the ribs; a spring biasing the metering plate toward the reservoir body; a nozzle having spiked ribs welded in the upper recesses of the driving body and including a chimney with vertical flutes; an adapter non-rotatably mounted with respect to the metering plate and including two locking recesses for receiving the spring fingers for locking engagement and two helical cam tracks with a square cross-section; a closure cap covering the driving body and including priming ribs biasing the spring fingers out of the locking recesses and engaging with the locking recesses to rotate the driving body, and two cams riding within the cam tracks; a base non-rotatably connected with the metering plate; and a counter rotatably mounted on the base and including rotatable counter rings providing a visual count of the number of doses of powder to be dispensed, and a pawl assembly engaging with gear teeth of the counter rings for rotating the same, the pawl assembly including an outer wall, a pawl and a pawl spring integrally molded as a single piece.

37 Claims, 32 Drawing Sheets

U.S. PATENT DOCUMENTS

| | | | |
|---|---|---|---|
| 5,129,582 | * 7/1992 | Rieke et al. | 239/424.5 |
| 5,351,683 | 10/1994 | Chiesi et al. | 128/203.12 |
| 5,394,868 | * 3/1995 | Ambrosio et al. | 128/203.15 |
| 5,415,162 | * 5/1995 | Casper et al. | 128/203.12 |
| 5,429,122 | * 7/1995 | Zanen et al. | 128/203.15 |
| 5,503,144 | * 4/1996 | Bacon | 128/203.15 |
| 5,549,101 | 8/1996 | Trofast et al. | 128/203.15 |
| 5,645,050 | * 7/1997 | Zierenberg et al. | 128/203.15 |
| 5,687,710 | * 11/1997 | Ambrosio et al. | 128/203.15 |
| 5,740,792 | * 4/1998 | Ashley et al. | 128/203.15 |
| 5,740,794 | * 4/1998 | Smith et al. | 128/203.15 |
| 5,765,552 | * 6/1998 | Zanen et al. | 128/203.15 |
| 5,785,049 | * 7/1998 | Smith et al. | 128/203.15 |
| 5,829,434 | * 11/1998 | Ambrosio et al. | 128/203.15 |

* cited by examiner

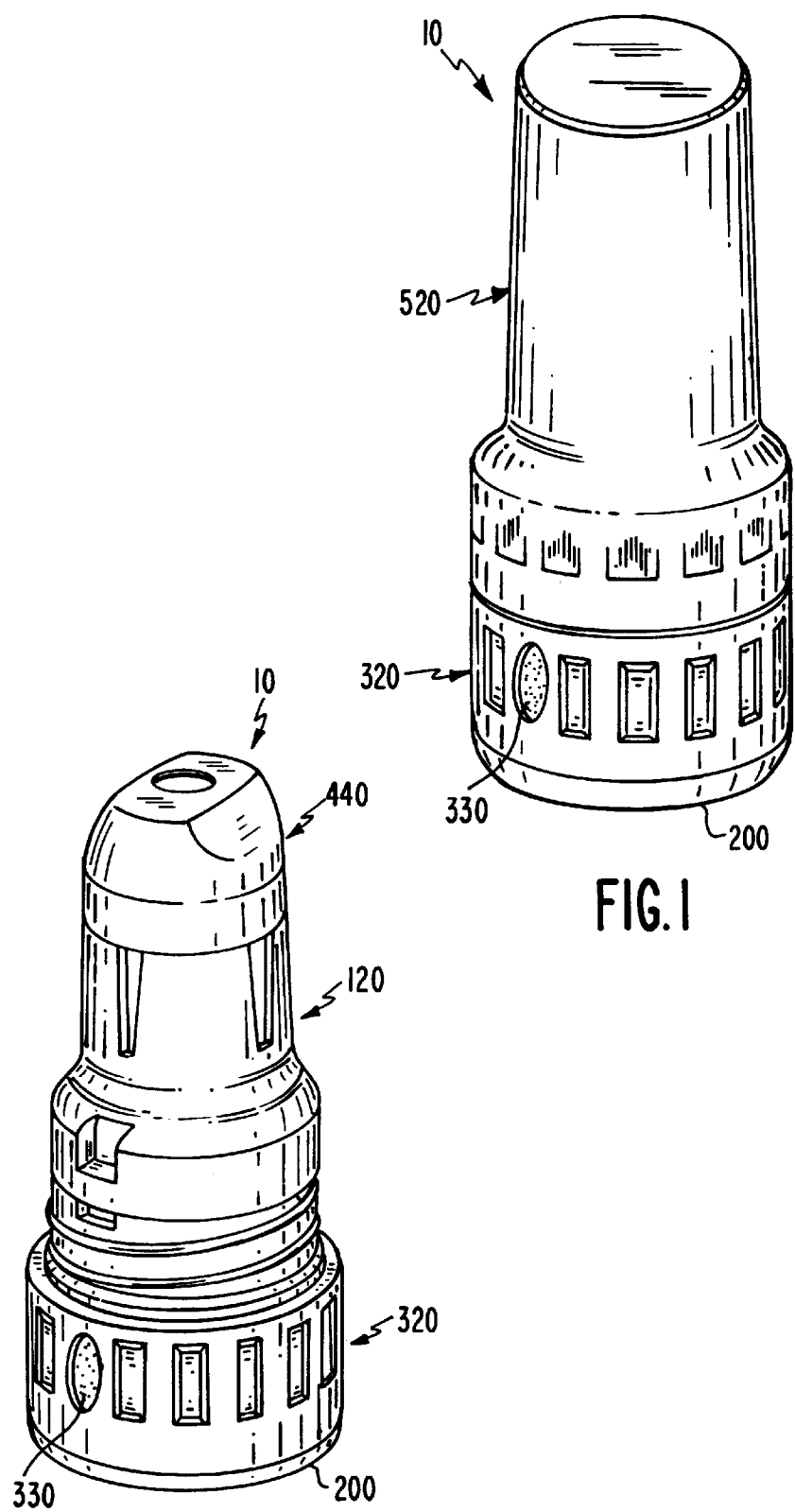

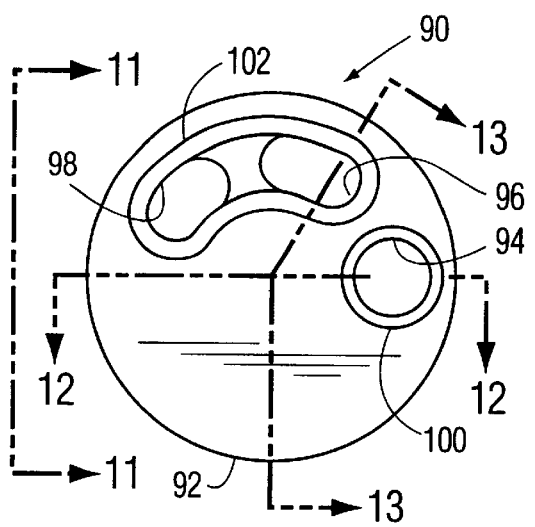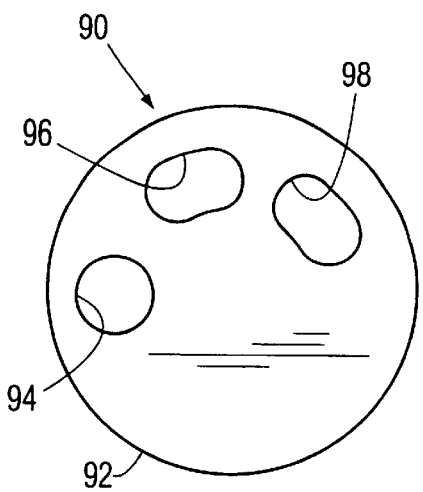
FIG. 9  FIG. 10
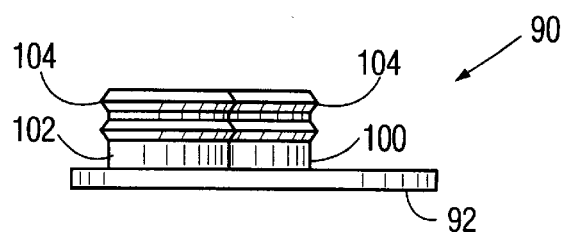
FIG. 11
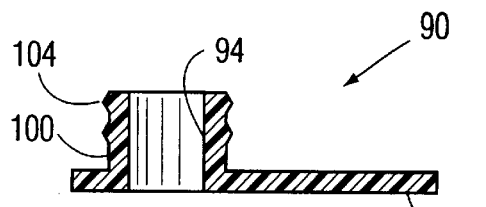
FIG. 12
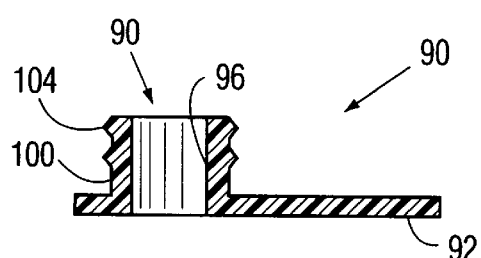
FIG. 13

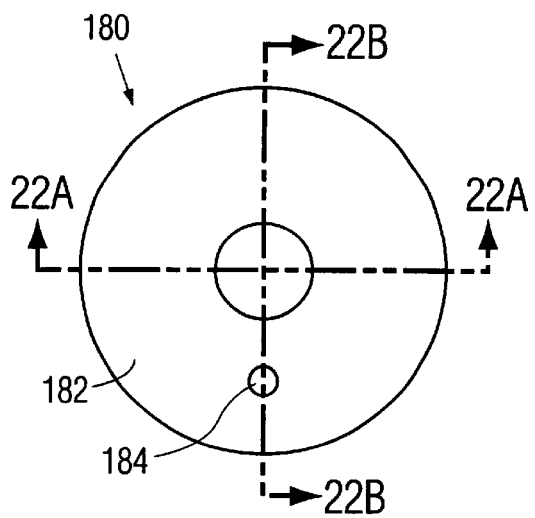
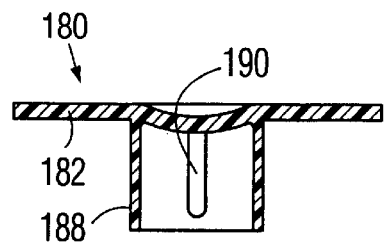
FIG. 22
FIG. 22A
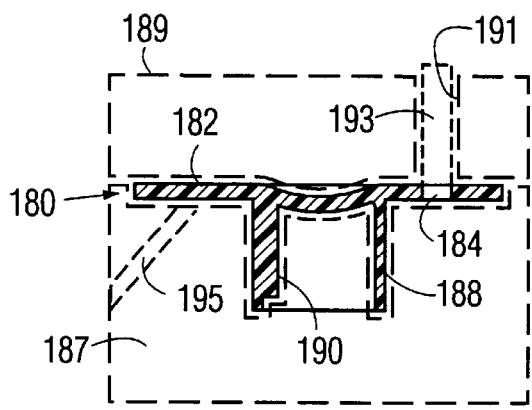
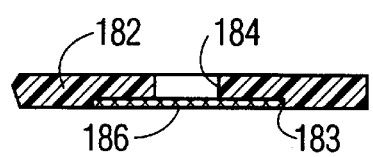
FIG. 22B
FIG. 22C
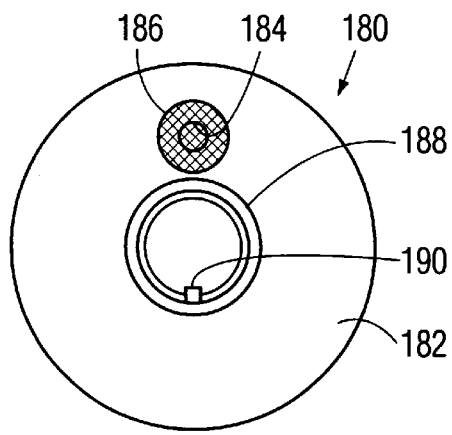
FIG. 23

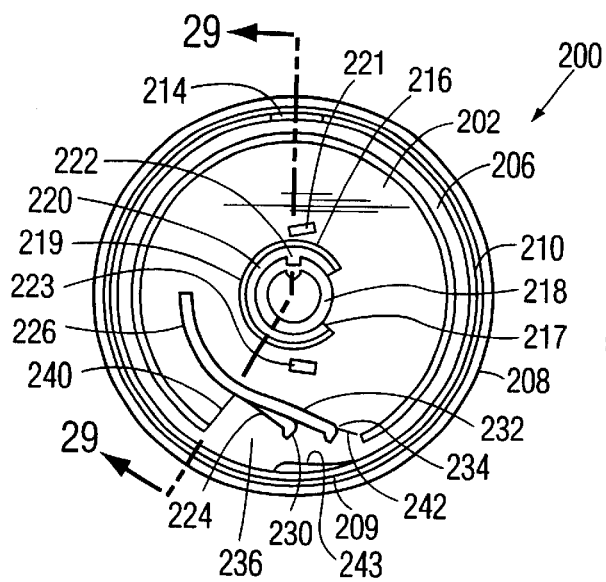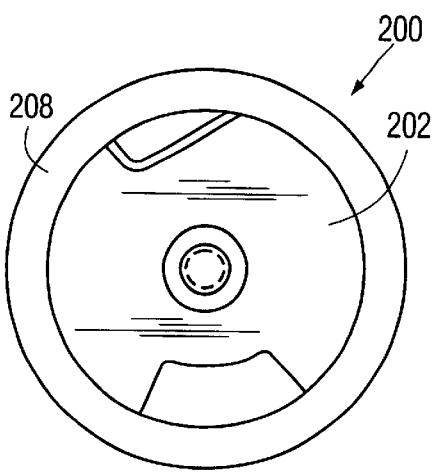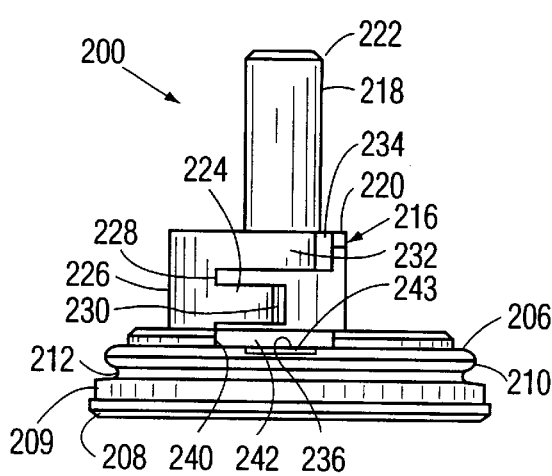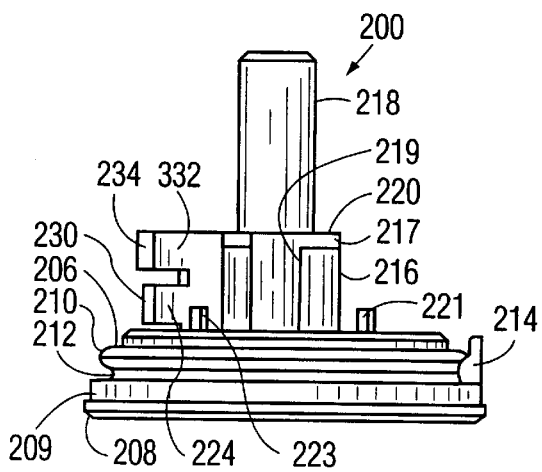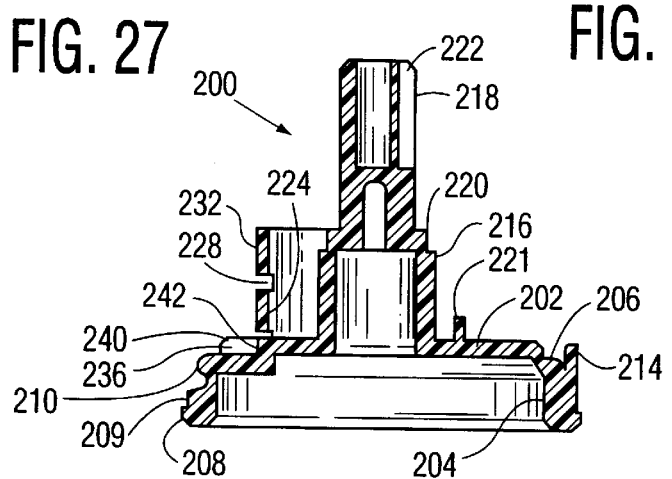

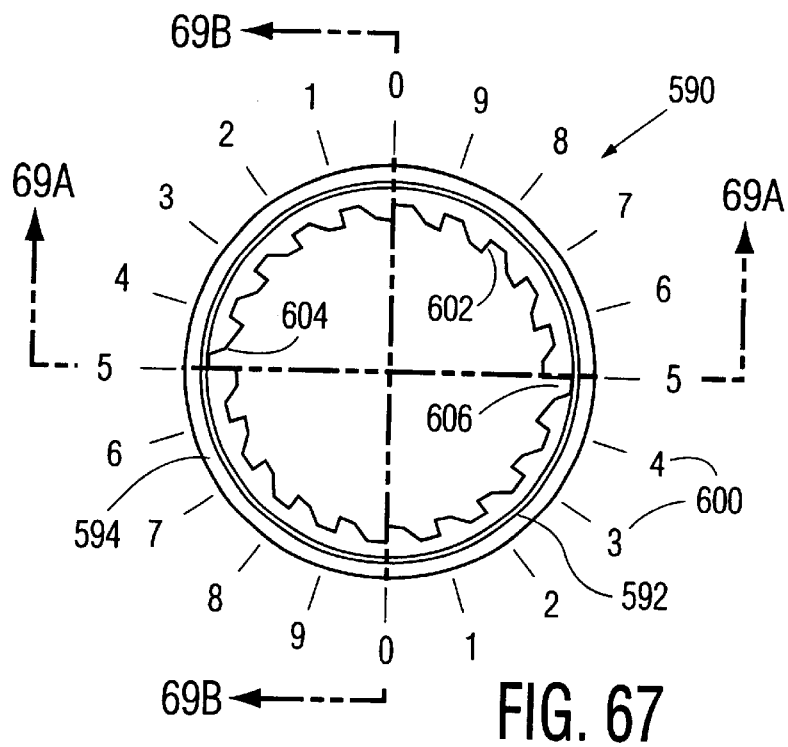
FIG. 67
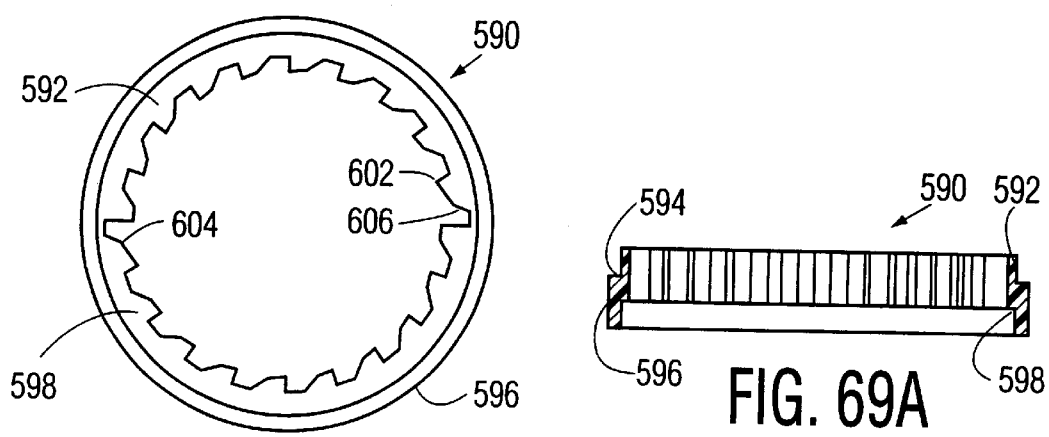
FIG. 68
FIG. 69A
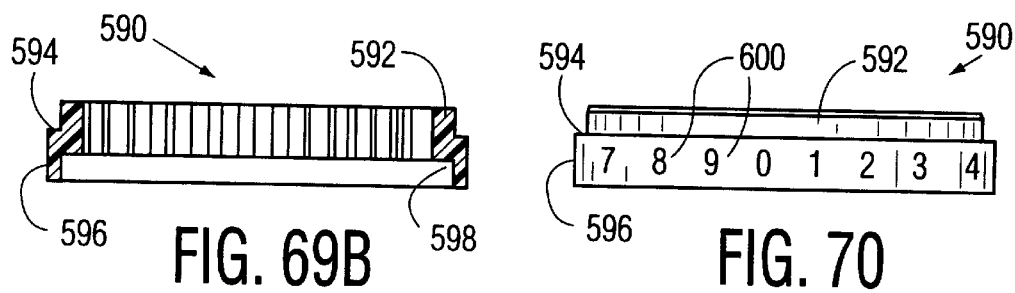
FIG. 69B
FIG. 70

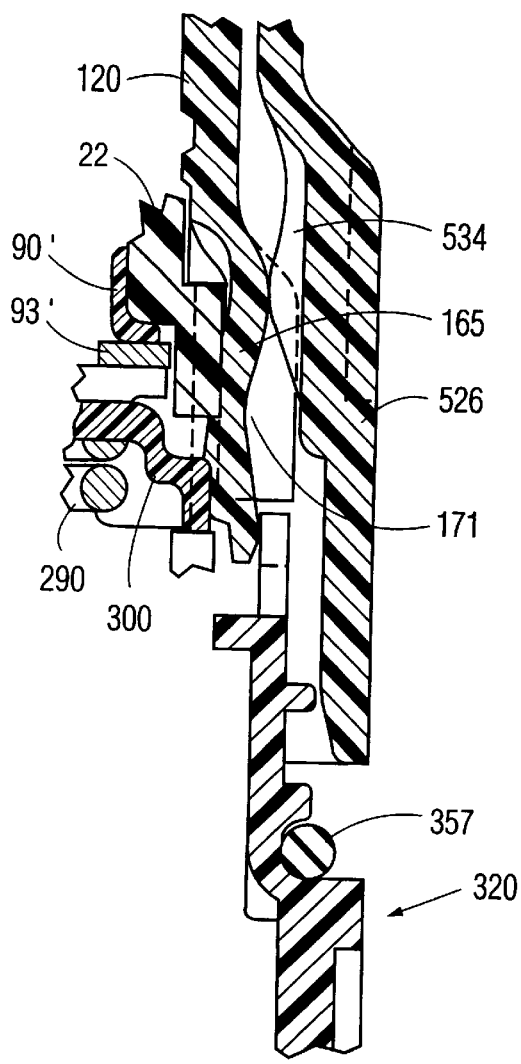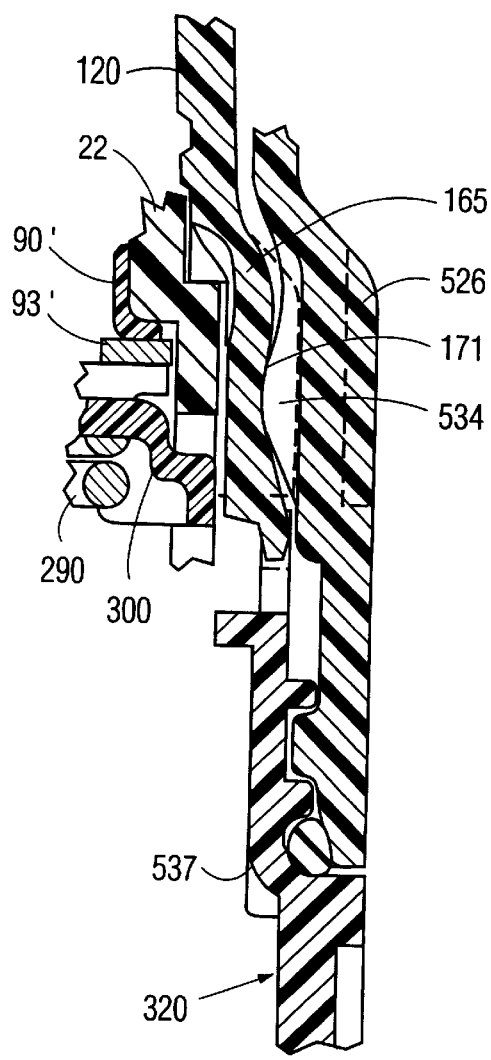
FIG. 90A
FIG. 90B

POWDERED MEDICATION INHALER

CROSS-REFERENCE TO RELATED APPLICATION

The benefits under 35 U.S.C. §119(e) are hereby claimed from provisional application Ser. No. 60/012,029 filed Feb. 21, 1996.

INTRODUCTION TO THE INVENTION

The present invention relates generally to powder dispenser assemblies and, more particularly, is directed to a powder dispenser assembly used for inhalation of a metered dose of a powdered medicament.

When delivering medicaments, that is, pharmacologically active compounds, in solid form to the respiratory tract and to the lungs, careful attention to the accuracy of the dosage, which can be smaller than 0.1 milligram, must be made. This is because such medicaments are often quite potent, and the administration of excessive amounts thereof could be harmful to the patient. Further, if the dosage that is delivered is too small, it will not serve its purpose.

It is also necessary that the particles leaving the dispenser assembly be substantially within a particular size range, since particles of the medicament which are too large may not enter a desired lower portion of the respiratory tract, such as the bronchial tree or lungs, but instead will be deposited in the mouth or pharynx and thence enter the digestive tract. As an example, preferred particles usually are considered as having a diameter less than about 10 micrometers.

Various devices have been used in order to dispense a metered dose of powdered medicament, including pressurized aerosol devices, nebulizing devices, pump inhalators and the like. With the current concern over environmental issues, however, aerosol devices, which constitute a large part of the devices now on the market, are less favored. Further, with aerosol devices, the medicament is dissolved or suspended in a liquid propellant mixture, which results in the introduction of unneeded chemical substances into the body and further adds to the complexity of the devices.

In addition to the aforementioned types of dispenser assemblies, powder dispenser assemblies are also known. Studies have shown that there are virtually no significant differences in bronchodilator responses with equivalent amounts of medicinal substances administered either by powder dispensing devices or aerosol devices. Accordingly, there is now an ever-growing demand for powder dispensing devices which can dispense metered doses of powdered medicament. With such devices, the powder is automatically withdrawn during inspiration so there is less need to be concerned with synchronizing release of medication with the exact start of inspiration to insure quality of the product delivery.

One such device has been described in published International Patent Application No. WO 94/14492. However, it has been discovered that various enhancements thereto are possible and desirable, as will now be described.

In the first place, when agglomerates comprised of hard particles are used, for example, having a bulk density of 0.29 to 0.36 g/ml, in contrast to standard agglomerates having a bulk density of approximately 0.27 g/ml, the respirable fraction, that is, the portion of the particles that can enter the lower airway, may be less than that which is desirable. For example, experiments have shown that the respirable fraction from the powder dispenser of the aforementioned international application for a formulation of mometasone/lactose agglomerates having a component weight ratio of 1:5.8 provides only about 10% of total particles having diameters less than about 6.8 micrometers. It has been determined that one of the likely reasons for this is the swirl nozzle design which does not sufficiently break up the hard agglomerates.

Another potential problem with such design is that the screw threads on the cap and adapter provide a condition in which the cap may be prematurely pulled off due to the tolerances of the screw threads. As a result, the dispenser may not be turned a full 180°, as required. Thus, the proper dosage may not be provided, and the counter mechanism may not be activated. Further, by prematurely pulling the cap off, it may not be possible to easily reapply the cap to the dispenser to close the same.

Also, positioning of the cap for the rotating operation may not always result in accurate alignment.

Another possible problem is that of securing the powder retainer to the metering dose plate. If a hot melt adhesive is used, the adhesive may leak into the mesh, so that quality and consistency is not obtained. Further, by heating the same, there may be a distortion in the flatness and/or damage to the mesh.

A yet further potential problem is that the pawl used in the counter mechanism of the primary embodiment thereof requires an additional metal spring to be inserted therein. This increases the number of parts, makes assembly more difficult, provides a pawl assembly that is not totally moldable and does not always provide a totally reliable counter mechanism. Although a totally molded spring and pawl assembly is disclosed in a later embodiment thereof, such totally molded spring and pawl assembly is more difficult to mold and is not as satisfactory in use to that of the primary embodiment.

A still further potential problem relates to the indicia on the continuous and intermittent counter rings of the counter mechanism, that is, the dispenser must be tipped to a horizontal position to read the numbers, rather than providing the indicia for reading while the dispenser remains in its normal upright position.

Lastly, the swirl nozzle and mouthpiece can be fairly easily disengaged from the drive body during inhalation, possibly resulting in swallowing of the same or choking. The same considerations are not applicable to disengagement of the mouthpiece from the swirl nozzle because of the inclined sides of the mouthpiece.

SUMMARY OF THE INVENTION

In accordance with an aspect of the present invention, a powder dispenser includes a supply for holding a supply of powdered material to be dispensed; an inhalation conduit extending in a first direction and positioned in displaced relation to said supply; means for carrying a predetermined amount of said powdered material from said supply to said inhalation conduit; and a nozzle for reducing particle sizes of agglomerates of powdered material from the inhalation conduit to form micronized powdered material and for mixing said micronized powdered material with suction air, said nozzle including a cavity for changing the direction of flow of said powder from said first direction of said inhalation conduit to a second direction different from said first direction, said cavity being defined by a top wall and a skirt connected to a periphery of said top wall, said top wall having an opening therein; a swirl wall for substantially continuously changing the direction of flow of the powder in the second direction in the cavity; and a chimney extending from the top wall in surrounding relation to the opening for changing the direction of flow of the powder from the second direction of the cavity substantially back to the first direction, the chimney extending along an axial direction thereof and including an inner tubular wall surface having irregularities extending in the axial direction.

Preferably, the irregularities are formed by a plurality of flutes on the inner tubular wall surface, and the flutes are formed by a plurality of first concave wall sections extending in the axial direction and having an arc of a first radius in a direction transverse to the axial direction, and a plurality of second wall sections extending in the axial direction and interconnecting the first concave wall sections, the second wall sections being of a concave configuration having an arc of a second radius in a direction transverse to the axial direction, the second radius being greater than the first radius.

The top wall has a circular shape and the opening is centrally located in the top wall, and the swirl wall includes a curved wall extending from the opening to the skirt, the curved wall extending in a substantially spiral manner and being connected with the top wall.

In accordance with another aspect of the present invention, a powder dispenser includes a powder housing for holding a supply of powdered material to be dispensed, the powder housing including an inhalation conduit extending therethrough in a first direction, in displaced relation to the supply of powdered material, the powder housing including a reservoir body including the supply of powdered material and the inhalation conduit, and a driving body secured to the reservoir body for driving the reservoir body in a rotational direction, the driving body including a plurality of recesses in an upper portion thereof; a metering plate for holding a metered amount of the powdered material, the metering plate including a metered dose hole for holding the metered amount of the powdered material, the metering plate being positionable below the supply of powdered material, and the metering plate and the powder housing being relatively bi-directionally rotatable with respect to each other about a common central axis so that the metered dose hole can be placed in fluid communication selectively with the supply of powdered material or the inhalation conduit; a spring for biasing the metering plate and the powder housing toward each other; and a nozzle mounted to the driving body for receiving the metered amount of the powdered material through the inhalation conduit, the nozzle including ribs welded in the recesses of the driving body.

The driving body has a circular top wall, and the recesses are arranged along a peripheral portion of the top wall along a common circle. At least one of the recesses extends for a different length than another of the recesses, and the ribs have lengths corresponding to respective ones of the recesses.

Preferably, the ribs and the driving body are made from a plastic material, and the ribs are ultrasonically welded in the recesses of the driving body such that the plastic material of the ribs is fused into the plastic material of the recesses.

In accordance with still another aspect of the present invention, in addition to the aforementioned powder dispenser including the powder housing having the reservoir body and the driving body, the metering plate, and the spring, the driving body includes at least one driving recess with a spring finger in each driving recess and the powder dispenser further includes an adapter non-rotatably mounted with respect to the metering plate, the adapter including at least one locking recess for receiving the at least one spring finger therein to prevent rotation of the powder housing relative to the adapter and the metering plate; and a closure cap for covering the powder housing and for priming the powder dispenser for use, the closure cap including priming ribs for rotating the powder housing such that the inhalation conduit is in communication with the metered dose hole when the closure cap is removed from covering relation of the powder housing and for rotating the powder housing such that the inhalation conduit is out of communication with the metered dose hole when the closure cap is secured in covering relation to the powder housing, the priming ribs biasing the at least one spring finger out of the at least one locking recess of the adapter to enable rotation of the powder housing relative to the metering plate and for engaging with the at least one driving recess to rotate the powder housing relative to the metering plate.

Specifically, the driving body includes two diametrically opposite spring fingers, the adapter includes two diametrically opposite locking recesses and the cap includes at least two diametrically opposite priming ribs.

Each priming rib includes an upper ramp portion and a lower ramp portion which meet at an intermediate projecting portion and reduce in thickness as they move away from the projecting portion, such that the upper ramp portion initially biases the at least one spring finger out of the at least one locking recess during removal of the closure cap from the covering relation and the lower ramp portion initially biases the at least one spring finger out of the at least one locking recess during securement of the closure cap to the covering relation.

Each spring finger includes a depression which receives the projecting portion when the closure cap is fully secured in the covering relation.

In accordance with yet another aspect of the present invention, in addition to the aforementioned powder dispenser including the powder housing having the reservoir body and the driving body, the metering plate, the spring, the adapter and the closure cap, the adapter further includes at least one helical cam track having a substantially square cross-sectional configuration, and the closure cap includes an annular skirt having an inner surface, and at least one cam formed on a lower portion of the inner surface of annular skirt for riding within the at least one helical cam track.

Each cam track includes an entry portion defining a vertical drop zone in which the at least one cam engages prior to permitting helical movement of the at least one cam within the at least one cam track. Preferably, there are two helical cam tracks and two cams.

In accordance with a further aspect of the present invention, in addition to the aforementioned powder dispenser including the powder housing having the reservoir body and the driving body, the metering plate, the spring, the adapter and the closure cap, the powder dispenser includes a gas permeable retainer for retaining a dose of the powdered material in the metered dose hole, the retainer being positioned below the metered dose hole, with the metering plate having an underside with ribs thereon, the retainer being positioned in overlying relation to the underside of the metering plate and to the ribs thereon; and the retainer being welded to the ribs such that the ribs are fused into the retainer.

The retainer is formed by a material selected from the group consisting of a gas-permeable filter, a mesh screen, a porous material mesh and a perforated plate element, and is ultrasonically welded to the ribs.

Preferably, the ribs are formed in a plurality of spaced apart, concentric circles, and each rib has a substantially triangular cross-sectional configuration.

In accordance with a still further aspect of the present invention, a method of forming a modified metering plate and gas permeable retainer thereon, includes the steps of positioning the gas permeable retainer at a predetermined position in a first mold half used for injection molding the metering plate; positioning a second mold half adjacent the first mold half to form a molding chamber therebetween used for injection molding the metering plate, the second mold half having a through opening therein in alignment with the retainer at the predetermined position in the first mold half; inserting a core pin through the through opening in the second mold half into engagement with the retainer to hold the retainer in position against the first mold half and to form a metered dose hole in the molded metering plate; and injecting plastic material into the molding chamber through at least one injection port to form the metering plate with the metered dose hole and with the retainer being secured to an underside of the metering plate in covering relation to the metered dose hole.

In such case, the molded metering plate has a shallow recess formed at the underside thereof in surrounding relation to the metered dose hole, and the powder retainer has dimensions greater than the metered dose hole to completely cover the metered dose hole and less than the shallow recess so as to be secured to the metering plate in the shallow recess.

In accordance with a yet further aspect of the present invention, in addition to the aforementioned powder dispenser including the powder housing having the reservoir body and the driving body, the metering plate, the spring, the adapter and the closure cap, the powder dispenser includes a base having an axially extending retaining post thereon coaxial with the common axis and non-rotatably connected with the metering plate, and a counter mechanism, rotatably mounted on the base in surrounding relation to the retaining post, for providing a visual count of the number of doses of the powdered material that have been dispensed or remain to be dispensed in response to the relative rotation of the powder housing and the metering plate, the counter mechanism including counter rings for providing the visual count, the counter rings being rotatable about the common central axis and having counting indicia thereon for displaying the visual count, the counter rings including a continuous counter ring having counting indicia thereon and gear teeth formed therearound on an inner surface thereof, and an intermittent counter ring coaxially mounted with the continuous counter ring and having counting indicia thereon and gear teeth formed therearound on an inner surface thereof, a display through which one of the counting indicia from the counter rings is displayed to indicate a count corresponding to a number of doses of powdered material that have been dispensed or remain to be dispensed; and an actuator for incrementally rotating the counter rings in response to the relative rotation between the metering plate and the powder housing, the actuator including a pawl assembly engaging with the gear teeth of the continuous counter ring and the intermittent counter ring for rotating the continuous counter ring one increment each time that a dose of the powdered material is dispensed to display another one of the counting indicia of the continuous counter ring through the display, and for rotating the intermittent counter ring one increment every predetermined number of rotational increments of the continuous counter ring to display another one of the counting indicia of the intermittent counter ring through the display, the pawl assembly including an outer wall having an outer surface and an inner surface, a pawl, integrally molded as a single piece with the outer surface of the outer wall, for engagement within the gear teeth of one of the continuous counter ring and the intermittent counter ring, and a pawl spring, integrally molded as a single piece with the inner surface of the outer wall, for biasing the pawl into engagement with the gear teeth of the continuous counter ring and the intermittent counter ring, the pawl spring extending along a generally radial direction.

In one embodiment, the pawl spring has a generally L-shaped configuration. In another embodiment, the pawl spring has a generally linear configuration and extends at an angle from the inner surface of the outer wall. In either case, the pawl spring has one end integrally molded with an upper portion of the inner surface of the outer wall.

The above and other features of the invention will become readily apparent from the following detailed description thereof which is to be read in connection with the accompanying drawings.

BRIEF DESCRIPTION OF THE DRAWINGS

FIG. 1 is a perspective view of a metered powder dose dispenser according to the present invention;

FIG. 2 is a perspective view of the metered powder dose dispenser of FIG. 1, with the closure cap removed;

FIG. 9 is a top plan view of the reservoir plug of the metered powder dose dispenser of FIG. 1;

FIG. 10 is a bottom plan view of the reservoir plug of FIG. 9;

FIG. 11 is a side elevational view of the reservoir plug of FIG. 9, viewed from line 11—11 thereof;

FIG. 12 is a cross-sectional view of the reservoir plug of FIG. 9, taken along line 12—12 thereof;

FIG. 13 is a cross-sectional view of the reservoir plug of FIG. 9, taken along line 13—13 thereof;

FIG. 22 is a top plan view of the metering dose plate of the metered powder dose dispenser of FIG. 1;

FIG. 22A is a cross-sectional view of the metering dose plate of FIG. 22, taken along line 22A—22A thereof;

FIG. 22B is a cross-sectional view of the metering dose plate of FIG. 22, taken along line 22B—22B thereof, along with the mold for forming the same in dashed lines;

FIG. 22C is an enlarged cross-sectional view of a portion of the metering dose plate of FIG. 22B;

FIG. 23 is a bottom plan view of the metering dose plate of FIG. 22;

FIG. 25 is a top plan view of the base of the metered powder dose dispenser of FIG. 1;

FIG. 26 is a bottom plan view of the base of FIG. 25;

FIG. 27 is a front elevational view of the base of FIG. 25;

FIG. 28 is a side elevational view of the base of FIG. 25;

FIG. 29 is a cross-sectional view of the base of FIG. 25, taken along line 29—29 thereof;

FIG. 67 is a top plan view of the continuous counter ring of the metered powder dose dispenser of FIG. 1;

FIG. 68 is a bottom plan view of the continuous counter ring of FIG. 67;

FIG. 69A is a cross-sectional view of the continuous counter ring of FIG. 67, taken along line 69A—69A thereof;

FIG. 69B is a cross-sectional view of the continuous counter ring of FIG. 67, taken along line 69B—69B thereof;

FIG. 70 is a side elevational view of the continuous counter ring of FIG. 67;

FIGS. 90A and 90B are enlarged cross-sectional drawings of a portion of the metered powder dose dispenser, during the times of FIGS. 89C and 89E, respectively.

DETAILED DESCRIPTION OF SPECIFIC EMBODIMENTS

Figure 3:
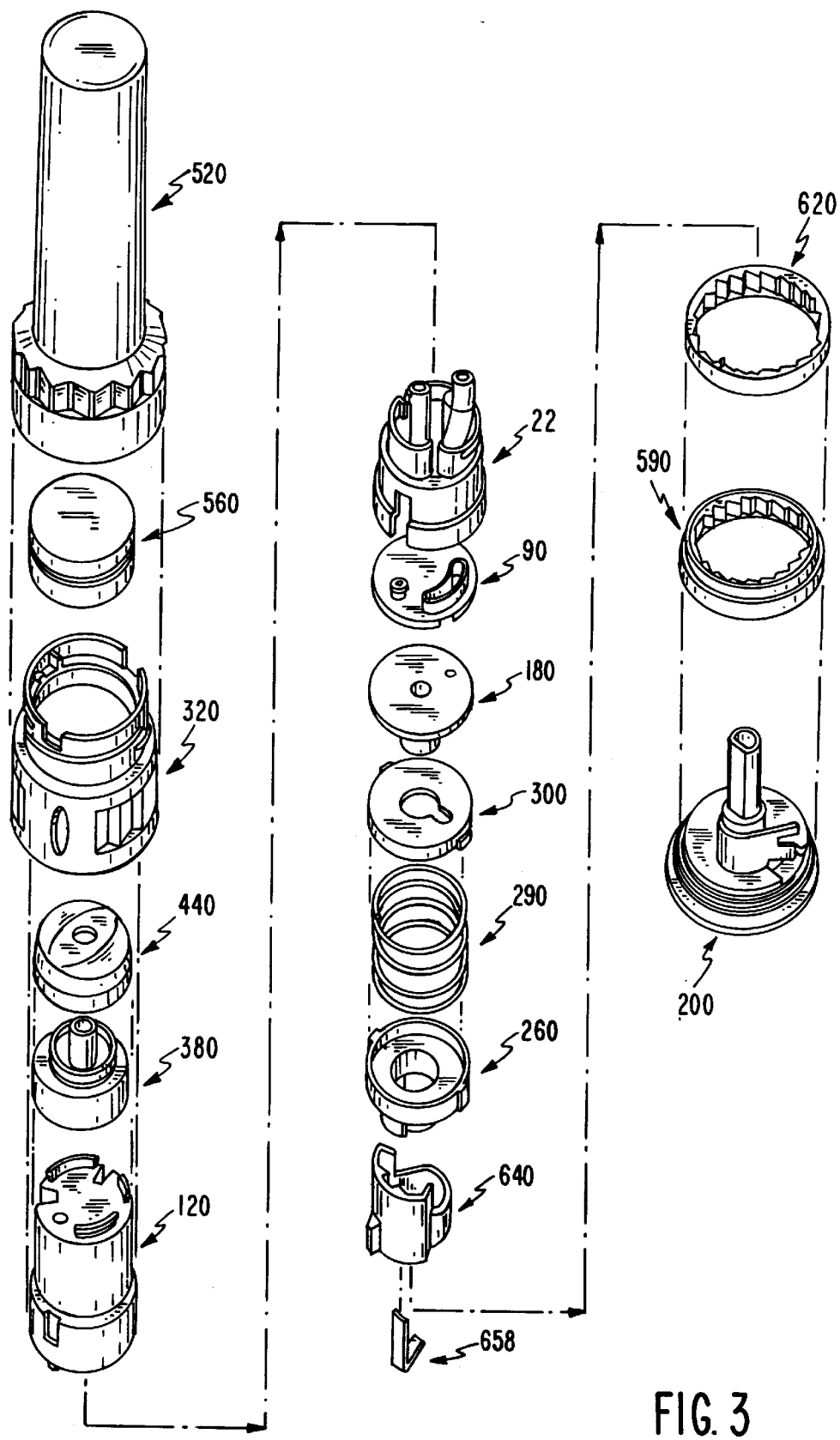
FIG. 3 is an exploded perspective view of the metered powder dose dispenser of FIG. 1.

Referring to the drawings in detail, and initially to FIGS. 1–4 thereof, a metered powder dose dispenser 10 according to the present invention includes a powder housing 20 for holding a supply of powdered material to be dispensed, and for supplying metered doses of the powder to a user.

Powder housing 20 is comprised of a reservoir body 22, a reservoir plug 90 and a driving body 120, each preferably being formed as a single molded plastic piece.

Referring to FIGS. 3–8, reservoir body 22 includes a circular top wall 24 having an annular skirt 26 extending downwardly from the periphery of circular top wall 24. Annular skirt 26 includes an upper annular skirt section 28 with its upper end extending downwardly from the periphery of circular top wall 24, and a lower annular skirt section 30 extending downwardly from the lower end of upper annular skirt section 28. Lower annular skirt section 30 has an inner and outer diameter greater than the inner and outer diameters, respectively, of upper annular skirt section 28. Accordingly, an outer annular shoulder 32 is formed at the upper end of lower annular skirt section 30.

Diametrically opposite, axially extending drive slots 34 and 36 are formed in annular skirt 26, each extending for a different circumferential angular extent about annular skirt 26. For example, drive slot 34 is shown to extend along a 30° arc circumferentially of annular skirt 26, while drive slot 36 is shown to extend along a 40° arc circumferentially of annular skirt 26. Of course, the present invention is not limited to these particular angles. Drive slots 34 and 36 are open at their lower ends 38 and 40, respectively, and extend upwardly entirely through lower annular skirt portion 30 and partially through upper annular skirt portion 28. Thus, drive slots 34 and 36 have closed upper ends which define seating edges 42 and 44.

Powder housing 20 includes an arcuate manifold 46 formed on the upper surface of circular top wall 24, at a peripheral position offset from the center thereof. Manifold 46 includes an arcuate chamber 47 extending circumferentially for an arcuate length of approximately 1400 about a peripheral portion of circular top wall 24 and which is defined by a surrounding chamber wall 48. Specifically, chamber wall 48 is formed by a lower chamber wall portion 50 extending upwardly from circular top wall 24 and an upper chamber wall portion 52 extending upwardly from the upper end of lower chamber wall portion 50. The shapes of wall portions 50 and 52 are substantially identical, but with the inner dimensions of upper wall portion 52 being less than the inner dimensions of lower wall portion 50. As a result, a shoulder 54 is formed at the lower end of upper chamber wall portion 52.

Circular top wall 24 includes an opening 55 of the same shape and dimensions as lower chamber wall portion 50 of manifold 46 and in alignment with the lower end of lower chamber wall portion 50. The upper end of manifold 46, and particularly upper chamber wall portion 52, is closed by a manifold top wall 56 which is angled downwardly from the center thereof and which has an opening 58 at the center thereof.

A powder supply conduit 60 is formed as a supply holder on manifold top wall 52 at the center thereof in alignment with opening 58. The upper end of powder supply conduit 60 is open. Powder supply conduit 60 is normally filled with powder 62 for inhalation. As used herein, the terms "powdered medicaments" and "powder" include micronized powder, spheronized powder, micro-encapsulated powder, powder agglomerates and the like, and are used interchangeably with these terms herein.

A frusto-conical inhalation venturi conduit 64 is also formed on circular top wall 24 substantially parallel to powder supply conduit 60 and axially offset from the central axis of circular top wall 24. The center axis of powder supply conduit 60 and the center axis of venturi conduit 64 lie on a circle having a center coincident with the center of circular top wall 24, so as to be positioned at a peripheral portion of circular top wall 24, the center axes of conduits 60 and 64 being spaced apart along such a circle by an angle of approximately 1050.

Specifically, venturi conduit 64 is formed by a lower venturi conduit section 66 and an upper venturi conduit section 68 axially aligned therewith, each reducing in inner diameter from a lower end thereof to an upper end thereof. The upper end of upper venturi conduit section 68 is open, and upper venturi conduit section 68 has a smaller diameter than lower venturi conduit section 66 so that an inner annular shoulder 70 is formed at the lower edge of upper venturi conduit section 68. Circular top wall 24 includes a further opening 72 of the same shape and dimensions as the lower end of lower venturi conduit section 66 and in alignment therewith.

A peripheral securing wall 74 extends generally about a circular arc on a peripheral portion of circular top wall 24, in surrounding relation to lower chamber wall portion 50 and lower venturi conduit section 66. A gap 76 is provided in securing wall 74 at a position opposite conduits 60 and 64, and two parallel, spaced apart, radially extending tabs 78 extend inwardly from opposite ends of securing wall 74 at gap 76. Further, a radially extending annular lip 80 extends outwardly from the upper end of securing wall 74.

As will be understood from the description hereinafter, it is necessary that the lower surface of circular top wall 24 be as smooth as possible, that is, with very few undulations therein. However, this is difficult to achieve when molding reservoir body 22 as a single piece. Therefore, to overcome this problem, a reservoir plug 90 is provided, as shown in FIGS. 3 and 9–13.

Figure 4:
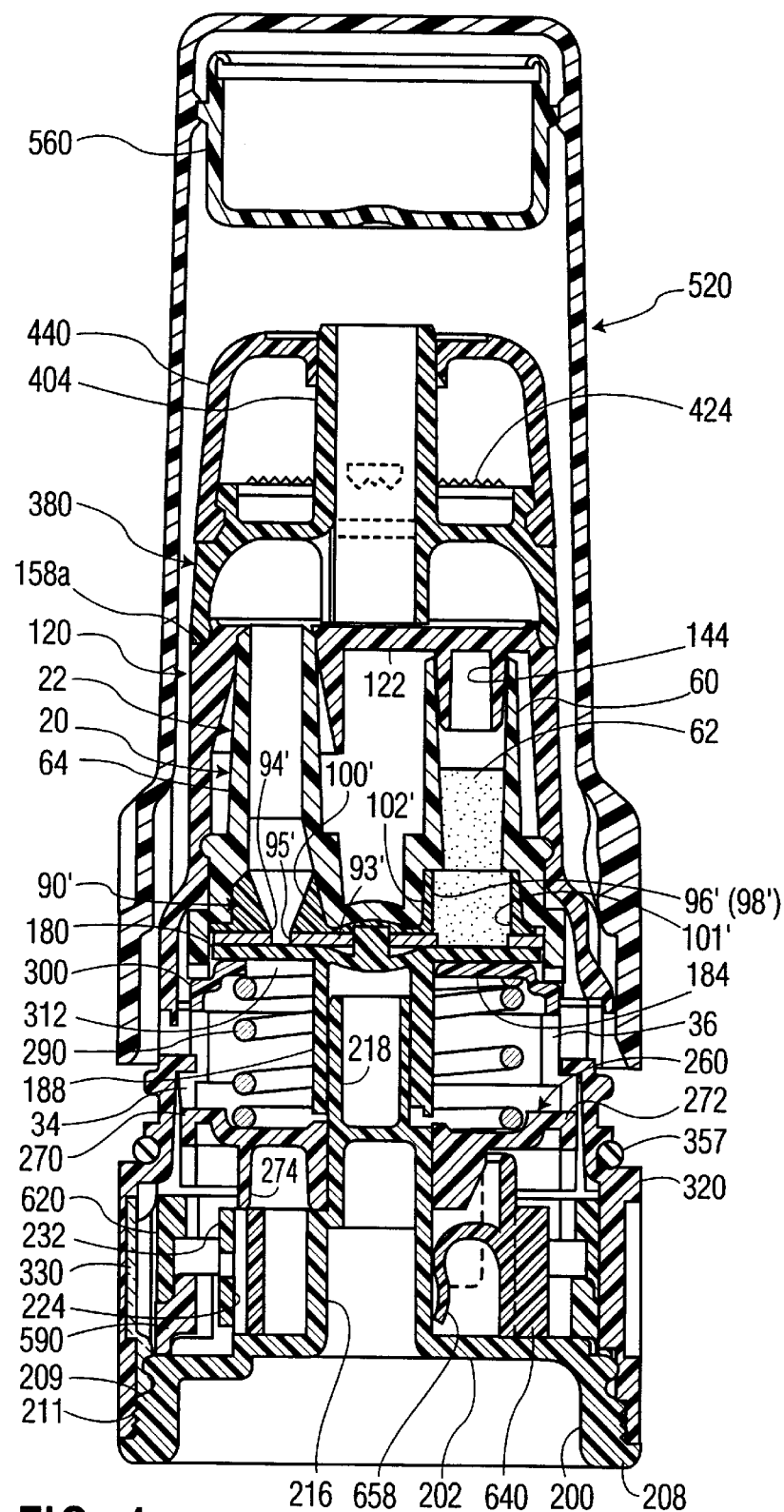
FIG. 4 is a longitudinal cross-sectional view of the metered powder dose dispenser of FIG. 1.
Figure 5:
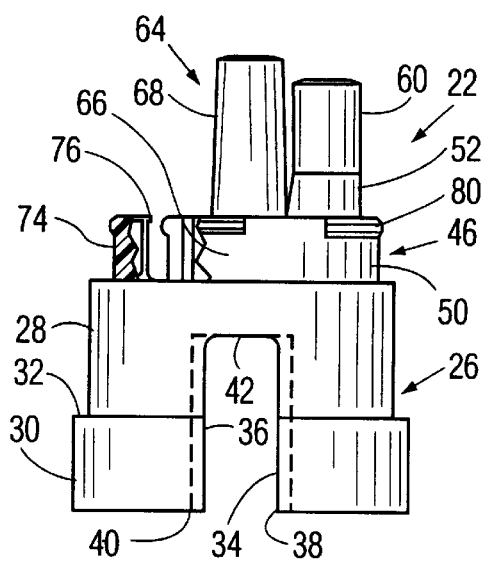
FIG. 5 is a front elevational view, partially in cross-section, of the reservoir body of the metered powder dose dispenser of FIG. 1.
Figure 6:
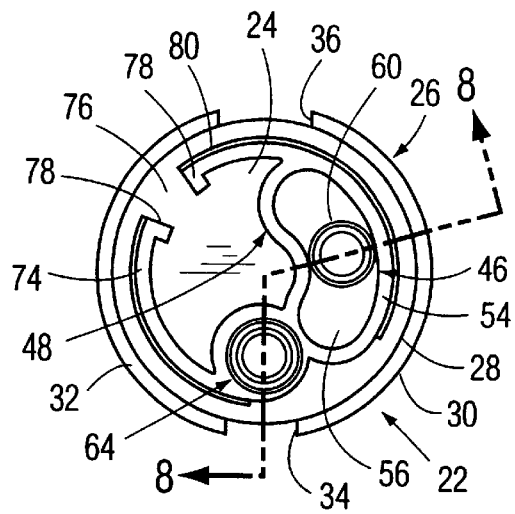
FIG. 6 is a top plan view of the reservoir body of FIG. 5.
Figure 7:
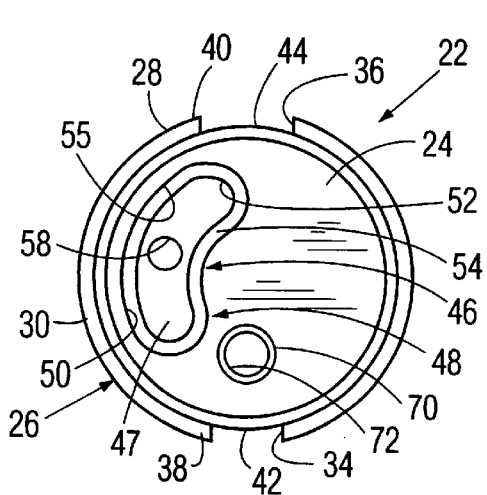
FIG. 7 is a bottom plan view of the reservoir body of FIG. 5.
Figure 8:
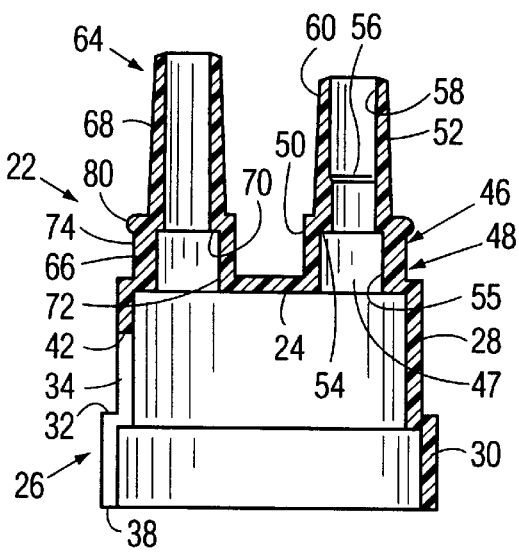
FIG. 8 is a cross-sectional view of the reservoir body of FIG. 6, taken along line 8—8 thereof.
Figure 14:
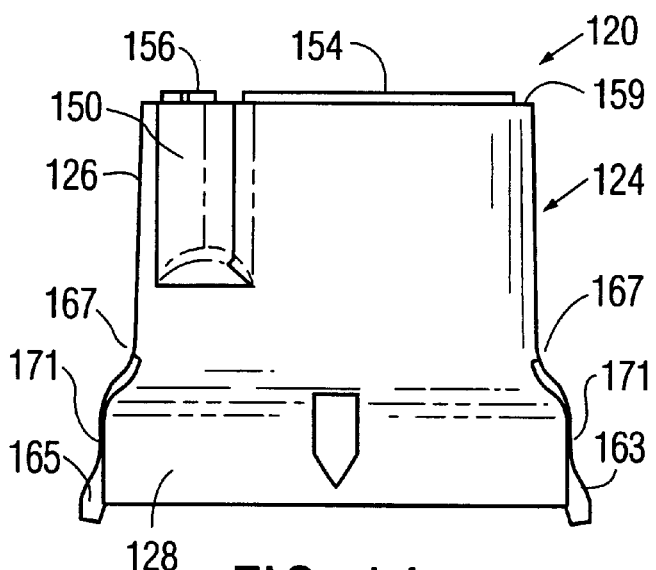
FIG. 14 is a front elevational view of the driving body of the metered powder dose dispenser of FIG. 1.
Figure 15:
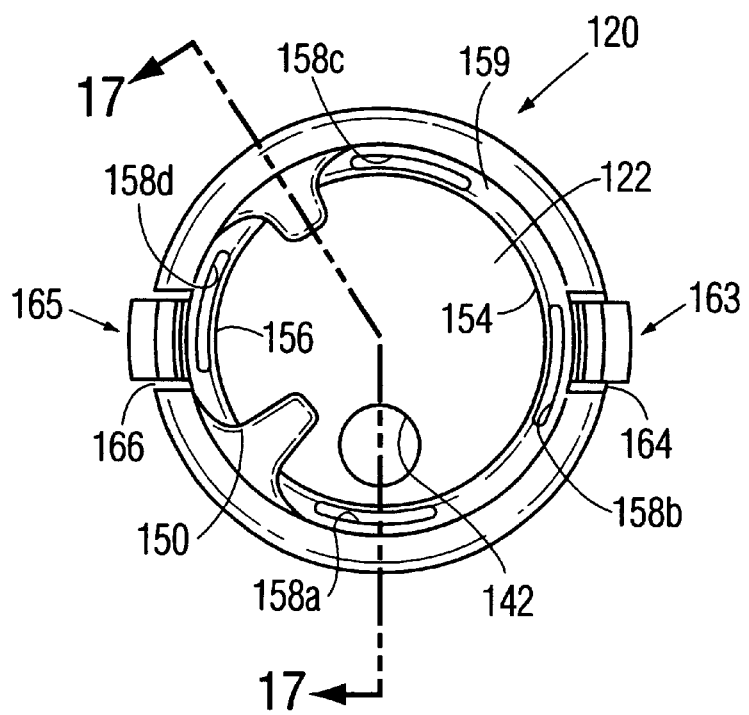
FIG. 15 is a top plan view of the driving body of FIG. 14.
Figure 16:
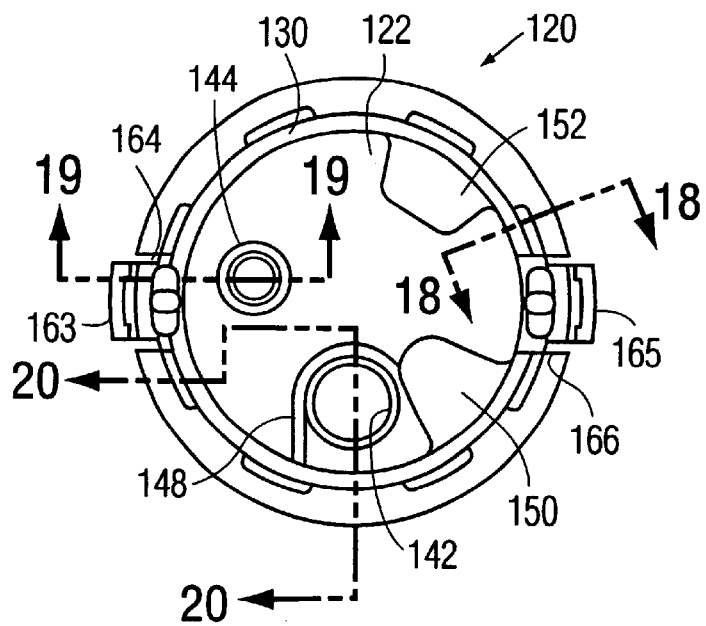
FIG. 16 is a bottom plan view of the driving body of FIG. 14.
Figure 17:
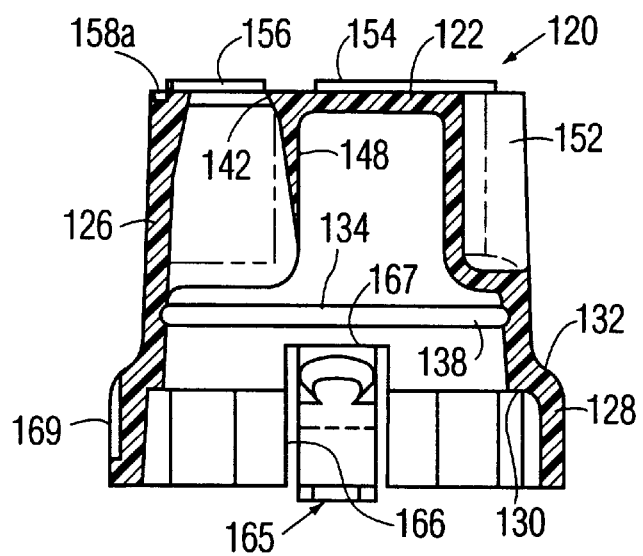
FIG. 17 is a cross-sectional view of the driving body of FIG. 15, taken along line 17—17 thereof.
Figure 18:
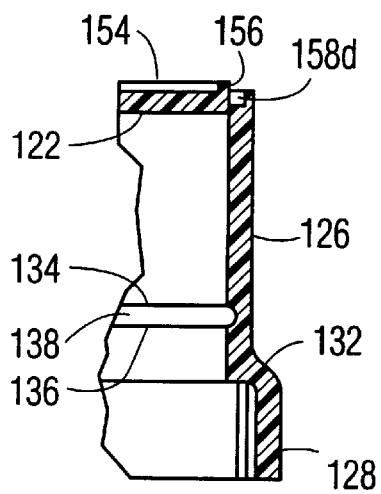
FIG. 18 is a cross-sectional view of the driving body of FIG. 16, taken along line 18—18 thereof.
Figure 19:
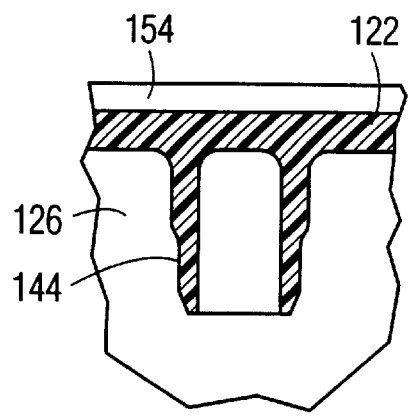
FIG. 19 is a cross-sectional view of the driving body of FIG. 16, taken along line 19—19 thereof.
Figure 20:
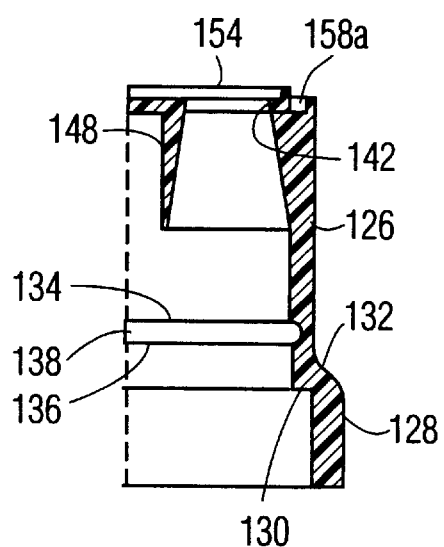
FIG. 20 is a cross-sectional view of the driving body of FIG. 16, taken along line 20—20 thereof.
Figure 21:
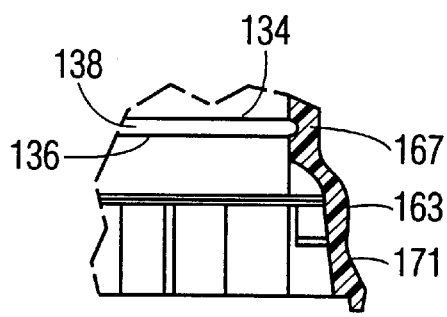
FIG. 21 is a cross-sectional view showing one of the spring fingers.

Specifically, reservoir plug 90 includes a thin circular plate 92 which can be molded, because of the thinness of plate 92, to have a very smooth lower surface with no undulations. The outer diameter of circular plate 92 is substantially equal to the inner diameter of upper annular skirt portion 28 so that reservoir plug 90 can be fit therein, as shown in FIG. 4. In such condition, the lower surface of circular plate 92 effectively is flush with seating edges 42 and 44 of drive slots 34 and 36.

Circular plate 92 has a circular hole 94, a first substantially oval hole 96 and a second substantially oval hole 98, all having centers extending along an imaginary circle centered at the center of plate 92.

A circular plug conduit 100 is formed on the upper surface of circular plate 92 in surrounding relation to circular hole 94. Conduit 100 is open at its upper and lower ends and has an outside diameter and a height substantially equal to the inside diameter and height, respectively, of lower venturi conduit section 66 and an inside diameter equal to the inside diameter of upper venturi conduit section 68. Thus, when reservoir plug 90 is inserted within upper annular skirt section 28, plug conduit 100 fits snugly within lower venturi conduit section 66 and the inner surface of plug conduit 100 forms a smooth continuation of the inner surface of upper venturi conduit section 68. In such condition, the upper edge of plug conduit 100 abuts against annular shoulder 70 so that no gap is formed between plug conduit 100 and upper venturi conduit section 68.

An arcuate plug conduit 102 is formed on the upper surface of circular plate 92 in surrounding relation to first and second substantially oval holes 96 and 98. Plug conduit 102 has the same shape as lower chamber wall portion 50 of manifold 46. Plug conduit 102 is open at its upper and lower ends and has an outside shape and dimensions substantially equal to the inside shape and dimensions, respectively, of lower chamber wall portion 50, inside shape and dimensions equal to the inside shape and dimensions of upper chamber wall portion 52, and a height equal to the height of lower chamber wall portion 50. Thus, when reservoir plug 90 is inserted within upper annular skirt section 28, plug conduit 102 fits snugly within lower chamber wall portion 50 and the inner surface of plug conduit 102 forms a smooth continuation of the inner surface of upper chamber wall portion 52. In such condition, the upper edge of plug conduit 102 abuts against shoulder 54 so that no gap is formed between plug conduit 102 and upper chamber wall portion 52.

Although the outer surfaces of plug conduits 100 and 102 are discussed above as being smooth, it will be appreciated that such outer surfaces can be formed with ribs 104, as shown in FIGS. 11–13.

As an alternative embodiment of reservoir plug 90, a reservoir plug 90' is shown in the cross-sectional FIG. 4, in which elements corresponding to those of reservoir plug 90 are identified by the same reference numerals, with a prime (') appended thereto.

As shown, plug conduit 100' has an inner diameter with a frusto-conical configuration that tapers from an upper end to a lower end thereof, to provide a venturi effect. In addition, the inner diameter of arcuate plug conduit 102' may be greater than the inner diameter of upper chamber wall portion 52'. Further, to better ensure a smooth lower surface, a thin flat, circular metal plate 93' of electropolished stainless steel is secured to the lower surface of reservoir plug 90'. In such case, plate 92' has an opening 101' of the same dimensions as arcuate plug conduit 102', while oval holes 96' and 98' are provided in metal plate 93'. Of course, metal plate 93' has a further circular opening 95' coincident with circular hole 94' of circular plate 92'. Preferably, metal plate 93' is insert molded onto a plastic base material. The metal portion contacts dosing plate 180 in the assembled device, providing a very flat, smooth and rigid surface to prevent powder leakage from the reservoir. In addition, the metal dissipates any static electricity charges generated by friction between surfaces during dose loading operations, which charges can adversely affect powder flow into and out of the dosing station.

As shown in FIGS. 14–21, driving body 120 includes a circular top wall 122 having an annular skirt 124 extending downwardly from the periphery of circular top wall 122.

Annular skirt 124 includes an upper annular skirt section 126 with its upper end extending downwardly from the periphery of circular top wall 122, and a lower annular skirt section 128 extending downwardly from the lower end of upper annular skirt section 126. Lower annular skirt section 128 has an inner and outer diameter greater than the inner and outer diameters, respectively, of upper annular skirt section 126. Accordingly, an inner annular shoulder 130 is formed at the lower edge of upper annular skirt section 126, along the inside of annular skirt 124. However, the outer surface of the transition area between upper annular skirt section 126 and lower annular skirt section 128 is formed as a frusto-conical surface 132.

Further, the inner diameter of lower annular skirt section 128 is substantially the same as the outer diameter of upper annular skirt section 28 of reservoir body 22 and the inner diameter of upper annular skirt section 126 is substantially the same as the outer diameter of peripheral securing wall 74 of reservoir body 22. Accordingly, reservoir body 22 fits into driving body 120 with a close fit until the radially extending annular lip 80 of peripheral securing wall 74 abuts against annular shoulder 130.

In order to lock reservoir body 22 and driving body 120 together in such position, two axially spaced apart, circumferentially extending ribs 134 and 136 are formed parallel to and spaced above annular shoulder 130, on the inner surface of upper skirt section 126, to define an annular holding area 138 therebetween. Thus, when reservoir body 22 is inserted within driving body 120 in the manner described above, lip 80 at the upper end of peripheral securing wall 74, due to the resilience of the plastic pieces, rides along the inner surface of upper skirt portion 126 and over lower rib 136, and is held between ribs 134 and 136 within annular holding area 138.

Circular top wall 122 is formed with a circular opening 142 which is aligned with and receives frusto-conical venturi conduit 64 so that the upper edge of frusto-conical venturi conduit 64 is substantially flush with the upper surface of circular top wall 122.

A circular plug conduit 144 depends downwardly from the lower surface of circular top wall 122 and is in alignment with powder supply conduit 60. Circular plug conduit 144 has an outer diameter substantially equal to or slightly greater than the, inside diameter of powder supply conduit 60. Thus, plug conduit 144 closes the upper open end of powder supply conduit 60 when reservoir body 22 is assembled with driving body 120. Therefore, powder 62 can only escape through manifold 46, opening 55 and substantially oval holes 96 and 98.

Further, a slightly inclined, curved retaining wall 148 extends downwardly from the lower surface of circular top wall 122 in partial surrounding relation to circular opening 142 to ensure a further separation between powder supply conduit 60 and frusto-conical venturi conduit 64 when reservoir body 22 and driving body 120 are assembled.

In order to provide for secondary air flow, as will be described hereinafter, the wall defining upper annular skirt section 126 extends inwardly in the radial direction to form a first outer air passage 150 adjacent to circular opening 142 in the circumferential direction of driving body 120 and a second outer air passage 152 having its center arcuately spaced approximately 100° from the center of first air passage 150.

Short, axially extending upper guide walls 154 and 156 are formed along a common circular arc spaced slightly inwardly from the periphery on the upper surface of circular top wall 122 in order to secure a nozzle to driving body 120, as will be described in greater detail hereinafter. Specifically, upper guide wall 154 is formed circumferentially along the larger arc between air passages 150 and 152; and upper guide wall 156 is formed circumferentially along the smaller arc between air passages 150 and 152. The common circular arc along which upper guide walls 154 and 156 extend is spaced slightly from the peripheral edge of circular top wall 122 so as to define an annular retaining ledge 159-on-circular top wall 122, positioned outwardly of upper guide walls 154 and 156 in the radial direction.

Four substantially equiangularly arranged, elongated arcuate recesses 158a–158d are formed on retaining ledge 159, the purpose for which will be apparent from the discussion hereinafter. Recesses 158a–158d extend along different arcuate distances. For example, recesses 158a and 158c may extend for arcuate distances of 38 degrees; recess 158b for an arcuate distance of 42 degrees and recess 158d for an arcuate distance of 46 degrees.

Further, lower annular skirt section 128 is cut away at two diametrical positions thereof to form two diametrically opposite driving openings 164 and 166 containing two diametrically opposite spring fingers 163 and 165, respectively, extending downwardly and slightly outwardly from their connections 167 at the intersection of upper annular skirt section 126 and lower annular skirt section 128. Spring fingers 163 and 165, as shown, extend below the lower edge of lower annular skirt section 128. As will be described hereinafter, driving openings 164 and 166 are engaged to rotate driving body 120. As shown, each spring finger 163 and 165 is bent or formed into a concave shape so as to have a depression 171 therein, substantially centrally located with respect to the lengthwise direction thereof.

Finally, a recess 169 in the shape of an arrow is formed in lower annular skirt section 128 at a position midway between driving openings 164 and 166, and in radial alignment with circular opening 142, with the arrow pointing downwardly.

In order to provide metered doses of powder 62 from powder supply conduit 60 to venturi conduit 64, a metering dose plate 180 is positioned within upper annular skirt section 28 of reservoir body 22, immediately below reservoir plug 90, as shown in FIGS. 22, 22A–22C and 23. Specifically, metering dose plate 180 includes a thin disc 182 having a single small metered dose hole 184 near the periphery thereof which functions as a single powder receptacle, that is, for holding a metered dose of powder 62. In order to prevent the metered dose of powder from falling through dose hole 184, a powder retainer 186 is formed in covering relation to the lower surface of disc 182, extending at least over dose hole 184. Preferably, powder retainer 186 is formed by a mesh screen, filter, porous material or the like which has a minimal restrictive effect on gas flow therethrough, while preventing appreciable loss of powdered medicament below the lower surface of disc 182. Powder retainer 186 can be fabricated from any suitable material, including cellulosics, polymerics, metals, ceramics, glasses or composites thereof, exemplary useful materials including sintered porous plastics, porous polymer membranes, natural or synthetic woven fabrics, nonwoven synthetic fabrics and the like. More specifically, useful materials include polyester and polyolefin woven mesh, and porous membranes of polyolefins, polycarbonates, polytetrafluoroethylene, polyvinylidene dichloride, and mixed esters of cellulose.

In this regard, metering dose plate 180 has a circular shallow recess 183 at the underside of thin disc 182. Shallow recess 183 is concentric with metered dose hole 184 but has a larger diameter than that of metered dose hole 184. Powder retainer 186 has a circular configuration with an outer diameter equal to the diameter of shallow recess 183 and is secured within shallow recess 183.

With such an arrangement, there is a problem in accurately positioning powder retainer 186 in shallow recess 183. Specifically, with a hot melt adhesive, the adhesive may-leak-into the mesh of powder retainer 186. Further, quality and consistency in positioning of powder retainer 186 therein cannot be obtained by this method. Further, powder retainer 186 may be distorted, thereby deviating from the flatness thereof, or may be damaged, by a heating operation.

Therefore, in accordance with the present invention, to easily and accurately form powder retainer 186 within shallow recess 183, metering dose plate 180 is preferably formed by an insert molding operation.

Specifically, as shown by dashed lines in FIG. 22B, powder retainer 186 is inserted at a predetermined position within a first mold half 187 which is used to form metering dose plate 180. Then, the complementary second mold half 189 is positioned with respect to first mold half 187 to form metering dose plate 180. Second mold half 189 has a through opening 191 in alignment with the predetermined position at which powder retainer 186 is positioned in first mold half 187. A core pin 193 is inserted within opening 191 and serves the dual purposes of holding retainer 186 is place and also forming metered dose hole 184. Then, plastic is injection molded into the mold through at least one injection port 195. As a result, shallow recess 183 is formed around powder retainer 186.

Thus, the injection molding operation results in powder retainer 186 being secured to the plastic, without compromising the flatness or openness of the mesh thereof. Further, a very small mesh screen can be used for powder retainer 186, rather than using a screen occupying the entire undersurface of disc 182, as in the aforementioned copending U.S. Patent Application. The use of a small mesh screen results in more accurate positioning, less undulations therein and being able to be formed with disc 182 in a totally automated manner.

An annular mounting post 188 extends downwardly from the lower surface of disc 182 and is centrally located thereon. Annular mounting post 188 is formed with a bar 190 extending axially along the inner surface of mounting post 188 in diametric relation to metered dose hole 184. Bar 190 extends from the lower surface of disc 182 to a position slightly spaced from the lower edge of mounting post 188, and preferably has a square cross-sectional configuration. As will be understood from the description hereinafter, bar 190 ensures that metering dose plate 180 will remain stationary with respect to powder housing 20 when powder housing 20, which includes reservoir body 22, reservoir plug 90 and driving body 120, is rotated.

In operation, metered dose hole 184 is initially in alignment with frusto-conical venturi conduit 64. As will be explained hereinafter, powder housing 20 is only permitted to rotate 1800 relative to metering dose plate 180. During initial priming rotation, metered dose hole 184 passes under manifold 46 and substantially oval holes 96 and 98. As a result, powder 62 falls within and is scraped into metered dose hole 184. Specifically, the side walls defining substantially oval holes 96 and 98 function to scrape the powder 62 into metered dose hole 184. It will be appreciated that, since oval holes 96 and 98 are spaced less than 180° from circular hole 94, metered dose hole 184 travels completely past oval holes 96 and 98 and manifold 46. Then, during the return rotation back to the initial position, metered dose hole 184 passes back under manifold 46 and substantially oval holes 96 and 98, into alignment with venturi conduit 64. During this return travel, the side walls defining substantially oval holes 96 and 98 again function to scrape the powder 62 into metered dose hole 184, thus ensuring that metered dose hole 184 is completely and accurately filled. Thus, the scraping action is provided during both counterclockwise and clockwise rotation, that is, both during the 180° loading stage and the reverse 180° movement to the inhalation stage. When metered dose hole 184 is aligned with venturi conduit 64, it is then only necessary for the user to inhale through venturi conduit 64, causing a draw and suction through metered dose hole 184, wherein the metered dose of powder 62 is drawn up through venturi conduit 64 and delivered to the user.

A modified metering dose plate 180' will now be described in connection with FIGS. 24A–24F, in which elements corresponding to those of metering dose plate 180 are identified by the same reference numerals with a prime (') added thereto.

Metering dose plate 180' is positioned within upper annular skirt section 28 of reservoir body 22, immediately below reservoir plug 90, as with metering dose plate 180. Specifically, metering dose plate 180' includes a thin disc 182' having a single small metered dose hole 184' near the periphery thereof which functions as a single powder receptacle, that is, for holding a metered dose of powder 62. In order to prevent the metered dose of powder from falling through dose hole 184', a powder retainer 186' is formed in covering relation to the lower surface of disc 182', extending at least over dose hole 184'. Preferably, powder retainer 186' is formed by a mesh screen, filter, porous material or the like which has a minimal restrictive effect on gas flow therethrough, while preventing appreciable loss of powdered medicament below the lower surface of disc 182'. Powder retainer 186' can be fabricated from any suitable material, including cellulosics, polymerics, metals, ceramics, glasses or composites thereof, exemplary useful materials including sintered porous plastics, porous polymer membranes, natural or synthetic woven fabrics, nonwoven synthetic fabrics and the like. More specifically, useful materials include polyester and polyolefin woven mesh, and porous membranes of polyolefins, polycarbonates, polytetrafluoroethylene, polyvinylidene dichloride, and mixed esters of cellulose.

Figure 24A:
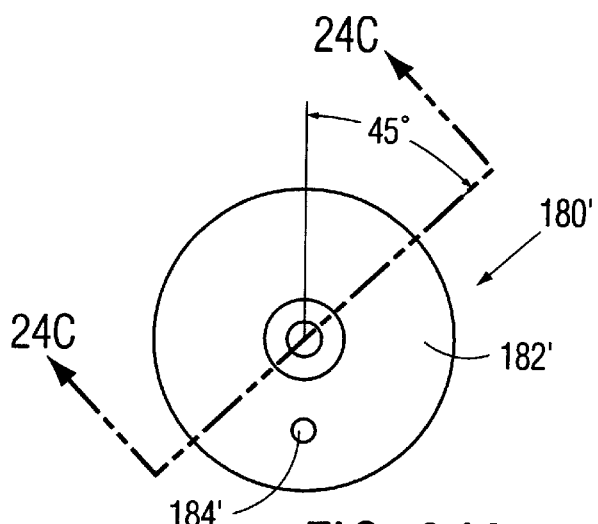
FIG. 24A is a top plan view of a modified metering dose plate.
Figure 24B:
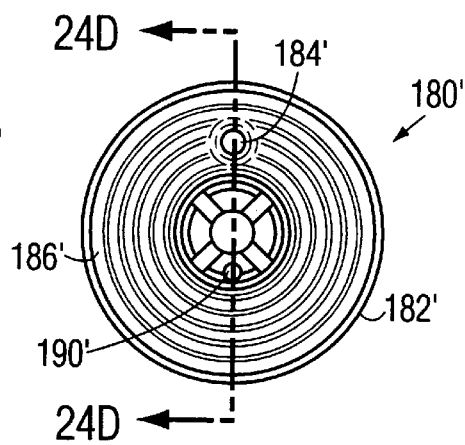
FIG. 24B is a bottom plan view of the metering dose plate of FIG. 24A.
Figure 24C:
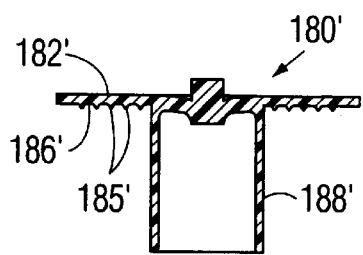
FIG. 24C is a cross-sectional view of the metering dose plate of FIG. 24A, taken along line 24C—24C thereof.
Figure 24D:
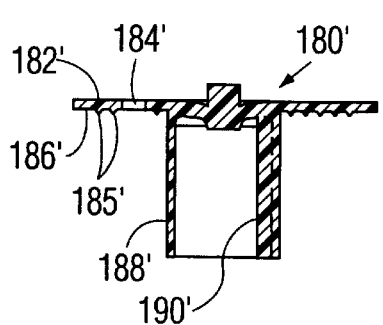
FIG. 24D is a cross-sectional view of the metering dose plate of FIG. 24B, taken along line 24D—24D thereof.
Figures 24E, 24F:
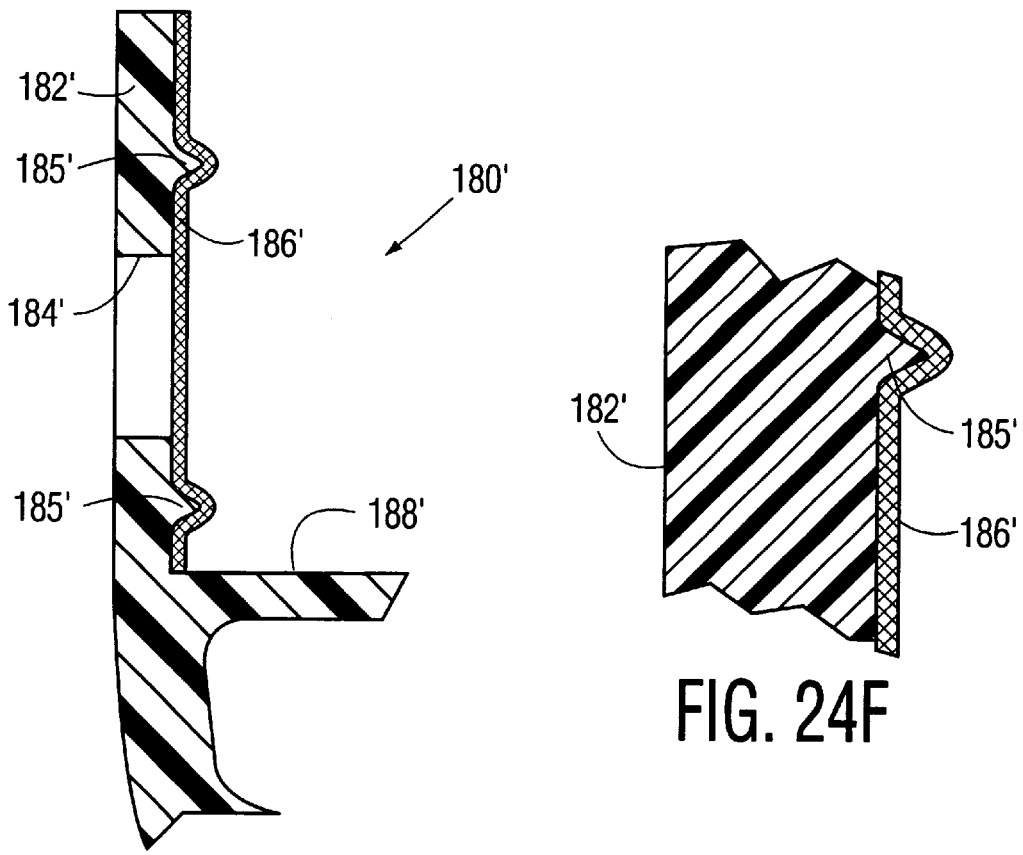
FIG. 24E is an enlarged cross-sectional view of a portion of the metering dose plate of FIG. 22D.
FIG. 24F is an enlarged cross-sectional view of a portion of the metering dose plate of FIG. 22E.
Figure 30:
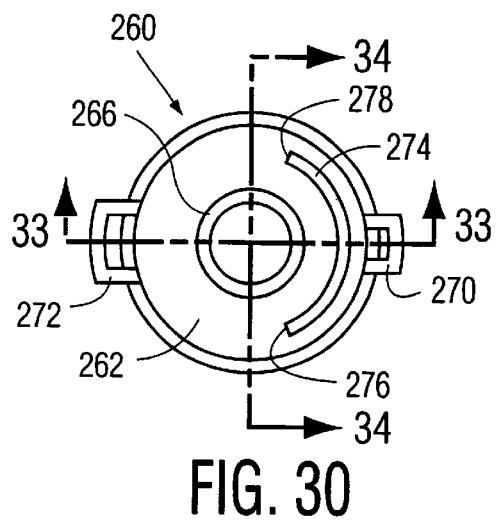
FIG. 30 is a bottom plan view of the lower spring retainer of the metered powder dose dispenser of FIG. 1.
Figure 31:
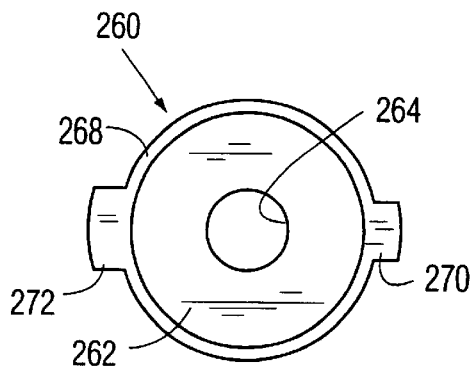
FIG. 31 is a top plan view of the lower spring retainer of FIG. 30.
Figure 32:
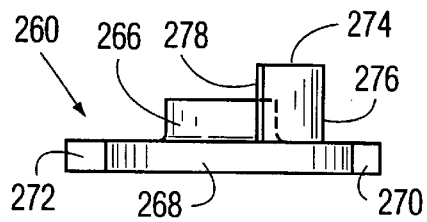
FIG. 32 is a side elevational view of the lower spring retainer of FIG. 30.
Figure 33:
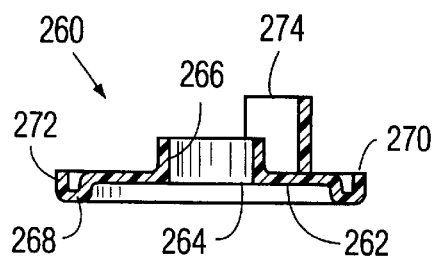
FIG. 33 is a cross-sectional view of the lower spring retainer of FIG. 30, taken along line 33—33 thereof.
Figure 34:
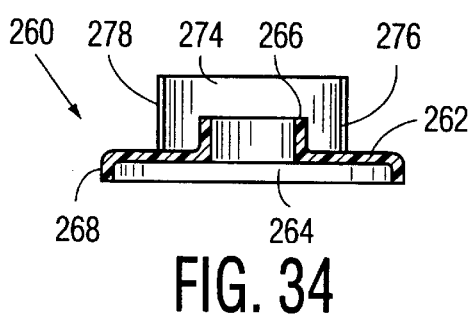
FIG. 34 is a cross-sectional view of the lower spring retainer of FIG. 30, taken along line 34—34 thereof.
Figure 35:
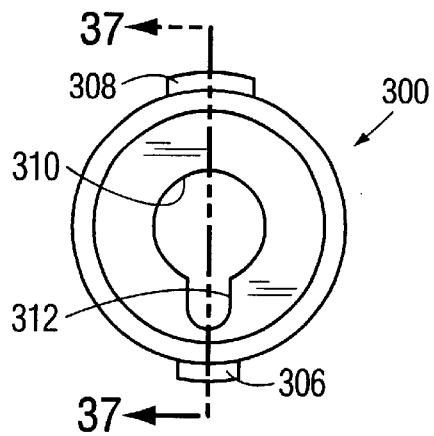
FIG. 35 is a top plan view of the support plate of the metered powder dose dispenser of FIG. 1.
Figure 36:
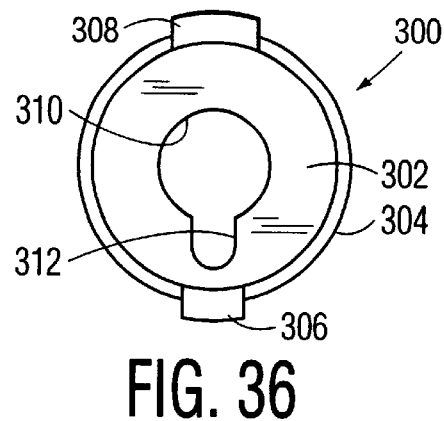
FIG. 36 is a bottom plan view of the support plate of FIG. 35.
Figure 37:
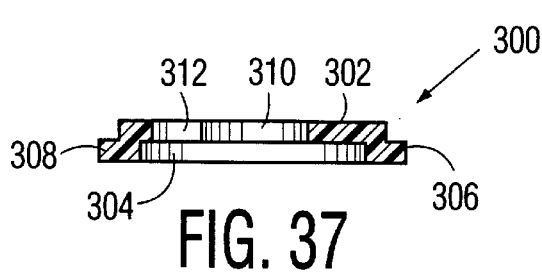
FIG. 37 is a cross-sectional view of the support plate of FIG. 35, taken along line 37—37 thereof.

However, unlike powder retainer 186 of metering dose plate 180, powder retainer 186' is formed along substantially the entire undersurface of disc 182', as shown best in FIG. 24B. Thus, there is no formation of a shallow recess 183 as in disc 182. In this regard, powder retainer 186' has an annular configuration with an outer diameter slightly smaller than the outer diameter of disc 182'.

In order to secure powder retainer 186' to the underside of disc 182', the underside of disc 182' is provided with a plurality of concentric ribs or spikes 185', each having a substantially inverted triangular cross-sectional configuration. With such arrangement, when the mesh screen of powder retainer 186' is positioned on the underside of disc 182', an ultrasonic welding operation is performed. Specifically, ultrasonic energy is directed toward the underside of disc 182'. In such case, the concentric spikes 185' function as energy directors which absorb greater amounts of energy than the remainder of the underside of disc 182'. As a result, the plastic material of spikes 185' is fused into the mesh to secure powder retainer 186' thereat. With this arrangement, there is a uniform energy that is applied for securing powder retainer 186', and an automated operation can be used to perform such securing operation, achieving a consistency at all times.

As with metering dose plate 180, metering dose plate 180' includes an annular mounting post 188' extending downwardly from the lower surface of disc 182' and centrally located thereon. Annular mounting post 188' is formed with a bar 190' extending axially along the inner surface of mounting post 188' in diametric relation to metered dose hole 184'. Bar 190' extends the entire height of mounting post 188', and preferably has a square cross-sectional configuration. As with metering dose plate 180, bar 190' ensures that metering dose plate 180' will remain stationary with respect to powder housing 20 when powder housing 20, which includes reservoir body 22, reservoir plug 90 and driving body 120, is rotated.

In order to provide for this relative rotation, metering dose plate 180 is non-rotatably mounted on, and powder housing 20 is rotatably mounted on, a base 200, shown in FIGS. 3, 4 and 25–29. Base 200 includes a circular top wall 202 having an annular skirt 204 extending downwardly from the periphery thereof. The peripheral edge of circular top wall 202 is cut-away to define an outer annular ledge 206. An annular supporting lip 208 is formed on the outer surface of annular skirt 204 at the lower end thereof, so as to extend outwardly therefrom in the radial direction of annular skirt 204. An annular wall 209 having a diameter less than that of supporting lip 208 is formed at the upper end of supporting lip 208. As shown in FIG. 4, annular wall 209 can have a plurality of axially spaced apart, annular teeth 211 on the outer surface thereof. In addition, an annular retaining rim 210 is formed on the upper, outer surface of annular skirt 204, parallel to supporting lip 208 and annular wall 209, and spaced above annular wall 209, so as to extend outwardly from annular skirt 204 in the radial direction thereof. Retaining rim 210 has a diameter slightly less than the diameter of annular wall 209. Thus, an annular retaining gap 212 is formed between annular wall 209 and retaining rim 210.

Further, a small post 214 is formed, extending upwardly from annular wall 209 to a height above retaining rim 210, but below top wall 202. Post 214 has an outside diameter equal to that of annular wall 209, and also is connected with retaining rim 210 and extends within gap 212.

A cylindrical boss 216 is formed centrally and axially on the upper surface of circular top wall 202, with an upper annular portion 217 thereof partially cut-away and a radial segment 219 thereof also cut away. A coaxial retaining post 218 of lesser diameter than cylindrical boss 216 is formed at the upper end of cylindrical boss 216. Accordingly, an outer annular ledge 220 is formed at the upper edge of cylindrical boss 216. Retaining post 218 has an outer diameter slightly less than the inner diameter of annular mounting post 188 of metering dose plate 180. Retaining post 218 is formed with a slot 222 along the length thereof. Accordingly, due to bar 190 and slot 222, mounting post 188 of metering dose plate 180 is retained on retaining post 218 in a non-rotatable manner to ensure that metering dose plate 180 will remain stationary with respect to powder housing 20 when powder housing 20, which includes reservoir body 22, reservoir plug 90 and driving body 120, is rotated.

Two short stub walls 221 and 223 are formed on the upper surface of top wall 202, immediately on opposite sides of cylindrical boss 216. Stub walls 221 and 223 are angled with respect to each other at an angle of approximately 30 degrees.

As part of a counter mechanism which will be described in greater detail hereinafter, a first rotation prevention spring detent 224 is mounted in a cantilever manner on circular top wall 202. Specifically, a curved vertical detent supporting wall 226 extends upwardly from circular top wall 202 at a position substantially midway between annular ledge 206 and cylindrical boss 216, and first rotation prevention spring detent 224 extends from one edge 228 of detent supporting wall 226, parallel to and spaced above circular top wall 202. Further, the free end of first rotation prevention spring detent 224 is provided with an outward radially directed tab 230 thereat.

Also as part of the counter mechanism which will be described in greater detail hereinafter, a second rotation prevention spring detent 232 is mounted in a cantilever manner on circular top wall 202. Specifically, second rotation prevention spring detent 232 extends from edge 228 of detent supporting wall 226, parallel to and spaced above circular top wall 202 and parallel to and spaced above first rotation prevention spring detent 224. The free end of second rotation prevention spring detent 232 is provided with an outward radially directed tab 234.

A triangular shaped sectored recess 236 is formed in circular top wall 202 in correspondence with detents 224 and 232, and diametrically opposite to post 214. Specifically, recess 236 includes a first radial boundary 240 substantially in line with the connected end of detent 232, and a second boundary 242 extending in alignment with the lengthwise direction of detent 232.

Further, a shallow recess 243 is provided at the outer radial edge of annular ledge 206, in alignment with sectored recess 236, and diametrically opposite post 214.

In order to spring bias metering dose plate 180 into engagement with the lower surface of thin circular plate 92 of reservoir plug 90 and to ensure that powder 92 can only be inhaled when metered dose hole 184 is in alignment with venturi conduit 64, a biasing assembly is provided.

The biasing assembly includes a lower spring retainer 260 mounted on annular ledge 220, over retaining post 218, as shown in FIGS. 3, 4 and 30–34. Specifically, lower spring retainer 260 includes a disc 262 having a central opening 264 sized to receive retaining post 218. An annular boss 266 extends from the lower surface of disc 262 in surrounding relation to central opening 264. When retaining post 218 extends through annular boss 266 and central opening 264, the lower edge of annular boss 266 seats upon annular ledge 220.

All upper annular retaining lip 268 extends upwardly from the peripheral edge of disc 262. Further, two radially extending driven ears 270 and 272 are formed in diametrically opposite positions at the peripheral edge of annular lip 268. Ear 270 has a width substantially equal to the width of drive slot 34 of reservoir body 22 so as to fit therein and be driven thereby, and ear 272 has a width substantially equal to the width of drive slot 36 of reservoir body 22 so as to fit therein and be driven thereby.

Further, an arcuate pawl driving wall 274 extends from the lower surface of disc 262 between annular boss 266 and the periphery of disc 262, for an arcuate distance of approximately 79°. Pawl driving wall 274 includes opposite pawl driving ends 276 and 278, as will be described in greater detail hereinafter with reference to the counter mechanism.

The biasing assembly further includes a coil spring 290 having one end seated on the upper surface of disc 262 of lower spring retainer 260, and restrained thereon by annular retaining lip 268.

As shown in FIGS. 3, 4 and 35–37, the biasing assembly further includes a support plate 300 which supports metering dose plate 180, functions as an upper spring retainer, biases metering dose plate 180 against the lower surface of thin circular plate 92 of reservoir plug 90, and permits suction through metered dose hole 184 only when metered dose hole 184 is in alignment with venturi conduit 64.

Specifically, support plate 300 is formed by a disc 302 having an annular retaining lip 304 extending downwardly from the peripheral edge of disc 302.

Two radially extending driven ears 306 and 308 are formed in diametrically opposite positions at the peripheral edge of annular lip 304. Ear 306 has a width substantially equal to the width of drive slot 34 of reservoir body 22 so as to fit therein and be driven thereby, and ear 308 has a width substantially equal to the width of drive slot 36 of reservoir body 22 so as to fit therein and be driven thereby. The height of ears 306 and 308 is less than the height of annular lip 304, and lower surfaces of ears 306 and 308 are substantially flush with the lower edge of annular lip 304, although the invention is not so limited.

In addition, a central circular hole 310 is formed in disc 302 and is sized to rotatably receive annular mounting post 188 of metering dose plate 180 therein. A radially extending slot 312 extends from and is in communication with circular hole 310. Slot 312 extends outwardly in the radial direction by a distance such that the radially outer part of slot 312 overlaps metered dose hole 184 when metered dose hole 184 is in alignment with venturi conduit 64, and is out of alignment with, and thereby does not overlap, metered dose hole 184 at all other times.

Figure 38:
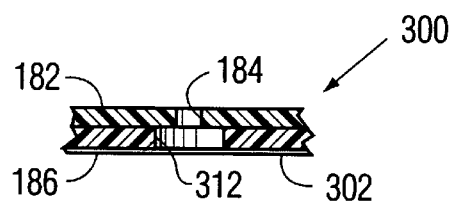
FIG. 38 is a cross-sectional view of a portion of the metering dose plate, support plate and powder retainer according to an alternative embodiment of the present invention.

As described above, powder retainer 186 is formed by a mesh screen, filter, porous material or the like which has a minimal restrictive effect on gas flow therethrough. However, when a mesh screen or the like is used, there is a reduction in gas flow, and thereby of any suction by the user, of approximately 35%. According to an alternative embodiment, as shown in FIG. 38, powder retainer 186 comprised of a mesh screen or the like can be relocated to the lower surface of disc 302 of support plate 300, under slot 312. Therefore, although the mesh screen or the like reduces the gas flow through radially extending slot 312, this does not effectively restrict the gas flow through metered dose hole 184 which is smaller than slot 312. Thus, primary air flow is independent of the cross-sectional width of metering dose plate 180. Further, there is no mesh powder retainer 186 at metered dose hole 184 to reduce air flow through metered dose hole 184.

Figure 39:
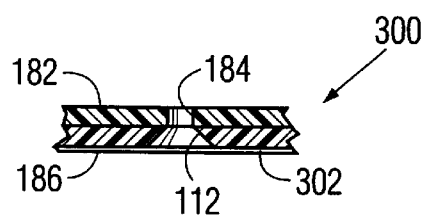
FIG. 39 is a cross-sectional view of a portion of the metering dose plate, support plate and powder retainer according to another alternative embodiment of the present invention.
Figure 40:
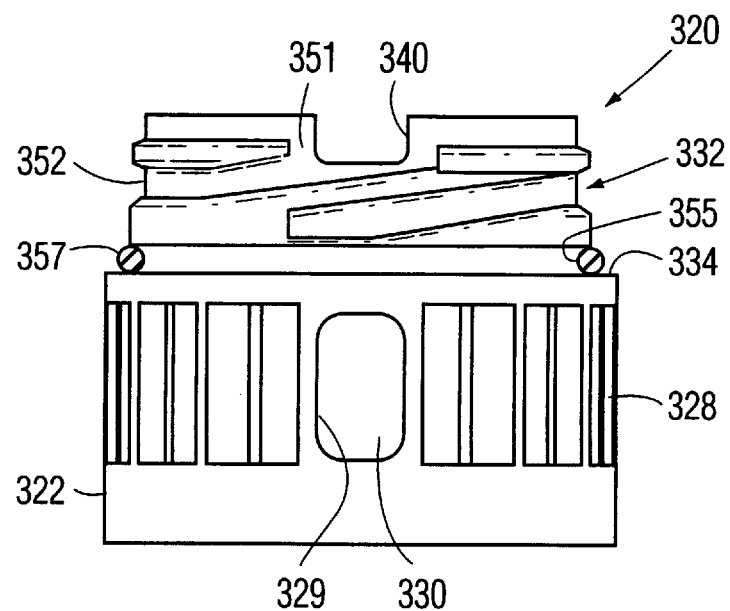
FIG. 40 is a front elevational view of the adapter of the metered powder dose dispenser of FIG. 1.
Figure 41:
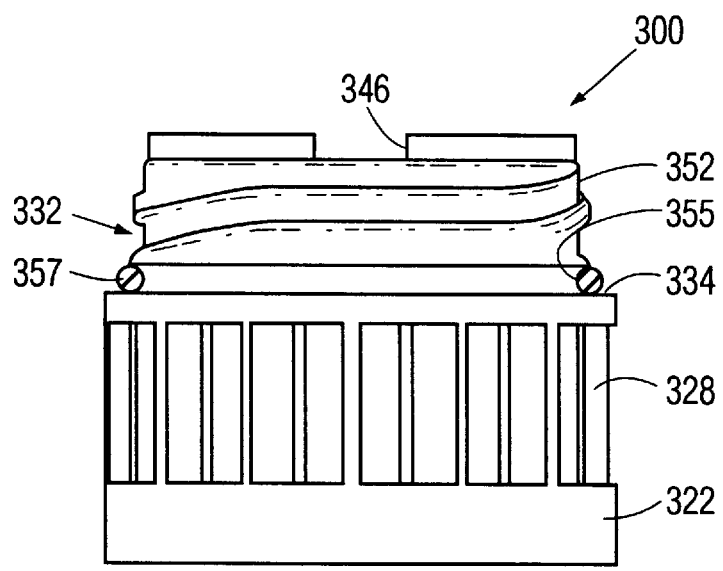
FIG. 41 is a side elevational view of the adapter of FIG. 40.
Figure 42:
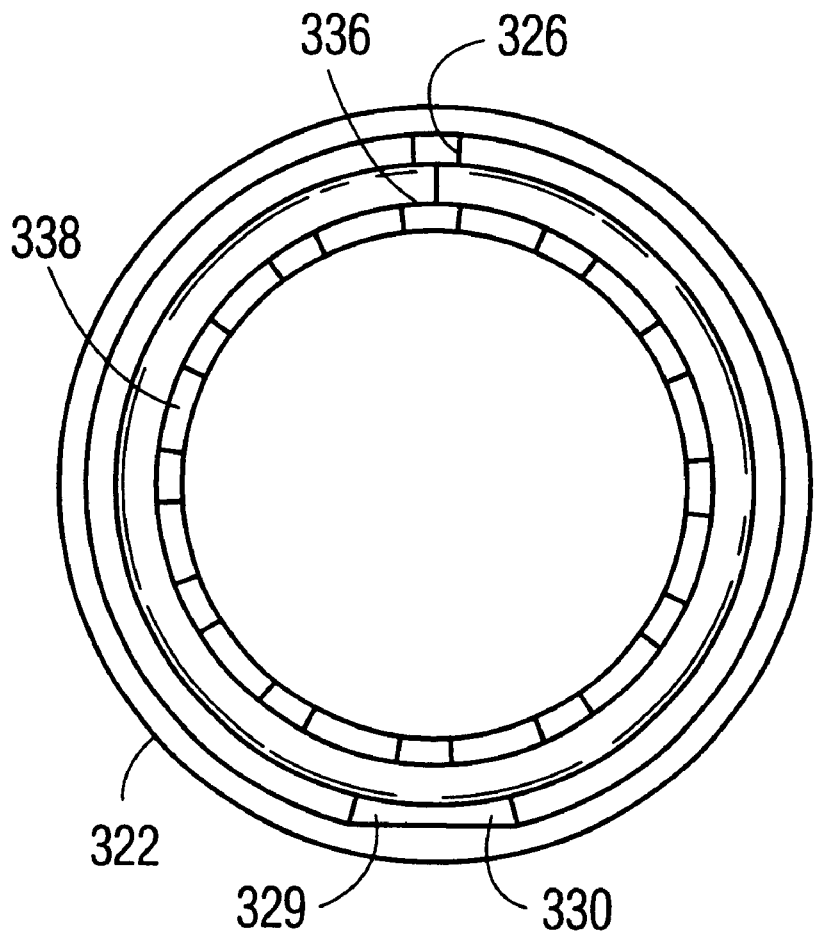
FIG. 42 is a bottom plan view of the adapter of FIG. 40.

As shown in FIG. 39, which is an alternative embodiment of the arrangement of FIG. 38, slot 312 in support plate 300 is angled at opposite sides thereof in a downwardly diverging manner. With such arrangement, the air flow cross-sectional area at the bottom of slot 312 can be made greater than four times the air flow cross-sectional area of metered dose hole 184.

It will be appreciated from the above description that metering dose plate 180 is held stationary on base 200, due to bar 190 and slot 222. Further, powder housing 20, comprised of reservoir body 22, reservoir plug 100 and driving body 120, is rotatably mounted with respect to base 200 and metering dose plate 180.

In addition, support plate 300 is biased into engagement with the lower surface of metering dose plate 180 so as to support the same. In the operation, radially extending slot 312 is in alignment with metered dose hole 184 only when metered dose hole 184 is in alignment with venturi conduit 64. Thus, any powder 62 within metered dose hole 184 when metered dose hole 184 is out of alignment with venturi conduit 64 is sandwiched in metered dose hole 184 by mesh powder retainer 186 and the upper surface of disc 302 of support plate 300 at its lower end, and by the lower surface of thin circular plate 92 of reservoir plug 90 at its upper end. As will be discussed in greater detail hereinafter, in the stored or inactive position of metered powder dose dispenser 10, metered dose hole 184 is primed, and is positioned diametrically opposite to radially extending slot 312. In such position, powder 62 within metered dose hole 184 is held between the upper surface of disc 302 of support plate 300 and the lower surface of thin circular plate 92 of reservoir plug 90, and therefore cannot escape metered dose hole 184.

In order to positively hold all of the above elements together, metered powder dose dispenser 10 further includes an adapter 320, as shown in FIGS. 3, 4 and 40–45. As shown therein, adapter 320 includes a lower annular wall 322 having an inner diameter larger than the outer diameter of lower annular skirt section 30 of reservoir body 22 so as to easily fit thereover. The inner diameter of lower annular wall 322 is also slightly larger than the outer diameter of annular skirt 204 of base 200 so as to fit thereover, but slightly less than the outer diameter of annular retaining rim 210 of base 200.

An annular groove 324 is formed at the inner, lower end of lower annular wall 322, slightly spaced above the lower edge thereof. Accordingly, due to the resilience of the plastic pieces, when adapter 320 is inserted over base 200 and pushed down thereon, retaining rim 210 of base 200 snaps into annular groove 324 to hold adapter 320 on base 200. At such time, annular teeth 211 can engage the inner surface of lower annular wall 322, as shown in FIG. 4.

In order to obtain and maintain correct alignment between adapter 320 and base 200, adapter 320 is provided with a small slot 326 within groove 324. Slot 326 has a width substantially equal to that of small post 214 in base 200 so as to receive the same therein. Of course, it will be appreciated that post 214 can be provided in adapter 320 and slot 326 can be provided in base 200, that is, with a reversal of parts. Thus, rotation of adapter 320 causes base 200 to rotate therewith.

The outer surface of lower annular wall 322 is preferably provided with a gripping surface 328 formed by undulations, knurling or the like, to enhance the gripping and rotation of metered powder dose dispenser 10.

A rectangular opening 329 is formed in lower annular wall 322, substantially diametrically opposite to slot 326, and substantially centrally along the height of lower annular wall 322. Opening 329 is formed by a large inner opening portion 329a and a contiguous outer opening portion 329b of smaller dimensions, so as to form a rectangular shoulder 329c. A rectangular transparent plastic window 330 is fixed in opening 329 and includes a central window portion 330a which fits snugly within outer opening portion 329b and a large inner securing portion 330b of larger dimensions that fits within large inner opening portion 329a and is secured to rectangular shoulder 329c by an adhesive, welding or the like. Window 330 is used with the counter mechanism which will be described in greater detail hereinafter.

Adapter 320 further includes an upper annular wall 332 of a lesser diameter than lower annular wall 322, and connected to the upper end of lower annular wall 322 by an outer annular shoulder 334.

An annular biasing lip 338 is formed on the inner surface of upper annular wall 332. When adapter 320 is pushed down so as to lock adapter 320 onto base 200, as described above, annular biasing lip 338 seats on outer annular shoulder 32 of reservoir body 22, and thereby biases reservoir body 22 down against the force of coil spring 290. Accordingly, coil spring 290 is compressed so that a biasing force always forces support plate 300 into abutment with metering dose plate 180, and always forces metering dose plate 180 into abutment with reservoir plug 90. However, such biasing action still permits rotation of reservoir body 22 relative to adapter 320 and metering dose plate 180.

At the same time, this compression ensures that driven ears 270 and 306 will always be located within drive slot 34 and driven ears 272 and 308 will always be located within drive slot 36, so that rotation of reservoir body 22 will cause consequent rotation of lower spring retainer 260 and support plate 300. Because metering dose plate 180 is held stationary on base 200, due to bar 190 and slot 222, powder housing 20 (comprised of reservoir body 22, reservoir plug 90 and driving body 120), lower spring retainer 260 and support plate 300, are rotatably mounted with respect to base 200, metering dose plate 180 and adapter 320.

In the assembled condition discussed above, the lower edge of lower annular skirt section 128 of driving body 120 rests and rotates on the upper edge of upper annular wall 332 of adapter 320. In order to provide air flow through metered dose hole 184 of metering dose plate 180, two diametrically opposite recesses 340 and 342 are formed in upper annular wall 332, extending from the upper edge of upper annular wall to annular biasing lip 338. Recess 340 has a width identical to the width of drive slot 34, while recess 342 has a width identical to the width of drive slot 36. When metered dose hole 184 is aligned with venturi conduit 64 of reservoir body 22 and with radially extending slot 312 of support plate 300, recess 340 is in alignment with drive slot 34 and recess 342 is in alignment with drive slot 36. Accordingly, suction on venturi conduit 64 causes air to flow through recess 340 and drive slot 34 and through recess 342 and drive slot 36, and then through radially extending slot 312, metered dose hole 184 and venturi conduit 64 to deliver the metered dose of powder 62 in metered dose hole 184, to a user of dispenser 10.

In addition, two diametrically opposite recesses 344 and 346 are formed in upper annular wall 332, extending from the upper edge of upper annular wall to a position slightly above annular biasing lip 338. Recesses 344 and 346 are shallower than recesses 340 and 342, and are oriented to be 90 degrees offset from recesses 340 and 342 such that recesses 340–346 are equiangularly arranged about upper annular wall 332. As will be made apparent from the discussion hereinafter, recesses 344 and 346 are intended to receive spring fingers 163 and 165 to lock the assembly in position after the cap has been removed.

Figure 43:
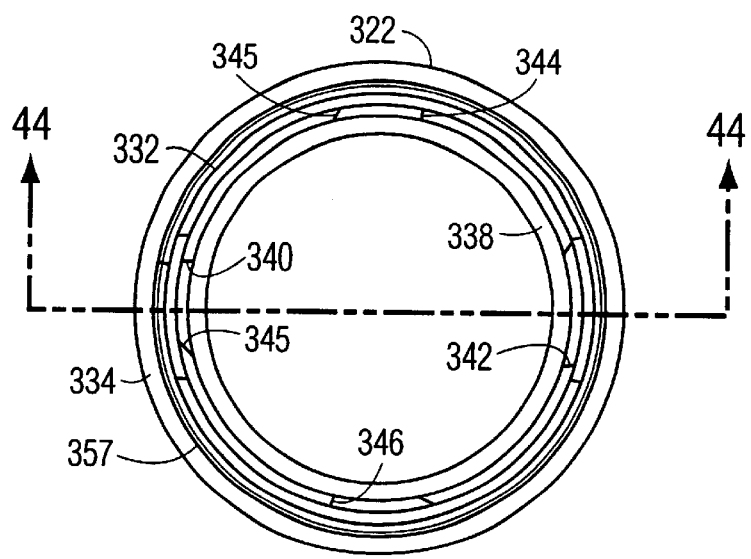
FIG. 43 is a top plan view of the adapter of FIG. 40.
Figure 44:
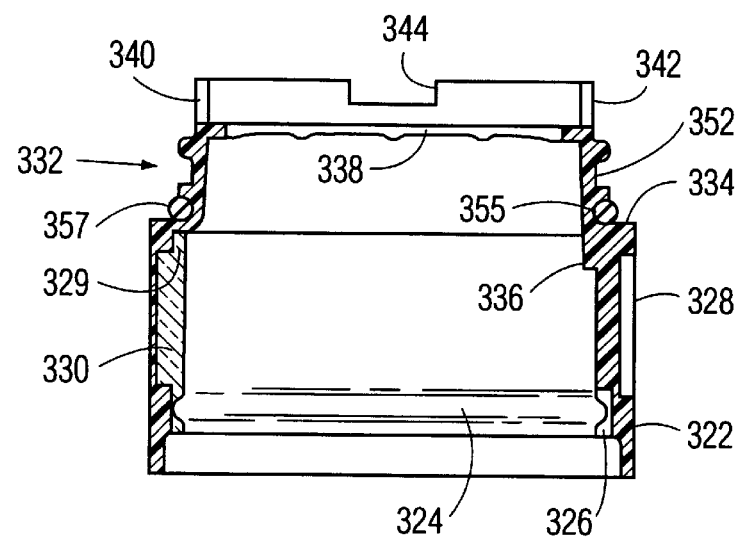
FIG. 44 is a cross-sectional view of the adapter of FIG. 43, taken along line 44—44 thereof.
Figure 45:
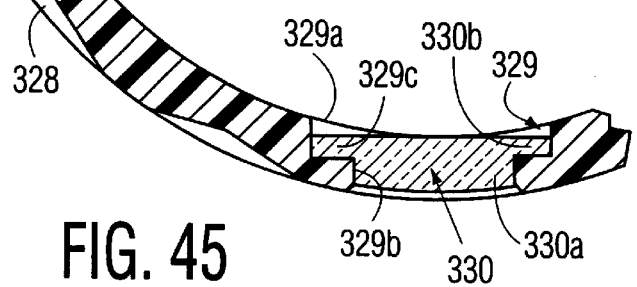
FIG. 45 is an enlarged cross-sectional view of a portion of the adapter of FIG. 41, showing the window thereof.
Figure 46A:
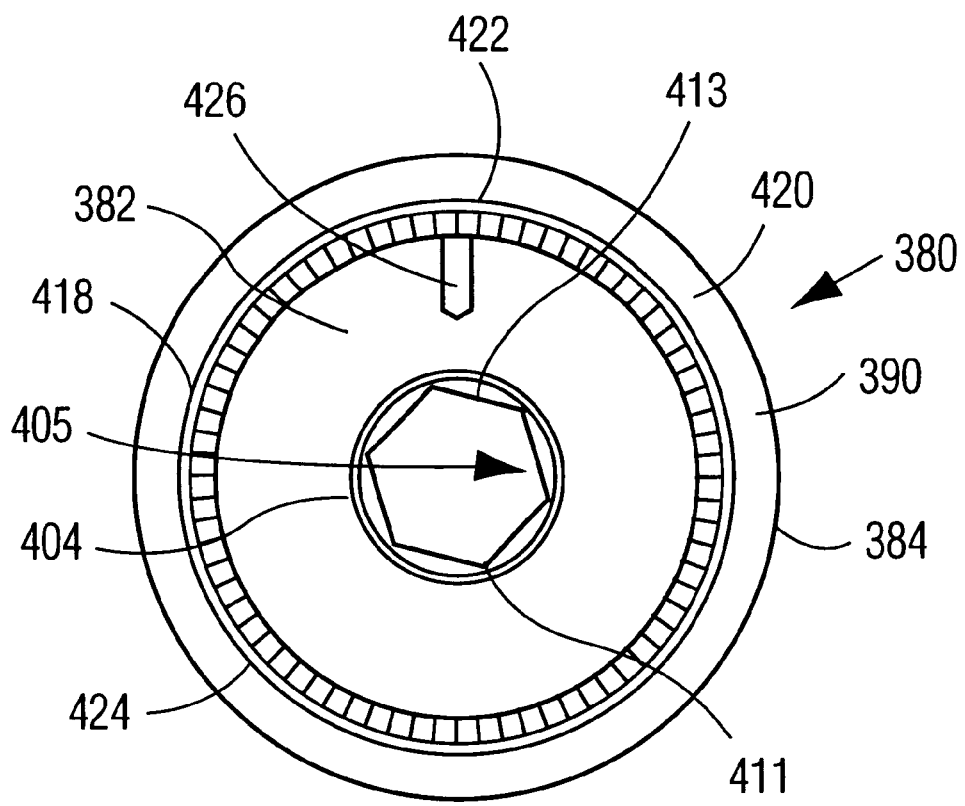
FIG. 46 is a top plan view of the swirl nozzle of the metered powder dose dispenser of FIG. 1.
Figure 46:
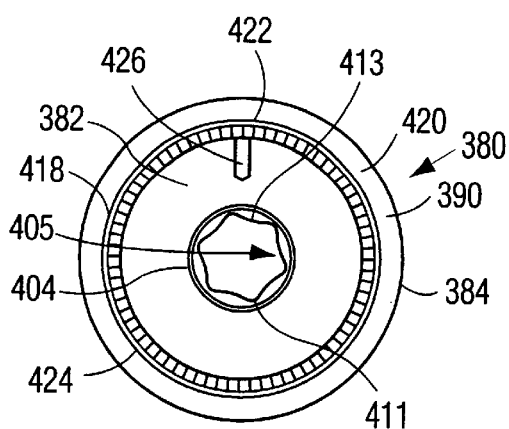

As shown in the top view of FIG. 43, recesses 340, 342, 344 and 346 each have one side thereof with a bevel 345 toward the inside surface thereof, the purpose for which will become apparent hereinafter.

A double helical cam track 352 is formed on the outer surface of upper annular wall 332, the purpose for which will become apparent from the description which follows. As is apparent, the walls 353 that form double helical track 352 have a substantially square cross-section, the purpose for which will become apparent from the discussion hereinafter with respect to the cap. Further, the entry 351 to each cam track 352 is formed as a vertical drop zone before rotation can begin, thus ensuring accurate registry of the closure cap and thereby, accurate operation of dispenser 10, as shown best in FIGS. 40, 89B and 89C.

Lastly, the lowermost walls 353 have a common lowermost surface that extends in a horizontal plane, and together with outer annular shoulder 334, form an annular groove 355 therebetween for seating an O-ring 357 therein. Such O-ring 357 provides a vapor seal.

In order to ensure that the powder is de-agglomerated and properly mixed with the suction air from the open upper end of upper venturi conduit section 68 of venturi conduit 64, a swirl nozzle 380, as shown in FIGS. 46–50, is mounted to the upper end of reservoir body 22. Air which contains agglomerated powder particles flows from upper venturi conduit section 68 into the swirl nozzle. Mechanical de-agglomeration is an important function of the swirl nozzle.

Swirl nozzle 380 includes a circular top wall 382 and an annular side wall 384 extending downwardly from the periphery of top wall 382. Annular side wall 384 has an outer diameter substantially equal to the outer diameter of upper annular skirt section 126 of driving body 120. Further, the inner connecting region 386 between circular top wall 382 and annular side wall 384 is curved to provide a smooth transition therebetween and thereby to provide a smooth flow path for powder 62. In other words, the inner area defined by circular top wall 382, annular side wall 384 and inner connecting region 386 has a somewhat partial toroidal configuration. The outer connecting region 390 therebetween, however, forms a substantially right angle in cross-section between circular top wall 382 and annular side wall 384.

In order to secure swirl nozzle 380 onto the upper end of driving body 120, and particularly, onto annular retaining ledge 159 of driving body 120, four spiked ribs 392, 393, 394 and 396 are equiangularly formed extending down from the lower edge of annular side wall 384. Spiked ribs 392, 393, 394 and 396 extend arcuate distances which are different from each other and which correspond identically with the arcuate distances of arcuate recesses 158a–158d, respectively, of driving body 120 so that swirl nozzle 380 is assembled at a predetermined position with driving body 120. For example, spiked ribs 392 and 394 can extend for an arcuate distance of 36 degrees; spiked rib 393 for an arcuate distance of 40 degrees; and spiked rib 396 for an arcuate distance of 44 degrees. Spiked ribs 392, 393, 394 and 396 extend along a common circle having a diameter equal to the common circle around which recesses 15a–158d extend. Thus, spiked ribs 392, 393, 394 and 396 extend within recesses 15a–158d, respectively, with a two degree adjustment clearance. Preferably, each spiked rib 392, 393, 394 and 396 has a tapered end with a substantially triangular cross-sectional configuration.

Figure 50A:
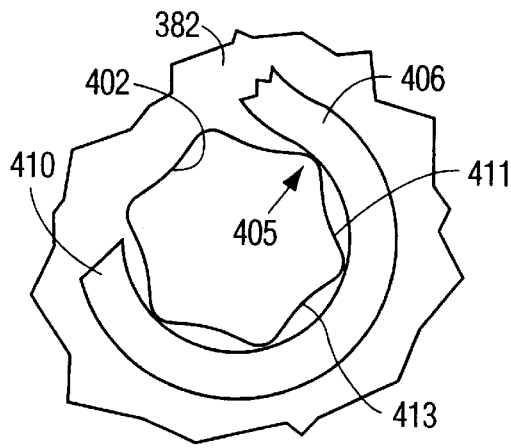
FIG. 50A is an enlarged bottom plan view of the center of swirl nozzle of FIG. 46.
Figure 50B:
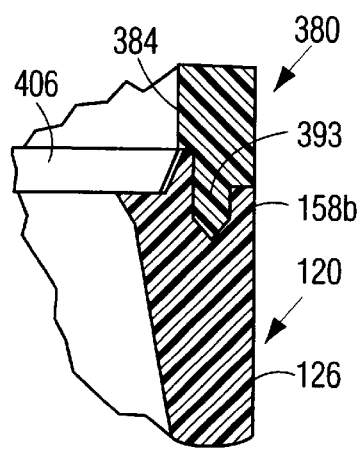
FIG. 50B is a cross-sectional view showing securement of the swirl nozzle to the driving body.
Figure 51:
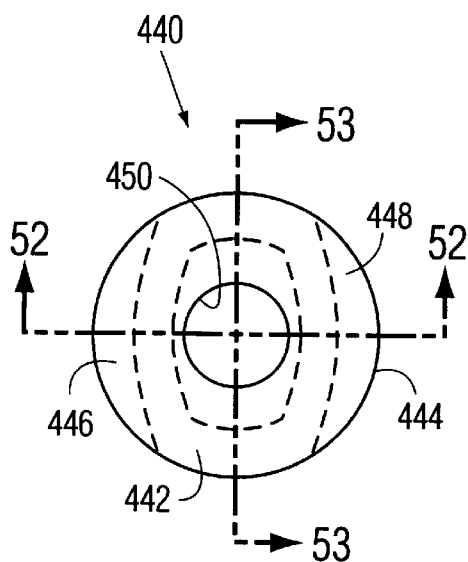
FIG. 51 is a top plan view of the mouthpiece of the metered powder dose dispenser of FIG. 1.
Figure 52:
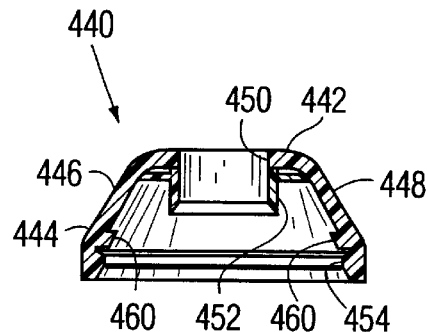
FIG. 52 is a cross-sectional view of the mouthpiece of FIG. 51, taken along line 52—52 thereof.
Figure 53:
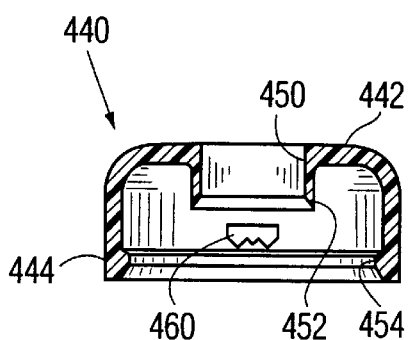
FIG. 53 is a cross-sectional view of the mouthpiece of FIG. 51, taken along line 53—53 thereof.
Figure 54:
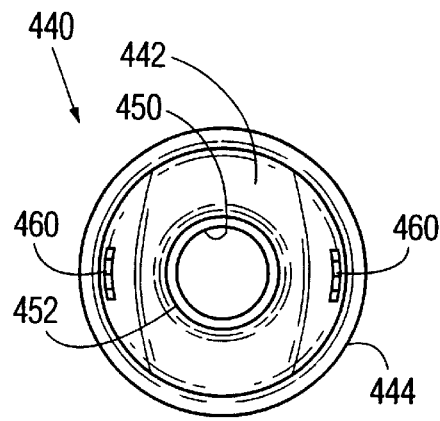
FIG. 54 is a bottom plan view of the mouthpiece of FIG. 51.
Figure 55:
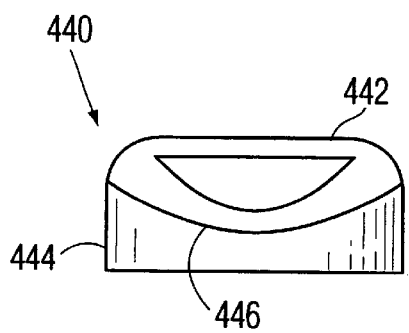
FIG. 55 is a side elevational view of the mouthpiece of FIG. 51.
Figure 56:
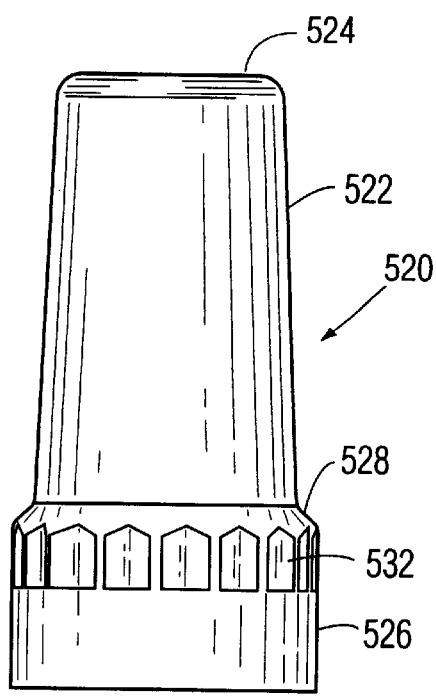
FIG. 56 is a side elevational view of the closure cap of the metered powder dose dispenser of FIG. 1.
Figure 57:
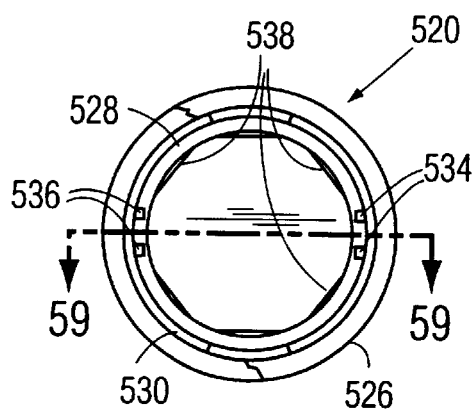
FIG. 57 is a bottom plan view of the closure cap of FIG. 56.
Figure 58:
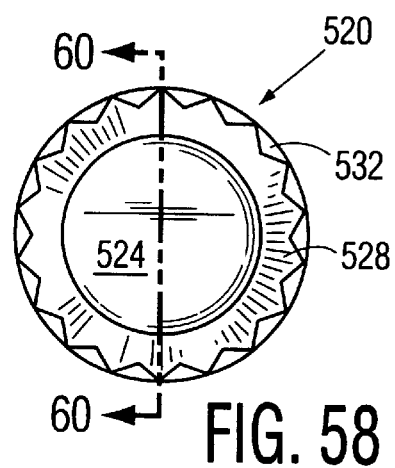
FIG. 58 is a top plan view of the closure cap of FIG. 56.
Figure 59:
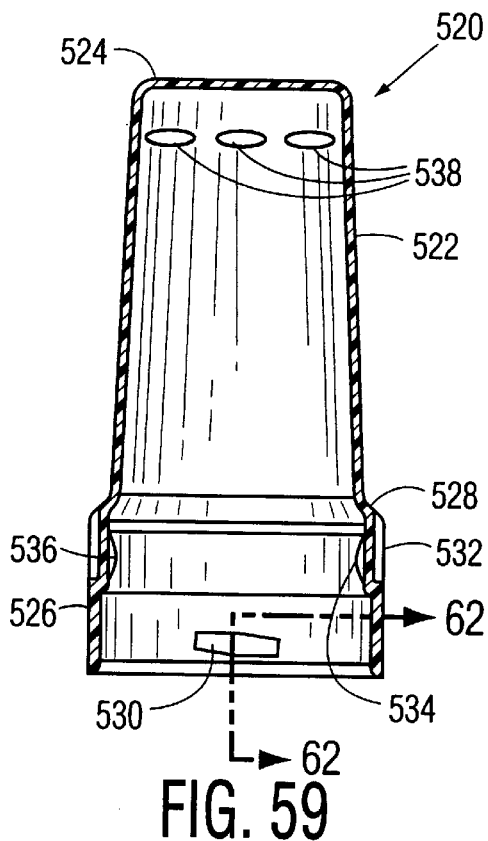
FIG. 59 is a cross-sectional view of the closure cap of FIG. 57, taken along line 59—59 thereof.
Figure 60:
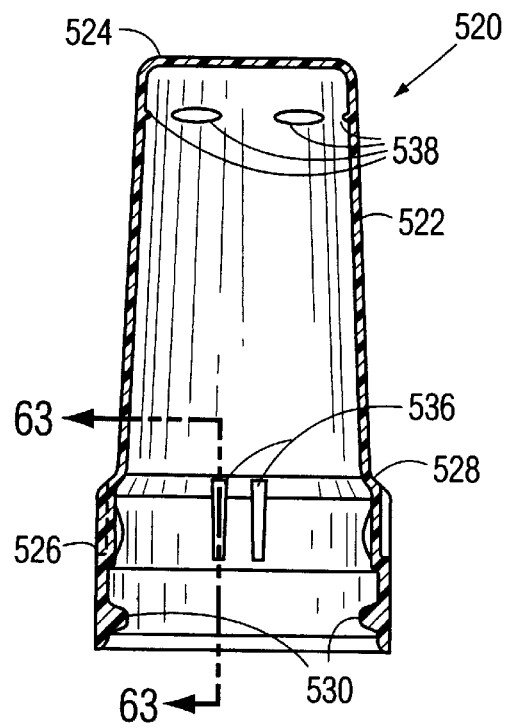
FIG. 60 is a cross-sectional view of the closure cap of FIG. 58, taken along line 60—60 thereof.
Figure 61:
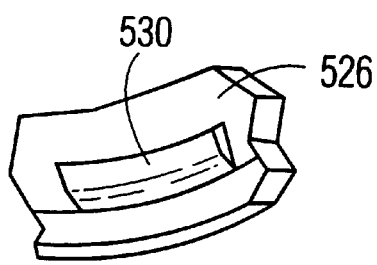
FIG. 61 is a perspective view of a lower inner portion of the closure cap of FIG. 56, showing one cam thereon.
Figure 62:
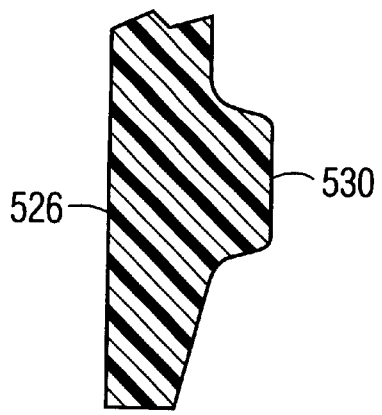
FIG. 62 is a cross-sectional view of the closure cap of FIG. 59, taken along line 62—62 thereof.
Figure 63:
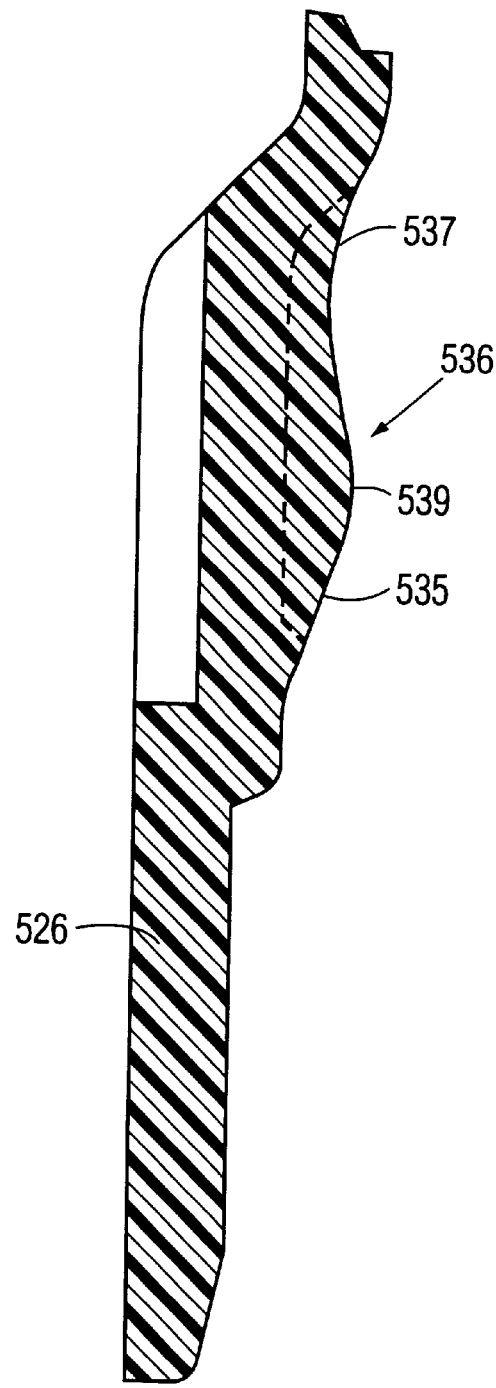
FIG. 63 is a cross-sectional view of the closure cap of FIG. 60, taken along line 63—63 thereof.

During an inhalation process, swirl nozzle 380 and the mouthpiece (discussed later) secured thereto might detach from driving body 120 and be swallowed. Therefore, in order to fixedly secure swirl nozzle 380 onto driving body 120, an ultrasonic welding operation is performed. Specifically, ultrasonic energy is directed toward spiked ribs 392, 393, 394 and 396. In such case, the spiked or sharp ends of ribs 392, 393, 394 and 396 function as energy directors which absorb greater amounts of energy. As a result, the plastic material of spiked ribs 392, 393, 394 and 396 is fused into the plastic material of recesses 15a–158d to secure swirl nozzle 380 on driving body 120, as shown in FIG. 50B. With this arrangement, there is a uniform energy that is applied for securing swirl nozzle 380, and an automatic operation can be used to perform such securing operation, achieving a consistency at all times.

It will be appreciated that, in such position, first and second outer air passages 150 and 152 extend inwardly of annular side wall 384 to supply secondary air flow thereto which mixes with the air/powder mixture from venturi conduit 64 which is also supplied to the interior of annular side wall 384.

Circular top wall 382 has a central opening 402, and a supply chimney 404 is formed on the upper surface of circular top wall 384 in surrounding relation to central opening 402.

In order to break up the powder agglomerates, prior to supplying the same through supply chimney 404, a curved spiral-like wall 406 extends downwardly from circular top wall 382 and is connected at one end 408 to annular side wall 384. Specifically, curved wall 406 extends in a curvilinear manner from end 408, and partially about central opening 402 to an opposite end 410. Thus, a gap 409 is provided between end 410 and the remainder of curved wall 406. The height of curved wall 406 is equal to that of annular side wall 384 so that the lower edge of curved wall 406 sits on circular top wall 122 of driving body 120 when swirl nozzle 380 is assembled with driving body 120, as described above. Curved wall 406 is effectively formed in two sections, namely, a first section starting from end 410 and extending partially about central opening 402, for example, for 165°, and a second section extending from the end of the first section to end 408 along a larger radius than the first section. With respect to the direction of the radius to the center of venturi conduit 64, the second section preferably leaves or disengages from central opening 402 at an angle of approximately 15° parallel to such radius line, regardless of the size of swirl nozzle 380.

As will be appreciated, curved wall 406 defines a swirl cavity 412, such that the powder from venturi conduit 64 enters swirl cavity 412 and continuously changes direction as it increases in velocity, prior to entering supply chimney 404. Thus, the powder agglomerates constantly impact against circular top wall 382, annular side wall 384 and curved wall 406 within swirl cavity 412. Further, the agglomerates collide with each other which results in a mutual grinding or shattering action between the agglomerates. At the same time, secondary air flow from first and second outer air passages 150 and 152 enters swirl cavity 412, as indicated by arrows 414 and 416, respectively, to accelerate movement of the powder agglomerates in swirl cavity 412. The constant impacts of the powder agglomerates on the walls defining swirl cavity 412 cause the agglomerates to break up into micronized powder upon impact. Basically, as long as the powder agglomerates travel with sufficient velocity, there will be sufficient kinetic energy to break up the agglomerates.

Further, rather than providing a merely helical path along the axial direction of a nozzle, as in the prior art, curved wall 406 and, particularly, swirl cavity 412, first changes the direction of powder 62 from an axial direction of venturi conduit 64 to a transverse direction substantially perpendicular to the axial direction. In this transverse direction, powder 62 is then forced to continuously change direction in the transverse direction of swirl cavity 412. Upon exiting swirl cavity 412, the direction of powder 62 is again changed to an axial direction through supply chimney 404, while retaining a swirl component of the flow, that is, while swirling spirally through chimney 404. Since the micronized powder and any remaining agglomerates maintain the swirl imparted thereto from swirl cavity 412, the swirling flow applies a centrifugal force to the micronized powder and remaining agglomerates, creating additional impacts in supply chimney 404 so as to result in further breaking up of the remaining agglomerates.

Most of the agglomerate break-up should take place, however, in swirl cavity 412. The velocity attained by an agglomerate depends on the drag or suction force, the inertia of the agglomerate, and the length of swirl cavity 412, that is, the time the drag force acts on the agglomerate. Because of its inertia, the agglomerate impacts a wall in swirl cavity 412 to convert the same to micronized powder.

In addition, with the present invention, chimney 404 is provided with vertically oriented grooves or flutes 405 extending along the inner wall thereof. Flutes 405 provide more surfaces against which the agglomerates can impact against. Flutes 405 are shown as being formed by six vertical concave wall sections 411 of a first radius, which are interconnected by six vertical concave wall sections 413 of a larger radius, or even of a flat, planar configuration, that is, infinite radius. However, any other suitable arrangement can be provided. It is preferable, however, that whatever arrangement is provided, flutes 405 or any other configuration are vertically oriented, and thereby provide an irregular vertically oriented surface. Further, as shown, flutes 405 preferably extend from the upper edge of chimney 404 to the upper edge of curved wall 406, although the present invention is not so limited.

Flutes 405 aid in the break-up of agglomerates that require greater de-agglomeration forces to disperse.

Experiments have shown that fluted swirl nozzle 380 increases the respirable fraction over a similar swirl nozzle which is not fluted. Specifically, for hard agglomerates, such as those having a bulk density in the range of 0.29–0.36 g/ml, the same swirl nozzle without flutes provided approximately a 10% respirable fraction, while a fluted swirl nozzle provided approximately a 35% respirable fraction. "Respirable fraction" for purposes of these experiments is the percentage of total particles delivered from the nozzle that are less than or equal to 6.8 micrometers in diameter, as determined using a multi-stage liquid impinger. In the experiments, the formulation was mometasone and lactose agglomerates in a component weight ratio of 1 to 5.8.

Figure 47:
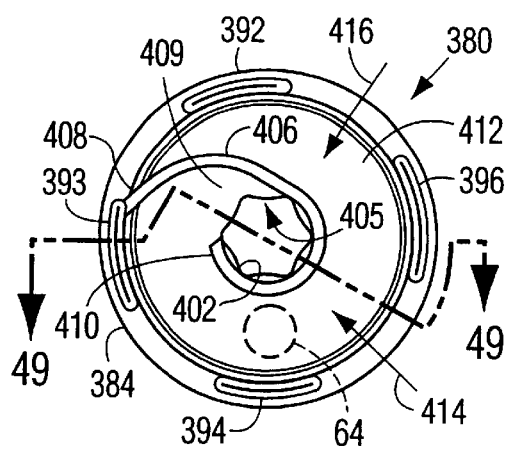
FIG. 47 is a bottom plan view of the swirl nozzle of FIG. 46.
Figure 48:
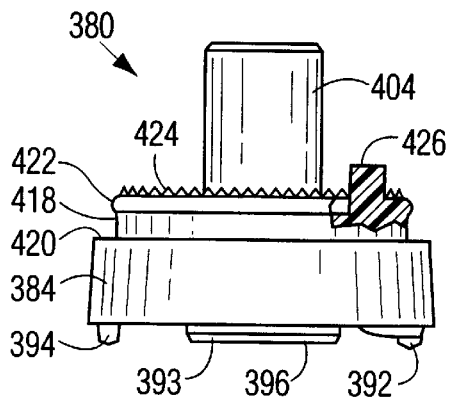
FIG. 48 is a side elevational view of the swirl nozzle of FIG. 46.
Figure 49:
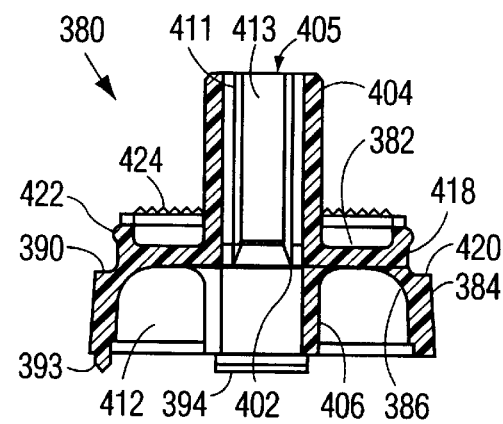
FIG. 49 is a cross-sectional view of the swirl nozzle of FIG. 47, taken along line 49—49 thereof.

In addition to breaking up agglomerates, swirl nozzle 380 must meet additional constraints. For example, the pressure drop through the powder inhaler should desirably be lower than about 20 inches of a water column (5 Kpa) for ease of use by persons with impaired respiratory function, yet sufficiently high to permit significant primary air flow through metered dose hole 184. The pressure drop through swirl nozzle 380 can be changed by varying the angle between end 410 and the position where the first and second sections of curved wall 406 meet, that is, where the second section leaves central opening 402, as shown in FIG. 47. In a presently preferred embodiment, this angle is about 1650, although this value may change depending upon the required pressure drop.

Further, an annular mouthpiece securing wall 418 is formed on the upper surface of circular top wall 382, spaced slightly inwardly from the peripheral edge thereof. As a result, an annular ledge 420 is formed on the upper surface of circular top wall 382, outwardly of annular mouthpiece securing wall 418. Further, an annular lip 422 extends outwardly in the radial direction from the upper end of annular mouthpiece securing wall 418.

Also, gear teeth 424 are provided on the upper edge of annular mouthpiece securing wall 418. Although forty gear teeth are shown, the present invention is not so limited.

Finally, a locator tab 426 is provided on the upper surface of circular top wall 382, along the inner surface of gear teeth 424, diametrically opposite the location of venturi conduit 64 in the final assembled condition of the inhaler.

A mouthpiece 440, as shown in FIGS. 3, 4 and 51–55, is secured to the upper end of swirl nozzle 380. Mouthpiece 440 includes a generally rectangular top wall 442 with an annular side wall 444 depending downwardly from the periphery of top wall 442. Because top wall 442 has a generally rectangular configuration and because of the annular configuration of side wall 444, upper portions at opposite sides 446 and 448 of side wall 444 corresponding to the lengthwise sides of top wall 442 slope upwardly in a converging manner toward each other. The lips of a user of the device are placed on sides 446 and 448 during inhalation. Of course, since the user's mouth is placed over mouthpiece, the various edges thereof are rounded.

A central opening 450 is centrally formed in top wall 442, and an annular connecting tube 452 is formed at the lower surface of top wall 442 in surrounding relation to opening 450. When mouthpiece 440 is seated on swirl nozzle 380, connecting tube 452 receives the upper end of supply chimney 404 of swirl nozzle 380 therein.

In order to secure mouthpiece 440 to swirl nozzle 380, the lower end of side wall 444 has a circular or annular shape. At the inner surface of this lower end of side wall 444, there is formed an annular V-shaped projection 454 which extends inwardly in the radial direction. When mouthpiece 440 is positioned on swirl nozzle 380 and pressed down thereon, annular lip 422 of swirl nozzle 380, due to resilience of the plastic pieces, rides over V-shaped projection 454, so that V-shaped projection 454 retains annular lip 422, and thereby mouthpiece 440, on swirl nozzle 380. In such position, the lower edge of side wall 444 sits on annular ledge 420 of swirl nozzle 380.

Further, two sets of three gear teeth 460 are formed on the inner surface of diametrically opposite sides of annular side wall 444, immediately above annular V-shaped projection 454 and positioned centrally of opposite sides 446 and 448 of side wall 444. When mouthpiece 440 is assembled with swirl nozzle 380, gear teeth 460 engage with gear teeth 424 to prevent relative rotation between mouthpiece 440 and swirl nozzle 380.

Referring now to FIGS. 56–63, a closure cap 520 of metered powder dose dispenser 10 is provided as a closure for mouthpiece 440, and at the same time, functions to prime metered powder dose dispenser 10 for use. Specifically, closure cap 520 includes an upper elongated annular covering wall 522 which is closed at its upper end by a generally circular top wall 524. A lower annular securing skirt 526 of a larger diameter than annular covering wall 522, is secured to the lower end of annular covering wall 522 through an annular frusto-conical connector 528. The lower end of annular securing skirt 526 is open. Further, the inner diameter of lower annular securing skirt 526 is slightly larger than the outer diameter of upper annular wall 332 of adapter 320 so as to fit thereover.

In order to secure closure cap 520 onto metered powder dose dispenser 10, and particularly, in covering relation to mouthpiece 440, two helix cams 530 are formed in diametrically opposite relation on the inner surface of lower annular securing skirt 526. Thus, when closure cap 520 is inserted over powder housing 20, swirl nozzle 380 and mouthpiece 440, cams 530 of closure cap 520 initially vertically drop in entry 351 and then threadedly engage with double helical cam track 352 of adapter 320, until the lower edge of lower annular securing skirt 526 seats on the annular frusto-conical connecting section 334 of adapter 320.

It is noted that cams 530 and cam track 352 are provided in place of conventional screw threads. This is because, with conventional screw threads, cap 520 may be prematurely pulled off due to the tolerance of the threads. As a result, metered powder dose dispenser 10 may not be operated correctly, that is, not turned a full 180° during priming and delivery thereof. However, with cams 530 and cam track 352 having walls 353 of a square cross-section, numerous advantages are achieved, including preventing premature opening of cap 520, ease of use, ensuring proper location at all times of the rotational positions of the parts of dispenser 10, and ensuring that the counter (described hereinafter) is always correctly activated to always correctly change the dose count. Thus, cap 520 can not engage with adapter 320 until cams 530 are fully engaged in cam track 352, as shown best in FIGS. 89B and 89C.

It will be appreciated that the outer diameter of lower annular securing skirt 526 is substantially identical with the outer diameter of lower annular wall 322 of adapter 320 to provide a relative smooth, continuous appearance. In order to aid in the removal and closing of closure cap 520, the outer surface of lower annular securing skirt 526 is formed with a gripping surface 532 formed by undulations, knurling or the like, to enhance the gripping and rotating of closure cap 520.

As discussed above, closure cap 520 also serves to prime metered powder dose dispenser 10 for use. Specifically, a first pair of parallel, axially extending, spaced apart priming ribs 534 are formed on the inner surface of closure cap 520, extending a small distance down from frusto-conical connector 528 onto lower annular securing skirt 526. A second pair of parallel, axially extending, spaced apart priming ribs 536 are also formed on the inner surface of closure cap 520, extending a small distance down from frusto-conical connector 528 onto lower annular securing skirt 526, in diametrically opposite relation to priming ribs 534. The priming ribs 534 and 536 of each pair are spaced apart by a distance slightly less than the width of driving recesses 164 and 166, respectively, of driving body 120, for biasing spring fingers 163 and 165 inwardly, and also, for engaging sides of driving recesses 164 and 166 to rotate driving body 120. As shown best in FIGS. 59 and 63, each of the priming ribs 534 and 536 has a lower ramp portion 535 and an upper ramp portion 537 which meet at an intermediate projecting portion 539 and reduce in thickness as they move away from projecting portion 539.

When closure cap 520 is removed from metered powder dose dispenser 10, metered dose hole 184 is in alignment with venturi conduit 64, ready for inhalation by the user. Thus, dispenser 10 is fully primed and ready for inhalation by a person. At such time, spring fingers 163 and 165 are positioned in recesses 344 and 346 of adapter 320. Thus, dispenser 10 is locked in this position.

Figure 89C:
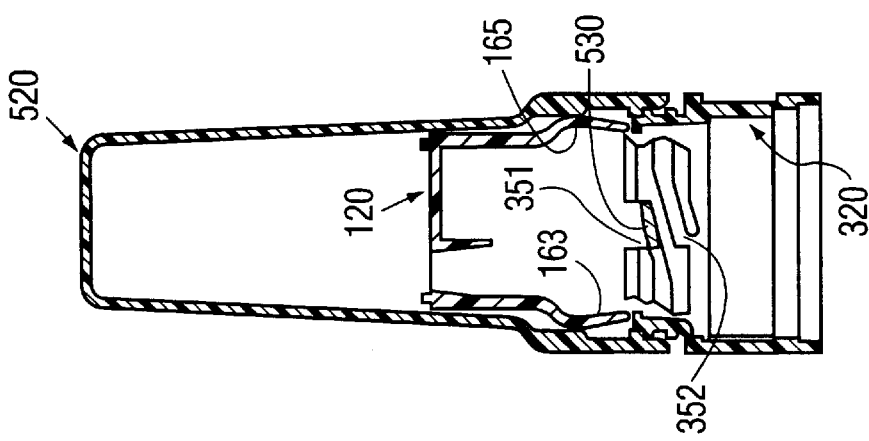
FIGS. 89A—89E are longitudinal cross-sectional drawings of a portion of the metered powder dose dispenser, showing closing of the cap during sequential times.
Figure 89B:
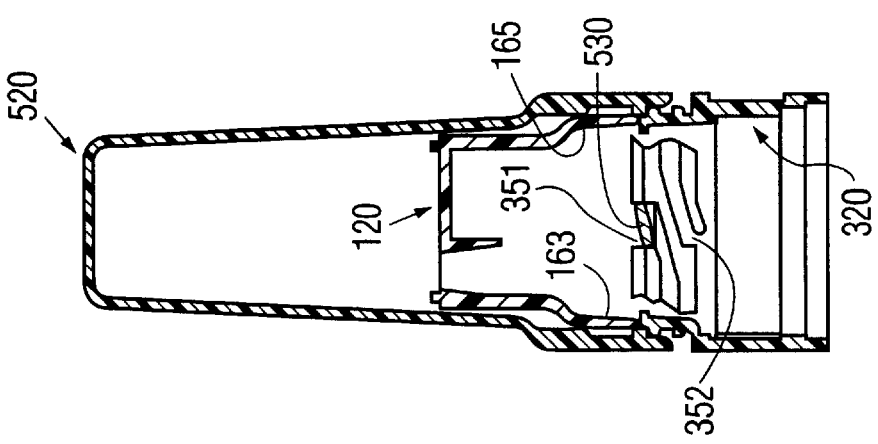
Figure 89A:
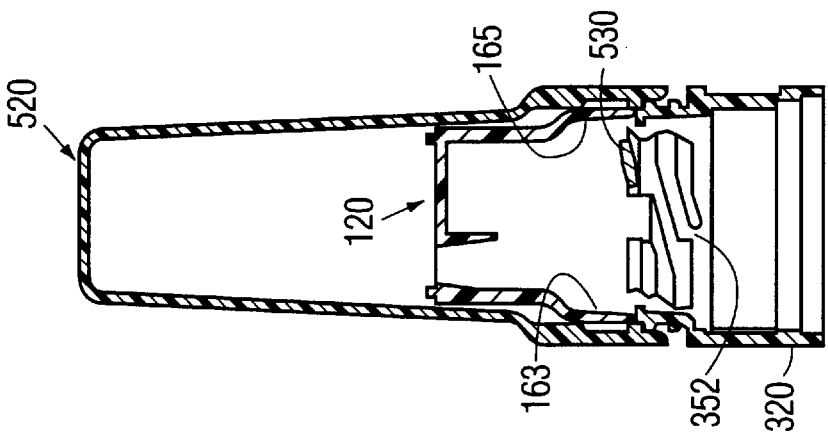
Figure 89D:
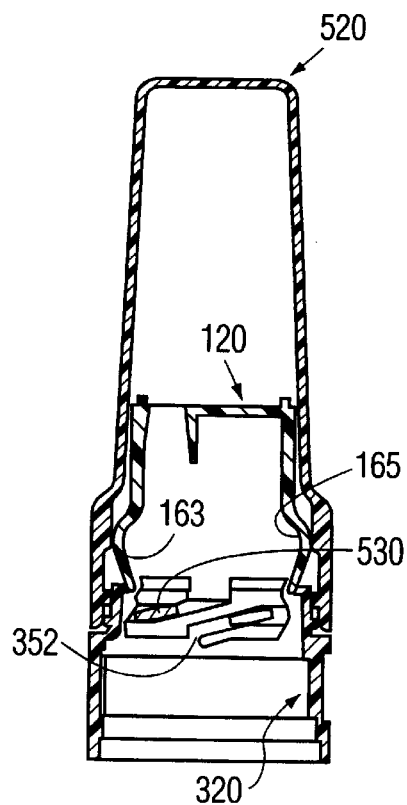
Figure 89E:
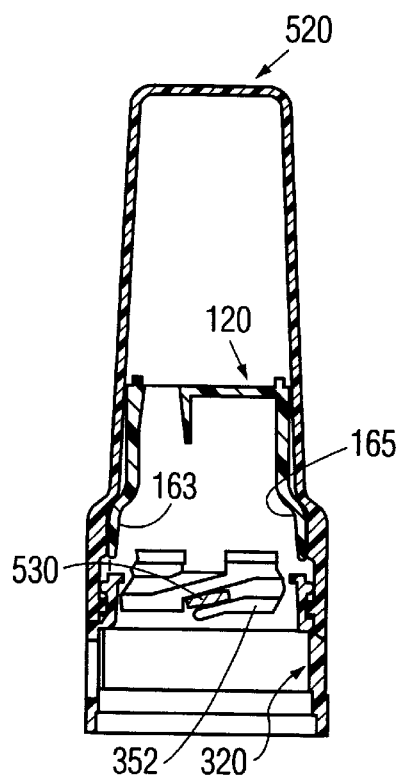

The operation of inserting closure cap 520 is shown in FIGS. 89A–89E and FIGS. 90A and 90B. After the inhalation operation, closure cap 520 is positioned on the assembly, as shown in FIG. 89A. At this time, cams 530 are not engaged within cam tracks 352. Upon turning of closure cap 520, cams 530 fall within the beginning portions of cam tracks 352 and can be pushed down therein, as shown in FIG. 89B and 89C. At this time, priming ribs 534 and 536 engage and push in spring fingers 163 and 165, and also engage sides of driving recesses 164 and 166. In other words, during the initial closure operation, lower ramp portions 535 of priming ribs 534 and 536 engage upper portions of spring fingers 163 and 165 and bias the same inwardly of driving recesses 344 and 346. This is shown in more detail in FIG. 90A. As a result, driving body 120 can rotate relative to adapter 320 to the closed position, as shown in FIGS. 89D and 89E. During this time, cap 520 engages with driving body 120, so that continued turning of cap 520 results in turning of driving body 120 relative to adapter 320. As cap 520 is rotated, it is pulled down by cams 530 riding in cam tracks 352.

At the completion of the rotation, and because of the configuration of spring fingers 163 and 165 and the complementary configuration of priming ribs 534 and 536, spring fingers 163 and 165 spring back into a locking position into mating engagement with priming ribs 534 and 536, 1800 offset from the inhalation position, that is, with spring fingers 163 and 165 positioned in recesses 346 and 344. Further, because of the mating relation of spring fingers 163 and 165 with priming ribs 534 and 536, priming ribs 534 and 536 are also, at this time, positioned in recesses 346 and 344. In other words, intermediate projecting portions 539 of priming ribs 534 and 536 are received within corresponding concave portions of spring fingers 163 and 165, as shown best in FIG. 90B.

It will be appreciated that when cap 520 is in the fully closed position of FIG. 89E, spring fingers 163 and 165 are returned to a free state, that is, a state in which there is no stress on spring fingers 163 and 165. This is provided so that over time, spring fingers 163 and 165 do not take a permanent set or deformation in a biased state, as with most plastic materials. This would be detrimental to the operation of the inhaler. The particular shapes of spring fingers 163 and 165 and priming ribs 534 and 536 are provided for this purpose.

Thus, closing rotation of closure cap 520 causes the rotation of driving body 120, and thereby of venturi conduit 64 relative to metered dose hole 184, to the stored position, 180° out of alignment. During this travel, powder 62 is scraped into metered dose hole 184, so that metered powder dose dispenser 10 is primed.

When the user is ready to use metered powder dose dispenser 10, closure cap 520 is unscrewed from adapter 320. During such movement, spring fingers 163 and 165 initially engage with bevels 345 on recesses 346 and 344 which cause spring fingers 163 and 165 to move inwardly in order not to hinder rotation. Thereafter, as cap 520 begins to rise, spring fingers 163 and 165 again are engaged by priming ribs 534 and 536 which push in spring fingers 163 and 165. In other words, during the initial opening operation, upper ramp portions 537 of priming ribs 534 and 536 engage upper portions of spring fingers 163 and 165 and bias the same inwardly of recesses 344 and 346. Accordingly, driving body 120 can rotate relative to adapter 320 to the open position.

This results in opposite rotation of driving body 120, and thereby of venturi conduit 64 relative to metered dose hole 184, to a position in alignment. Thus, as soon as closure cap 520 is removed, metered dose hole 184, which is filled with powder 62, is in alignment with venturi conduit 64, and ready for inhalation. There is thus no need to provide any additional priming and set-up operation after closure cap 520 is removed.

Further, closure cap 520 includes six equiangularly spaced protrusions 538 formed at the inner surface of covering wall 522, spaced a small distance from top wall 524.

Figure 64:
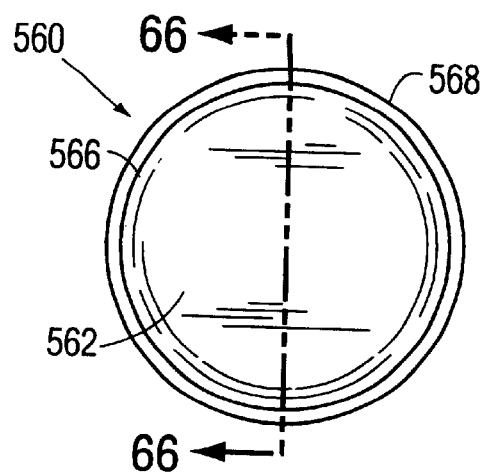
FIG. 64 is a bottom plan view of a desiccant holder of the metered powder dose dispenser of FIG. 1.
Figure 65:
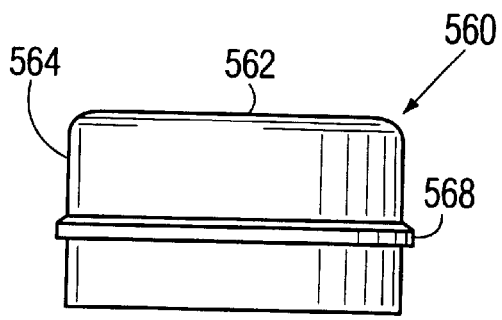
FIG. 65 is a side elevational view of the desiccant holder of FIG. 64.
Figure 66:
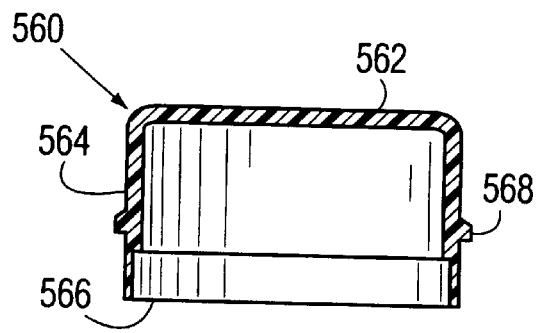
FIG. 66 is a cross-sectional view of the desiccant holder of FIG. 64, taken along line 66—66 thereof.
Figure 71:
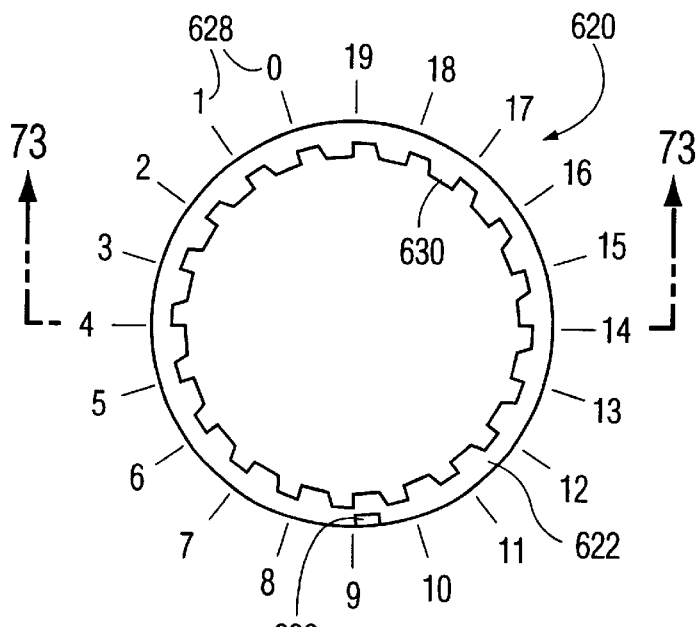
FIG. 71 is a top plan view of the intermittent counter ring of the metered powder dose dispenser of FIG. 1.
Figure 72:
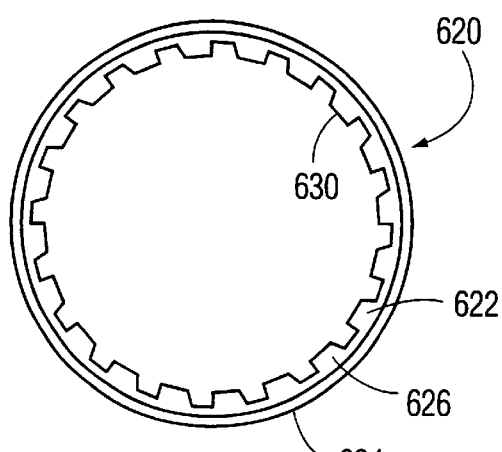
FIG. 72 is a bottom plan view of the intermittent counter ring of FIG. 71.
Figure 73:
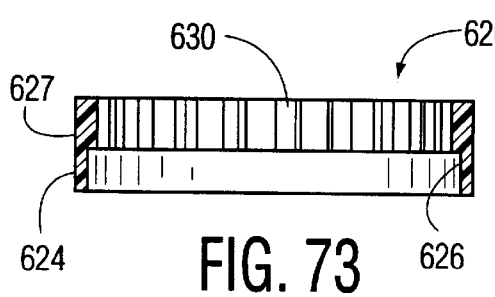
FIG. 73 is a cross-sectional view of the intermittent counter ring of FIG. 71, taken along line 73—73 thereof.
Figure 74:
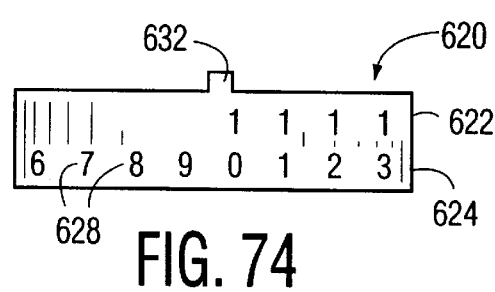
FIG. 74 is a side elevational view of the intermittent counter ring of FIG. 71.
Figure 75:
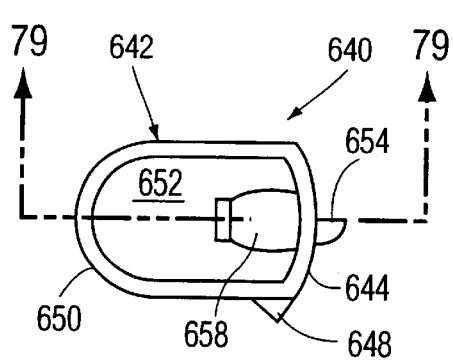
FIG. 75 is a top plan view of the pawl assembly of the metered powder dose dispenser of FIG. 1.
Figure 76:
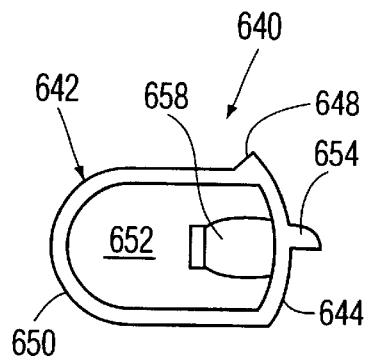
FIG. 76 is a bottom plan view of the pawl assembly of FIG. 75.
Figure 77:
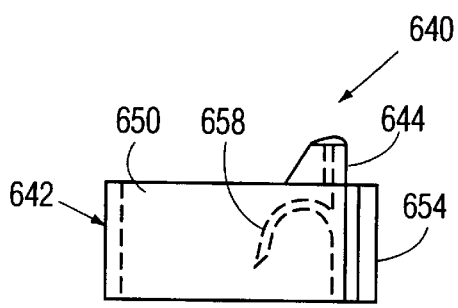
FIG. 77 is a side elevational view of the pawl assembly of FIG. 75.
Figure 78:
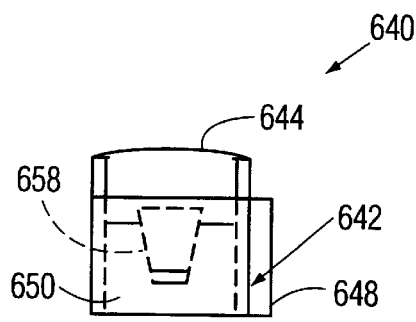
FIG. 78 is a rear elevational view of the pawl assembly of FIG. 75.
Figure 79:
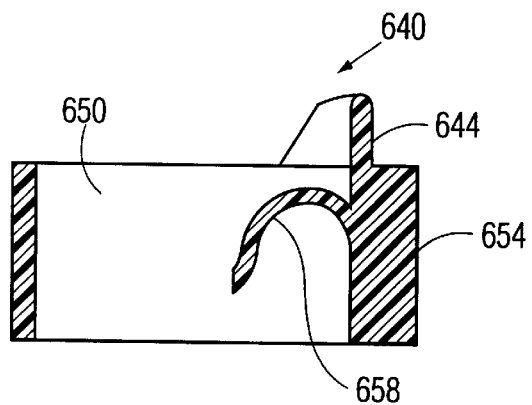
FIG. 79 is a cross-sectional view of the pawl assembly of FIG. 75, taken along line 79—79 thereof.
Figure 80:
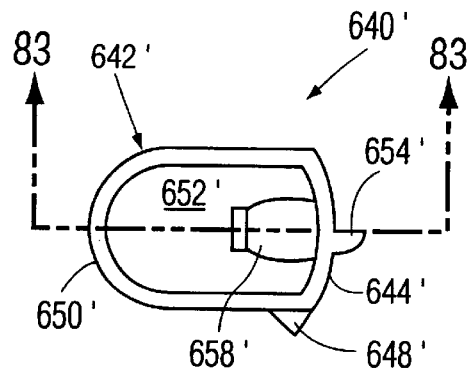
FIG. 80 is a top plan view of a pawl assembly according to another embodiment of the present invention.
Figure 81:
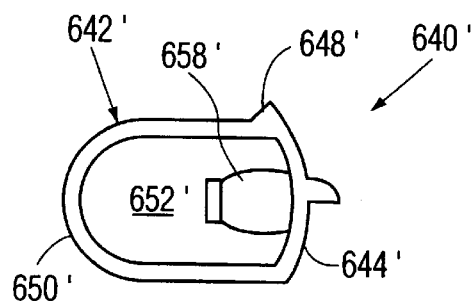
FIG. 81 is a bottom plan view of the pawl assembly of FIG. 80.
Figure 82:
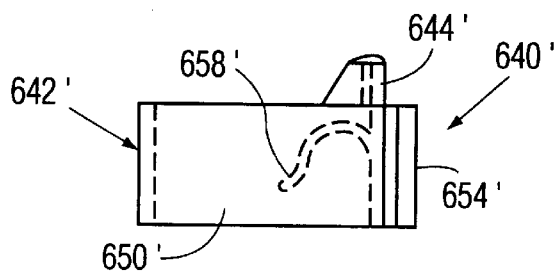
FIG. 82 is a side elevational view of the pawl assembly of FIG. 80.
Figure 83:
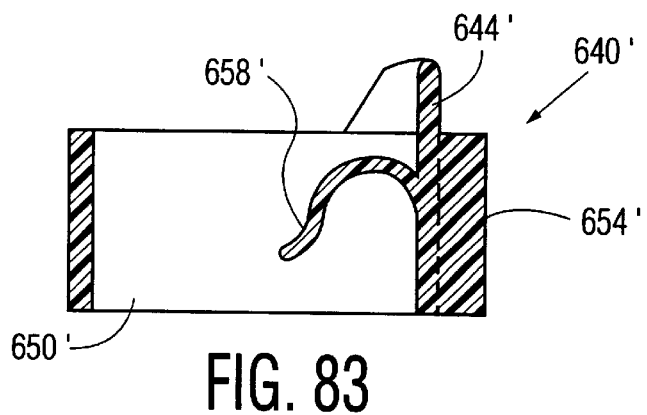
FIG. 83 is a cross-sectional view of the pawl assembly of FIG. 80, taken along line 83—83 thereof.
Figure 84:
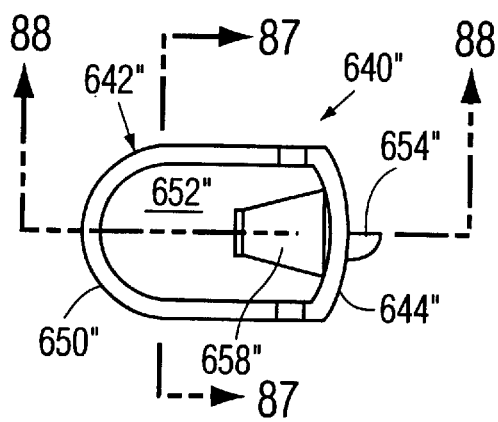
FIG. 84 is a top plan view of the pawl assembly according to another embodiment of the present invention.
Figure 85:
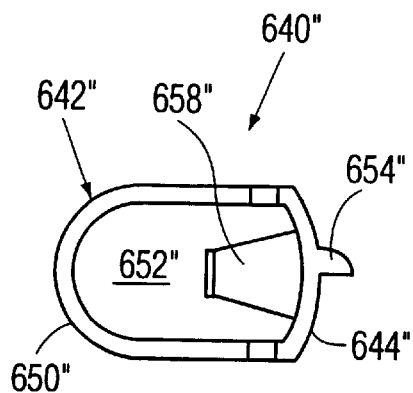
FIG. 85 is a bottom plan view of the pawl assembly of FIG. 84.
Figure 86:
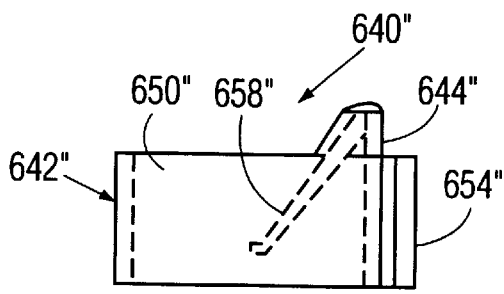
FIG. 86 is a side elevational view of the pawl assembly of FIG. 84.
Figure 87:
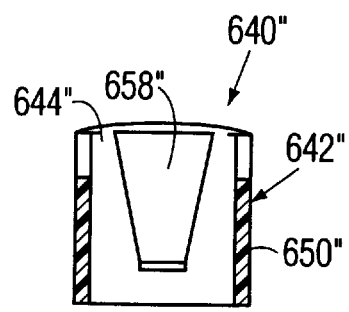
FIG. 87 is a cross-sectional view of the pawl assembly of FIG. 84, taken along line 87—87 thereof.
Figure 88:
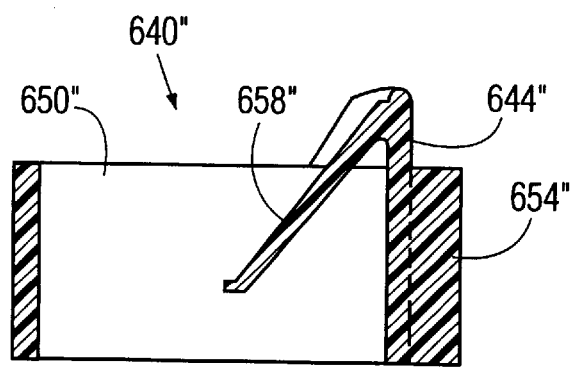
FIG. 88 is a cross-sectional view of the pawl assembly of FIG. 84, taken along line 88—88 thereof.

To protect powder 62 against moisture contamination, a desiccant holder 560 is held by protrusions 538 within closure cap 520. As shown in FIGS. 64–66, desiccant holder 560 includes a circular top wall 562 and an annular side wall 564 extending down from the periphery thereof. An annular recess 566 is formed in the inner surface of annular side wall 564 at the lower end thereof for receiving a disc (not shown) which holds a desiccant, such as silica gel, therein. An annular rib 568 is formed on the outer surface of annular side wall 564. In this manner, desiccant holder 560 is inserted within closure cap 520. Due to the resilience of the plastic pieces, annular rib 568 rides over protrusions 538, so that desiccant holder 560 is held within closure cap 520 adjacent top wall 524 thereof. A slight modification to desiccant holder 560 is shown in the assembled view of FIG. 4.

A counter mechanism 580 is provided for counting the number of doses that have been dispensed or indicating the number of doses that remain to be dispensed, so as to warn the user of impending powder depletion. Many types of mechanical and electrical counters are useful. A digital electronic counter can be disposed within the base or other areas of the device, and will require electrically conductive contacts which complete a circuit at some point in the dose loading operation; the characteristics of the required battery will be a factor in establishing a shelf life for the device. Presently preferred is counter mechanism 580, a decrementing mechanical counter that indicates the number of doses remaining to be dispensed.

Counter mechanism 580 is comprised of the aforementioned first and second rotation prevention spring detents 224 and 232 on base 200, the aforementioned transparent plastic window 330 of adapter 320, a continuous counter ring 590, an intermittent counter ring 620 and a spring-biased pawl assembly 640.

As shown in FIGS. 3, 4 and 67–70, continuous counter ring 590 is formed by a disc 592 having a wall * with a substantially rectangular cross-section. An outer annular ledge 594 is formed on the outer, upper edge of disc 592 by cutting away disc 592 thereat. Further, a lower annular lip 596 axially extends from the lower, outer edge of disc 592, as a smooth extension of disc 592, but of a lesser cross-sectional width. As a result, an inner annular ledge 598 is formed at the lower edge of disc 592. In this regard, continuous counter ring 590 can be seated on base 200, and in particular, inner annular ledge 598 seats upon circular top wall 202 of base 200 and lower annular lip 596 seats on annular ledge 206 of base 200 in surrounding relation to circular top wall 202.

A plurality of numerical indicia 600 are printed on the smooth combined outer surface of disc 592 and lower annular lip 596. Specifically, two successive sets of numbers "0" through "9" are printed equiangularly thereabout. Numerical indicia 600 are printed in a vertical manner. Thus, indicia 600 can be read while metered powder dose dispenser 10 is upright, that is, in the manner that it should be used.

Twenty gear teeth 602 are equiangularly formed on the inner surface of disc 592 in correspondence with the twenty numbers of numerical indicia 600. All gear teeth 602 have the same depth in the radial direction, with the exception that diametrically opposite gear teeth 604 and 606 of gear teeth 602, corresponding to the opposite numbers "5" of numerical indicia 600, are deeper than the remaining gear teeth 602, that is, gear teeth 604 and 606 extend outwardly in the radial direction to a greater extent than the remaining gear teeth 602. When continuous counter ring 590 is seated on base 200, first rotation prevention spring detent 224 of base 200 engages with one gear tooth 602 at a time, to prevent clockwise rotation of continuous counter ring 590 on base 200.

As shown in FIGS. 3, 4 and 71–74, intermittent counter ring 620 is formed by a disc 622 having a wall with a substantially rectangular cross-section. A lower annular lip 624 axially extends from the lower, outer edge of disc 622, as a smooth extension of disc 622, but of a lesser cross-sectional width. As a result, an inner annular ledge 626 is formed at the lower edge of disc 622. In this regard, intermittent counter ring 620 can be rotatably seated on continuous counter ring 590, and in particular, inner annular ledge 626 is spaced above continuous counter ring 590, while lower annular lip 624 seats on outer annular ledge 594 of continuous counter ring 590.

A plurality of numerical indicia 628 are printed on the smooth combined outer surface of disc 622 and lower annular lip 624. Specifically, numbers "0" through "19" are printed equiangularly thereabout. Numerical indicia 628 are printed in a vertical manner. Thus, indicia 628 can be read while metered powder dose dispenser 10 is upright, that is, in the manner that it should be used.

Twenty gear teeth 630 are equiangularly formed on the inner surface of disc 622 in correspondence with the twenty numbers of numerical indicia 628. All gear teeth 630 have the same depth in the radial direction. When intermittent counter ring 620 is seated on continuous counter ring 590, second rotation prevention spring detent 232 of base 200 engages with one gear tooth 630 at a time, to prevent clockwise rotation of intermittent counter ring 620 on base 200. As will be appreciated from the discussion which follows, gear teeth 630 extend along a larger diameter circle than gear teeth 602, so that gear teeth 630 are outwardly displaced in the radial direction from gear teeth 602.

Further, a dose limiting tab 632 extends upwardly from the upper surface of disc 622, corresponding to a position between numbers "9" and "10", to prevent operation of metered powder dose dispenser 10 after a prescribed number of doses have been dispensed. For example, where metered powder dose dispenser 10 is limited to dispensing 200 doses, dose limiting tab 632 can abut against a dosage limiter tab 336 of adapter 320 after dispensing of the two hundredth dose, to prevent further relative rotation of powder housing 20 with respect to metering dose plate 180, as will be described with respect to the operation hereinafter.

Initially, number "19" of indicia 628 is aligned with number "9" of indicia 600 to form the number 199, which is exposed through transparent plastic window 330 of adapter 320. After the first dose is dispensed, only continuous counter ring 590 rotates so that the numbers "19" and "8", respectively, are exposed to form the number "198" which is exposed through window 330. After the next nine doses, only continuous counter ring 590 rotates one increment at a time for each dose. After the number "190" is exposed through window 330, the next dose results in both continuous counter ring 590 and intermittent counter ring 620 rotating to form the number "189". This operation continues until the number "00" is exposed through window 330. At this time, intermittent counter ring 620 has been rotated to a position so that dose limiting tab 632 abuts against dosage limiter tab 336 of adapter 320, to prevent further relative rotation of powder housing 20 with respect to metering dose plate 180.

In order to cause such rotation of continuous counter ring 590 and intermittent counter ring 620, spring-biased pawl assembly 640 includes a pawl driver 642, as shown in FIGS. 3, 4 and 75–79. Pawl driver 642 includes an arcuate outer wall 644 having a height greater than the combined height of continuous counter ring 590 and intermittent counter ring 620. A U-shaped retainer 650 is connected to the free ends of arcuate wall 644. U-shaped retainer 650 has a height less than that of arcuate wall 644. Accordingly, a loop defining an open area 652, is formed by arcuate wall 644 and U-shaped retainer 650. A flange 648 of a substantially triangular cross-sectional configuration, forms an extension at one side of arcuate wall 644 at the intersection thereof with U-shaped retainer 650, but being of a height substantially equal to that of U-shaped retainer 650.

A pawl 654 is centrally formed on the outer or convex surface of arcuate wall 644. Thus, when pawl driver 642 is inserted on circular top wall 202 of base 200 in surrounding relation to cylindrical boss 216, pawl 654 can be inserted within a gear tooth 602. However, because gear teeth 630 extend along a larger diameter circle than gear teeth 602, pawl 654 can only engage with gear teeth 602 and not with gear teeth 630. The only exception is when pawl 654 engages within one of gear teeth 604 or 606. In such case, because gear teeth 604 and 606 are deeper than the remaining gear teeth 602, pawl 654 can reach into and engage with gear teeth 630. Since gear teeth 604 and 606 are spaced apart by ten gear teeth, pawl 654 engages within one of the gear teeth 604 or 606 every tenth dose dispensing, and thereby engages within one of gear teeth 630 at such time to rotatably drive intermittent counter ring 620 with continuous counter ring 590.

In order to bias pawl 654 into engagement with gear teeth 602, a bent, substantially inverted L-shaped spring 658 has one end integrally formed centrally, in regard to the widthwise and heightwise directions, at the inner surface of arcuate wall 644, with the free end thereof hanging down to push against cylindrical boss 216 of base 200 within radial segment 219, thereby biasing pawl assembly 640 outwardly in the radial direction. This causes pawl 654 to enter into engagement with gear teeth 602.

It will be appreciated that, by forming spring 658 integrally in a single molding operation with pawl assembly 640, the number of parts is reduced, a single molding operation is utilized, assembly of the parts is easier, and the spring can be made more flexible and reliable.

It will be appreciated that, when pawl assembly 640 is positioned on base 200, opposite sides of U-shaped retainer 650 are positioned within angled stub walls 221 and 223, so that there is just sufficient room for pawl assembly 640 to rotate by a small angle, in order to function as a ratchet assembly with respect to the gear teeth of counter rings 590 and 620.

Referring to FIGS. 80–83, there is shown a spring-biased pawl assembly 640' according to another embodiment of the present invention, in which elements corresponding to those of pawl assembly 640 of FIGS. 75–79 are identified by the same reference numerals, with a prime (') added thereto.

The only difference between pawl assembly 640' and pawl assembly 640 is that the free end of spring 658' of pawl assembly 640' has a slight convex curvature away from the fixed end thereof.

Referring to FIGS. 84–88, there is shown a spring-biased pawl assembly 640" according to still another embodiment of the present invention, in which elements corresponding to those of pawl assembly 640 of FIGS. 75–79 are identified by the same reference numerals, with a double prime (") added thereto.

One difference between pawl assembly 640" and pawl assembly 640 is that spring 658' of pawl assembly 640", rather than being formed as a substantially L-shaped member, is formed is a generally linear member with tapered sides, extending at an angle from the upper end of the inner surface of arcuate wall 644". Another difference is that flange 648 is eliminated entirely.

In the operation of counter mechanism 580, lower spring retainer 260 rotates 180° with reservoir body 22 relative to metering dose plate 180 between the stored position when closure cap 520 is threaded onto adapter 320 and the inhalation position when closure cap 520 is removed from adapter 320. When metered powder dose dispenser 10 is in the stored position, pawl 654 is engaged within a shallow gear tooth 602 of continuous counter ring 590, and therefore, does not engage with a gear tooth 630. Further, in such position, pawl driving end 276 of arcuate pawl driving wall 274 engages with pawl assembly 640.

When reservoir body 22 is rotated the first 178° toward the inhalation position, pawl driving end 278 of arcuate pawl driving wall 274 is rotated into engagement with the opposite side of pawl assembly 640. As a result, pawl 654 is rotated so that it rides out of the shallow gear tooth 602, thereby compressing spring 658. When ten doses have been dispensed, continued rotation to the full 180° causes pawl 654 to rotate a slight amount and fall into the next gear tooth 604, which is a deep gear tooth, for example. Specifically, spring 658 biases pawl 654 into gear tooth 604. Since gear tooth 604 is a deep gear tooth, pawl 654 also enters one of the gear teeth 630. At this point, metered powder dose dispenser 10 is in the inhalation position in which metered dose hole 184 is in alignment with venturi conduit 64.

After the user inhales the dose of powder 62, closure cap 520 is threaded back onto adapter 320. As a result, reservoir body 22 rotates back to its initial position, which also results in rotation of lower spring retainer 260. During this rotation back 180°, that is, pawl driving end 276 of arcuate pawl driving wall 274 engages with pawl assembly 640 at the end of its movement to rotate pawl assembly 640 to its initial position. During such movement, since pawl 654 is engaged within deep gear tooth 604 and one of the gear teeth 630, both continuous counter ring 590 and intermittent counter ring 620 are rotated together one increment. In the case where pawl 654 is not engaged with one of the deep gear teeth 604 or 606, pawl does not engage with a gear tooth 630, so that only the continuous counter ring 590 would be rotated.

It will be appreciated that continuous counter ring 590 and intermittent counter ring 620 cannot rotate in the opposite direction because of first and second rotation prevention spring detents 224 and 232 which engage with gear teeth 602 and 630, respectively.

It will be appreciated that various changes can be made to the scope of the present invention. For example, rotation of metering dose plate 180 need not be 180°, but could be for a lesser or greater arcuate distance. In such case, the length of arcuate pawl driving wall 274 would be changed to incrementally drive pawl assembly 640.

Accordingly, with the present invention, a metered powder dose dispenser 10 is provided that accurately measures the doses of powdered medicament to be delivered to the patient. Specifically, dispenser 10 is greatly simplified in construction and assembly over the prior art.

All of the above elements, with the exception of metal plate 93' and spring 290, are preferably fabricated from readily available plastics, while the former parts are preferably fabricated from suitable metals. Typically, the various components which do not require porosity or other special properties will be molded from one or more thermoplastic substances having the desired rigidity and strength. In some embodiments, the component containing the powder receptacle is relatively thin and, to maintain a required degree of surface flatness, will be constructed from a less easily deformed substance such as a reinforced plastic, ceramic or metal. Of course, materials selected must be chemically compatible with the medication to be dispensed. For reasons of cost, a maximum utilization of plastics will be preferred where the device is intended to be disposable with no, or only a limited number of, medicament refills after the initial charge has been dispensed. Other "composite" components can be used elsewhere in the device where special properties are required.

In order to assemble metered powder dose dispenser 10, powder housing 20 is first assembled. Specifically, reservoir plug 90 is inserted within reservoir body 22, desiccant holder 560 is snapped into closure cap 520, swirl nozzle 380 is assembled with driving body 120 and mouthpiece 440 is assembled with swirl nozzle 380. Next, continuous counter ring 590 is fit onto base 200 and intermittent counter ring 620 is fit onto continuous counter ring 590. Both counter rings 590 and 620 are rotated until the number "19", of intermittent counter ring 620 and the number "19" of continuous counter ring 590 are in alignment for display through window 330. In other words, this corresponds to the number "199".

Pawl assembly 640 is then positioned on top circular wall 202 of base 200 in surrounding relation to cylindrical boss 216 and between stub walls 221 and 223, with pawl 654 being biased into engagement with gear tooth 604 in alignment with the number "5" and the gear tooth 630 in alignment with the number "5", that is, in alignment with the number "5". It will be appreciated that first and second rotation prevention spring detents 224 and 232 are in alignment with gear tooth 606 corresponding to number "0" and with the gear tooth 630 corresponding to the number "19".

Thereafter, lower spring retainer 260 is positioned on boss 216 in surrounding relation to retaining post 218, with narrow driven ear 270 in alignment with the number "199" on rings 590 and 620. In such case, pawl driving end 276 thereof is in abutment with flange 648 of pawl assembly 640. Coil spring 290 is then seated on disc 262 of lower spring retainer 260, and support plate 300 is placed on top of coil spring 290, with narrow driven ear 306 thereof in alignment with narrow driven ear 270 of lower spring retainer 260. Then, annular mounting post 188 of metering dose plate 180 is positioned through central circular hole 310 of support plate 300 and over retaining post 218 of base 200, with bar 190 and slot 222 in alignment. In such case, metered dose hole 184 is in alignment with radially extending slot 312 of support plate 300.

Then, reservoir body 22, having reservoir plug 90 assembled therewith, is inserted over metering dose plate 180, support plate 300, coil spring 290 and lower support plate 260, such that narrow driven ears 270 and 306 fit within narrow drive. slot 34, and wider driven ears 272 and 308 fit within wider drive slot 36 of reservoir body 22. In such case, venturi conduit 64 is in alignment with metered dose hole 184. In order to assemble the above parts together, adapter 320 is then placed over the above assembly such that slot 326 thereof is in alignment with post 214 of base 200. Adapter 320 is then pressed down until annular ledge 210 of base 200 snaps into annular groove 324 of adapter 320. At this time, coil spring 290 is compressed, the number "199" appears through window 330 of adapter 320, and recesses 340 and 342 of adapter 320 are in alignment with drive slots 34 and 36, respectively, of reservoir body 22.

Thereafter, powder supply conduit 60 is filled through the upper open end thereof. Then, driving body 120, with nozzle 380 and mouthpiece 440 thereon, is fit over reservoir body 22, such that circular plug conduit 144 of driving body 120 plugs the upper open end of powder supply conduit 60 and such that the upper open end of venturi conduit 64 extends through circular opening 142 in driving body 120. In this position, the lower edge of lower annular skirt section 128 of driving body 120 is positioned immediately above the upper edge of upper annular wall 332 of adapter 320.

Closure cap 520 is then threaded onto adapter 320, whereby powder housing 20 is rotated 180° relative to metering dose plate 180 so as to prime metered powder dose dispenser 10, that is, so as to scrape powder 62 into metered dose hole 184. This moves pawl 654 to the next gear tooth 602.

When a user desires to inhale a dosage of the powder 62, closure cap 520 is unthreaded and removed, thereby rotating powder housing 20 back 180° so as to align venturi conduit 64 with metered dose hole 184, ready for inhalation. At this time, pawl 654 is rotated one increment, whereby the next number "198" is displayed through window 330. When all 200 doses have been used, dose limiting tab 632 of intermittent counter ring 620 abuts against dosage limiter tab 336 of adapter 320 to prevent further rotation for dispensing. Accordingly, the numbers will not continue from "00" to "199".

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. A powder dispenser comprising:

a supply holder for holding a supply of powdered material to be dispensed;

an inhalation conduit extending in a first direction and positioned in displaced relation to said supply holder;

a device for carrying a predetermined amount of said powdered material from said supply holder to said inhalation conduit; and a nozzle for reducing particle sizes of agglomerates of powdered material from the inhalation conduit to form micronized powdered material and for mixing said micronized powdered material with suction air, said nozzle including:

a swirl cavity for changing the direction of flow of said powder from said first direction of said inhalation conduit to a second direction different from said first direction and for substantially continuously changing the direction of flow of said powder in said second direction therein, said swirl cavity being defined by a top wall and a skirt connected to a periphery of said top wall, said top wall having an opening therein; and a supply chimney extending from said top wall in surrounding relation to said opening for changing the direction of flow of said powder from said second direction of said swirl cavity substantially back to said first direction, said supply chimney extending along an axial direction thereof and including an inner tubular wall surface having vertically oriented irregularities extending in said axial direction.

2. The powder dispenser according to claim 1, wherein said irregularities are formed by a plurality of flutes on said inner tubular wall surface.

3. The powder dispenser according to claim 2, wherein said flutes are formed by:

a plurality of first concave wall sections extending in said axial direction and having an arc of a first radius in a direction transverse to said axial direction, and a plurality of second wall sections extending in said axial direction and interconnecting said first concave wall sections.

4. The powder dispenser according to claim 3, wherein said second wall sections are of a concave configuration having an arc of a second radius in a direction transverse to said axial direction, said second radius being greater than said first radius.

5. The powder dispenser according to claim 1, wherein said top wall has a circular shape and said opening is centrally located in said top wall, and said swirl cavity includes a curved wall extending from said opening to said skirt.

6. The powder dispenser according to claim 5, wherein said curved wall extends in a substantially spiral manner.

7. The powder dispenser according to claim 5, wherein said curved wall is connected with said top wall.

8. The powder dispenser according to claim 1, wherein said supply chimney has a central axis and said inhalation conduit has a central axis parallel to and offset from the central axis of said supply chimney.

9. The powder dispenser according to claim 1 wherein:

said supply holder and inhalation conduit are included in a powder housing, said powder housing including:

a reservoir body including said supply of powdered material and said inhalation conduit, and a driving body secured to said reservoir body for driving said reservoir body in a rotational direction, said driving body including a plurality of recesses in an upper portion thereof;

said device for carrying comprises a metering plate including a metered dose hole for holding said predetermined amount of said powdered material, said metering plate being positionable below said supply of powdered material, and said metering plate and said powder housing being relatively bi-directionally rotatable with respect to each other about a common central axis so that said metered dose hole can be placed in fluid communication selectively with said supply of powdered material or said inhalation conduit;

said powder dispenser includes a spring for biasing said metering plate and said powder housing toward each other; and said nozzle is mounted to said driving body and includes at least one rib welded in said recesses of said driving body.

10. A powder dispenser according to claim 9, wherein said driving body has a top wall, and said recesses are arranged along a peripheral portion of said top wall.

11. A powder dispenser according to claim 10, wherein said top wall has a circular configuration, and said recesses are arranged along a common circle in said peripheral portion of said circular top wall.

12. A powder dispenser according to claim 9, wherein at least one of said recesses extends for a different length than another of said recesses, and said each of said at least one rib has a length corresponding to a respective one of said recesses.

13. A powder dispenser according to claim 9, wherein said at least one rib and said driving body are made from a plastic material, and said at least one rib is ultrasonically welded in said recesses of said driving body such that the plastic material of said at least one rib is fused into the plastic material of said recesses.

14. The powder dispenser according to claim 1 wherein:

said supply holder and inhalation conduit are included in a powder housing, said powder housing including:

a reservoir body including said supply of powdered material and said inhalation conduit, and a driving body secured to said reservoir body for driving said reservoir body in a rotational direction, said driving body including at least one driving recess with a spring finger in each driving recess;

said device for carrying comprises a metering plate including a metered dose hole for holding said predetermined amount of said powdered material, said metering plate being positionable below said supply of powdered material, and said metering plate and said powder housing being relatively bi-directionally rotatable with respect to each other about a common central axis so that said metered dose hole can be placed in fluid communication selectively with said supply of powdered material or said inhalation conduit;

and said powder dispenser further includes:

a spring for biasing said metering plate and said powder housing toward each other;

an adapter non-rotatably mounted with respect to said metering plate, said adapter including at least one locking recess for receiving said at least one spring finger therein to prevent rotation of said powder housing relative to said adapter and said metering plate; and a closure cap for covering said powder housing and for priming said powder dispenser for use, said closure cap including a priming arrangement for rotating said powder housing such that said inhalation conduit is in communication with said metered dose hole when said closure cap is removed from covering relation of said powder housing and for rotating said powder housing such that said inhalation conduit is out of communication with said metered dose hole when said closure cap is secured in covering relation to said powder housing, said priming arrangement including at least one priming rib for biasing said at least one spring finger out of said at least one locking recess of said adapter to enable rotation of said powder housing relative to said metering plate and for engaging with said at least one driving recess to rotate said powder housing relative to said metering plate.

15. The powder dispenser according to claim 14, wherein said driving body includes two diametrically opposite spring fingers, said adapter includes two diametrically opposite locking recesses and said cap includes at least two diametrically opposite priming ribs.

16. The powder dispenser according to claim 14, wherein each priming rib includes an upper ramp portion and a lower ramp portion which meet at an intermediate projecting portion and reduce in thickness as they move away from said projecting portion, such that said upper ramp portion initially biases said at least one spring finger out of said at least one locking recess during removal of said closure cap from said covering relation and said' lower ramp portion initially biases said at least one spring finger out of said at least one locking recess during securement of said closure cap to said covering relation.

17. The powder dispenser according to claim 16, wherein each said spring finger includes a depression which receives said projecting portion when said closure cap means is fully secured in said covering relation.

18. The powder dispenser according to claim 14, wherein said driving body includes two diametrically opposite driving recesses and two spring fingers extending within said two driving recesses in an unbiased condition.

19. The powder dispenser according to claim 1, wherein:
said supply holder and inhalation conduit are included in a powder housing;
said device for carrying comprises a metering plate including a metered dose hole for holding said predetermined amount of said powdered material, said metering plate being positionable below said supply of powdered material, and said metering plate and said powder housing being relatively bi-directionally rotatable with respect to each other about a common central axis so that said metered dose hole can be placed in fluid communication selectively with said supply of powdered material or said inhalation conduit;
and said powder dispenser further includes:
a spring for biasing said metering plate and said powder housing toward each other;
an adapter non-rotatably mounted with respect to said metering plate, said adapter including at least one helical cam track having a substantially square cross-sectional configuration; and
a closure cap for covering said powder housing and for priming said powder dispenser for use, said closure cap including a priming arrangement for rotating said powder housing such that said inhalation conduit is in communication with said metered dose hole when said closure cap is removed from covering relation of said, powder housing and for rotating said powder housing such that said inhalation conduit is out of communication with said metered dose hole when said closure cap is secured in covering relation to said powder housing, said closure cap including:
an annular skirt having an inner surface, and
at least one cam formed on a lower portion of the inner surface of annular skirt for riding within said at least one helical cam track.

20. The powder dispenser according to claim 19, wherein each said cam track includes an entry portion defining a vertical drop zone in which said at least one cam engages prior to permitting helical movement of said at least one cam within said at least one cam track.

21. The powder dispenser according to claim 19, wherein there are two said helical cam tracks and two said cams.

22. The powder dispenser according to claim 1, wherein:
said supply holder and inhalation conduit are included in a powder housing;
said device for carrying comprises a metering plate including a metered dose hole for holding said predetermined amount of said powdered material, said metering plate being positionable below said supply of powdered material, and said metering plate and said powder housing being relatively bi-directionally rotatable with respect to each other about a common central axis so that said metered dose hole can be placed in fluid communication selectively with said supply of powdered material or said inhalation conduit;
and said powder dispenser further includes:
a gas permeable retainer for retaining a dose of said powdered material in said metered dose hole, said retainer being positioned below said metered dose hole; and
a spring for biasing said metering plate and said powder housing toward each other;
said metering plate having an underside with ribs thereon;
said retainer being positioned in overlying relation to the underside of said metering plate and to said ribs thereon; and
said retainer being welded to said ribs such that said ribs are fused into said retainer.

23. The powder dispenser according to claim 22, wherein said retainer is formed by a material selected from the group consisting of a gas-permeable filter, a mesh screen, a porous material mesh and a perforated plate element.

24. The powder dispenser according to claim 22, wherein said retainer is ultrasonically welded to said ribs.

25. The powder dispenser according to claim 22, wherein said ribs are formed in a plurality of spaced apart, concentric circles.

26. The powder dispenser according to claim 22, wherein each rib has a substantially triangular cross-sectional configuration.

27. The powder dispenser according to claim 1, wherein:
said supply holder and inhalation conduit are included in a powder housing;
said device for carrying comprises a metering plate for holding a metered amount of said powdered material, said metering plate including metered dose hole for holding said predetermined amount of said powdered material, said metering plate being positionable below said supply of powdered material, and said metering plate and said powder housing being relatively bi-directionally rotatable with respect to each other about a common central axis so that said metered dose hole can be placed in fluid communication selectively with said supply of powdered material or said inhalation conduit;
and said powder dispenser further includes:
a spring for biasing said metering plate and said powder housing toward each other;
a base having an axially extending retaining post thereon coaxial with said common axis and non-rotatably connected with said metering plate, said base having oppositely angled walls on opposite sides of said post; and a counter, rotatably mounted on said base in surrounding relation to said retaining post, for providing a visual count of the number of doses of said powdered material that have been dispensed or remain to be dispensed in response to said relative rotation of said powder housing and said metering plate, said counter including:
- a counter ring assembly for providing said visual count, said counter ring assembly being rotatable about said common central axis and having counting indicia thereon for displaying said visual count, said counter ring assembly including:
  - a continuous counter ring having counting indicia thereon and gear teeth formed therearound on an inner surface thereof, and
  - an intermittent counter ring coaxially mounted with said continuous counter ring and having counting indicia thereon and gear teeth formed therearound on an inner surface thereof,
  - a display through which one of said counting indicia from said counter ring assembly is displayed to indicate a count corresponding to a number of doses of powdered material that have been dispensed or remain to be dispensed; and
- an actuating device for incrementally rotating said counter ring assembly in response to said relative rotation between said metering plate and said powder housing, said actuating device including a pawl assembly engaging with said gear teeth of said continuous counter ring and said intermittent counter ring for rotating said continuous counter ring one increment each time that a dose of the powdered material is dispensed to display another one of said counting indicia of said continuous counter ring through said display, and for rotating said intermittent counter ring one increment every predetermined number of rotational increments of said continuous counter ring to display another one of said counting indicia of said intermittent counter ring through said display, said pawl assembly including:
  - an outer wall having an outer surface and an inner surface,
  - at least one side wall connected with said outer wall and surrounding said axially extending retaining post and positioned between said angled walls in order to limit a rotation angle of said pawl assembly about said axially extending retaining post,
  - a pawl, integrally molded as a single piece with the outer surface of said outer wall, for engagement within the gear teeth of one of said continuous counter ring and said intermittent counter ring, and
  - a pawl spring, integrally molded as a single piece with the inner surface of said outer wall, for biasing said pawl into engagement with said gear teeth of said continuous counter ring and said intermittent counter ring, said pawl spring extending along a generally radial direction.

28. The powder dispenser according to claim 27, wherein said pawl spring has a generally L-shaped configuration.

29. The powder dispenser according to claim 27, wherein said pawl spring has a generally linear configuration and extends at an angle from the inner surface of said outer wall.

30. The powder dispenser according to claim 27, wherein said pawl spring has one end integrally molded with an upper portion of said inner surface of said outer wall.

31. The powder dispenser according to claim 27, wherein said gear teeth of said continuous counter ring are arranged in correspondence with said counting indicia thereon, and said gear teeth of said intermittent counter ring are arranged in correspondence with said counting indicia thereon.

32. The powder dispenser according to claim 27, wherein the gear teeth of said continuous counter ring include a plurality of successive first gear teeth of a first depth and at least one second gear tooth of a second, greater depth, each said second gear tooth being positioned after every predetermined number of said first gear teeth; and said intermittent counter ring includes a plurality of successive third gear teeth of a depth equal to the depth of each said second gear tooth of said continuous counter ring so that said pawl engages with successive ones of said first gear teeth during successive dosing operations and engages with one said second gear tooth and a third gear tooth of said intermittent counter ring after a plurality of the dosing operations.

33. The powder dispenser according to claim 27, wherein said actuating device further includes a pawl driver for incrementally rotating said pawl assembly, said pawl driver including a retainer rotatably mounted on said base coaxially with said continuous counter ring and said intermittent counter ring, said retainer including a first pawl driver for engaging with one side of said pawl assembly to incrementally rotate said pawl assembly in a first rotational direction at the end of rotation of said retainer in said first rotational direction and a second pawl driver for engaging an opposite side of said pawl assembly to incrementally rotate said pawl assembly in a second, opposite rotational direction at the end of rotation of said retainer in said second, opposite rotational direction.

34. The powder dispenser according to claim 27, wherein said indicia are oriented in an axial direction of said dispenser so that said indicia can be read when said dispenser is vertically oriented.

35. The powder dispenser of claim 1, wherein the irregularities in the supply chimney are formed by concave wall sections of a first radius, interconnected by concave wall sections of a larger radius.

36. The powder dispenser of claim 1, wherein the irregularities in the supply chimney are formed by planar wall sections.

37. A powder dispenser comprising:
- a powder housing for holding a supply of powdered material to be dispensed, said powder housing including an inhalation conduit extending therethrough in a first direction, in displaced relation to said supply of powdered material, said powder housing including:
  - a reservoir body including said supply of powdered material and said inhalation conduit, and
  - a driving body secured to said reservoir body for driving said reservoir body in a rotational direction, said driving body including:
    - a plurality of recesses in an upper portion thereof,
    - at least one driving recess in a lower portion thereof, and
    - at least one spring finger in said at least one driving recess;
- a metering plate for holding a metered amount of said powdered material, said metering plate including a metered dose hole for holding said metered amount of said powdered material, said metering plate being positionable below said supply of powdered material, and said metering plate and said powder housing being relatively bi-directionally rotatable with respect to each other about a common central axis so that said metered dose hole can be placed in fluid communication selectively with said supply of powdered material or said inhalation conduit, said metering plate having an underside with ribs thereon;

a gas permeable retainer for retaining a dose of said powdered material in said metered dose hole, said retainer being positioned below said metered dose hole and in overlying relation to the underside of said metering plate and to said ribs thereon, said retainer being welded to said ribs such that said ribs are fused into said retainer;

a spring for biasing said metering plate and said powder housing toward each other;

a nozzle, mounted to said driving body, for reducing particle sizes of agglomerates of powdered material from an inhalation conduit extending in a first direction in a powder dispenser to form micronized powdered material and for mixing said micronized powdered material with suction air, said nozzle comprising:

a swirl cavity for changing the direction of flow of said powder from said first direction of said inhalation conduit to a second direction different from said first direction and for substantially continuously changing the direction of flow of said powder in said second direction therein, said swirl cavity being defined by a top wall and a skirt connected to a periphery of said top wall, said top wall having an opening therein; and a supply chimney extending from said top wall in surrounding relation to said opening for changing the direction of flow of said powder from said second direction of said swirl cavity substantially back to said first direction, said supply chimney extending along an axial direction thereof and including an inner tubular wall surface having vertically oriented irregularities extending in said axial direction, and at least one rib welded in said recesses of said driving body;

an adapter non-rotatably mounted with respect to said metering plate, said adapter including:

at least one locking recess for receiving said at least one spring finger therein to prevent rotation of said powder housing relative to said adapter and said metering plate, and at least one helical cam track having a substantially square cross-sectional configuration;

a closure cap for covering said powder housing and for priming said powder dispenser for use, said closure cap including:

a priming arrangement for rotating said powder housing such that said inhalation conduit is in communication with said metered dose hole when said closure cap is removed from covering relation of said powder housing and for rotating said powder housing such that said inhalation conduit is out of communication with said metered dose hole when said closure cap is secured in covering relation to said powder housing, said priming arrangement including at least one priming rib for biasing said at least one spring finger out of said at least one locking recess of said adapter to enable rotation of said powder housing relative to said metering plate and for engaging with said at least one driving recess to rotate said powder housing relative to said metering plate, an annular skirt having an inner surface, and at least one cam formed on a lower portion of the inner surface of annular skirt for riding within said at least one helical cam track;

a base having an axially extending retaining post thereon coaxial with said common axis and non-rotatably connected with said metering plate; and a counter, rotatably mounted on said base in surrounding relation to said retaining post, for providing a visual count of the number of doses of said powdered material that have been dispensed or remain to be dispensed in response to said relative rotation of said powder housing and said metering plate, said counter including:

a counter ring assembly for providing said visual count, said counter ring assembly being rotatable about said common central axis and having counting indicia thereon for displaying said visual count, said counter ring assembly including:

a continuous counter ring having counting indicia thereon and gear teeth formed therearound on an inner surface thereof, and an intermittent counter ring coaxially mounted with said continuous counter ring and having counting indicia thereon and gear teeth formed therearound on an inner surface thereof, a display through which one of said counting indicia from said counter ring assembly is displayed to indicate a count corresponding to a number of doses of powdered material that have been dispensed or remain to be dispensed; and an actuating device for incrementally rotating said counter ring assembly in response to said relative rotation between said metering plate and said powder housing, said actuating device including a pawl assembly engaging with said gear teeth of said continuous counter ring and said intermittent counter ring for rotating said continuous counter ring one increment each time that a dose of the powdered material is dispensed to display another one of said counting indicia of said continuous counter ring through said display, and for rotating said intermittent counter ring one increment every predetermined number of rotational increments of said continuous counter ring to display another one of said counting indicia of said intermittent counter ring through said display, said pawl assembly including:

an outer wall having an outer surface and an inner surface, a pawl, integrally molded as a single piece with the outer surface of said outer wall, for engagement within the gear teeth of one of said continuous counter ring and said intermittent counter ring, a pawl spring, integrally molded as a single piece with the inner surface of said outer wall, for biasing said pawl assembly into engagement with said gear teeth of said continuous counter ring and said intermittent counter ring, said pawl spring extending along a generally radial direction.

* * * * *